US011776661B2

(12) United States Patent
Van De Stolpe et al.

(10) Patent No.: US 11,776,661 B2
(45) Date of Patent: Oct. 3, 2023

(54) DETERMINATION OF MAPK-AP-1 PATHWAY ACTIVITY USING UNIQUE COMBINATION OF TARGET GENES

(71) Applicant: InnoSIGN B.V., Eindhoven (NL)

(72) Inventors: Anja Van De Stolpe, Vught (NL); Laurentius Henricus Franciscus Maria Holtzer, Utrecht (NL)

(73) Assignee: InnoSIGN B.V., Eindhoven (NL)

( * ) Notice: Subject to any disclaimer, the term of this patent is extended or adjusted under 35 U.S.C. 154(b) by 1406 days.

(21) Appl. No.: 16/145,722

(22) Filed: Sep. 28, 2018

(65) Prior Publication Data

US 2019/0188359 A1 Jun. 20, 2019

(30) Foreign Application Priority Data

Dec. 20, 2017 (EP) .................................... 17209053

(51) Int. Cl.

| | |
|---|---|
| ***G16B 25/00*** | (2019.01) |
| ***G06N 5/02*** | (2023.01) |
| ***G16H 50/30*** | (2018.01) |
| ***G16H 50/20*** | (2018.01) |
| ***G06N 20/00*** | (2019.01) |
| ***G16B 5/00*** | (2019.01) |
| ***G16B 20/00*** | (2019.01) |
| ***G16C 20/70*** | (2019.01) |
| ***C12Q 1/6886*** | (2018.01) |
| ***G16H 20/10*** | (2018.01) |
| ***G16H 50/50*** | (2018.01) |
| ***G06N 7/01*** | (2023.01) |

(52) U.S. Cl.

CPC ........... *G16B 25/00* (2019.02); *C12Q 1/6886* (2013.01); *G06N 5/02* (2013.01); *G06N 7/01* (2023.01); *G06N 20/00* (2019.01); *G16B 5/00* (2019.02); *G16B 20/00* (2019.02); *G16C 20/70* (2019.02); *G16H 20/10* (2018.01); *G16H 50/20* (2018.01); *G16H 50/30* (2018.01); *G16H 50/50* (2018.01); *C12Q 2600/158* (2013.01)

(58) Field of Classification Search

CPC .......... G16B 25/00; G16B 5/00; G16B 20/00; G16H 50/50; G16H 50/30; G16H 50/20; G16H 20/10; G06N 20/00; G06N 5/02; G06N 7/005; G16C 20/70; C12Q 1/6886

See application file for complete search history.

(56) References Cited

U.S. PATENT DOCUMENTS

| | | | |
|---|---|---|---|
| 5,436,134 | A | 7/1995 | Haugland |
| 5,476,928 | A | 12/1995 | Langer |
| 5,658,751 | A | 8/1997 | Haugland |
| 5,874,219 | A | 2/1999 | Fodor |
| 5,958,691 | A | 9/1999 | Biesecker |
| 6,004,761 | A | 12/1999 | Brown |
| 6,146,897 | A | 11/2000 | Bhandare |
| 6,171,798 | B1 | 1/2001 | Gish |
| 6,225,047 | B1 | 5/2001 | Hutchens |
| 6,308,170 | B1 | 10/2001 | Baid |
| 6,391,550 | B1 | 5/2002 | Langer-Safer |
| 6,675,104 | B2 | 1/2004 | Braginsky |
| 6,713,297 | B2 | 3/2004 | Borkholder |
| 6,720,149 | B1 | 4/2004 | Fodor |
| 6,844,165 | B2 | 1/2005 | Hutchens |
| 6,884,578 | B2 | 4/2005 | Mahadevappa |
| 7,056,674 | B2 | 6/2006 | Baker |
| 7,081,340 | B2 | 7/2006 | Baker |
| 7,160,734 | B2 | 1/2007 | Hutchens |
| 7,208,470 | B2 | 4/2007 | Duan |
| 7,299,134 | B2 | 11/2007 | Hutchens |
| 7,526,637 | B2 | 4/2009 | Han |
| 7,544,476 | B1 | 6/2009 | O'Hagan |
| 7,569,345 | B2 | 8/2009 | Baker |
| 7,695,913 | B2 | 4/2010 | Baker |
| 7,723,033 | B2 | 5/2010 | Baker |
| 7,754,431 | B2 | 7/2010 | Beck |
| 7,754,861 | B2 | 7/2010 | Boschei |
| 7,816,084 | B2 | 10/2010 | Beck |
| 7,838,224 | B2 | 11/2010 | Baker |

(Continued)

FOREIGN PATENT DOCUMENTS

| | | | |
|---|---|---|---|
| WO | 2008079269 | A2 | 7/2008 |
| WO | 2013011479 | A2 | 1/2013 |

(Continued)

OTHER PUBLICATIONS

Eferi, Robert et al, "AP-1: a 5 double-edged sword in tumorigenesis", Nature Reviews Cancer, vol. 3, No. 11, pp. 859 to 868, 2003.

(Continued)

*Primary Examiner* — Jerry Lin

(74) *Attorney, Agent, or Firm* — Bond, Schoeneck & King, PLLC

(57) ABSTRACT

A bioinformatics process which provides an improved means to detect a MAPK-AP-1 cellular signaling pathway in a subject, such as a human, based on the expression levels of at least three unique target genes of the MAPK-AP-1 cellular signaling pathway measured in a sample. The invention includes an apparatus comprising a digital processor configured to perform such a method, a non-transitory storage medium storing instructions that are executable by a digital processing device to perform such a method, and a computer program comprising program code means for causing a digital processing device to perform such a method. Kits are also provided for measuring expression levels of unique sets of MAPK-AP-1 cellular signaling pathway target genes.

10 Claims, 21 Drawing Sheets

Specification includes a Sequence Listing.

(56) References Cited

U.S. PATENT DOCUMENTS

| | | | |
|---|---|---|---|
| 7,858,304 | B2 | 12/2010 | Baker |
| 7,888,019 | B2 | 2/2011 | Baker |
| 7,919,261 | B2 | 4/2011 | Fantin |
| 7,930,104 | B2 | 4/2011 | Baker |
| 7,939,261 | B2 | 5/2011 | Baker |
| 8,008,003 | B2 | 8/2011 | Baker |
| 8,021,894 | B2 | 9/2011 | Hutchens |
| 8,026,060 | B2 | 9/2011 | Baker |
| 8,029,995 | B2 | 10/2011 | Baker |
| 8,029,997 | B2 | 10/2011 | Kennedy |
| 8,034,565 | B2 | 10/2011 | Baker |
| 8,067,178 | B2 | 11/2011 | Baker |
| 8,071,286 | B2 | 12/2011 | Baker |
| 8,148,076 | B2 | 4/2012 | Baker |
| 8,153,378 | B2 | 4/2012 | Baker |
| 8,153,379 | B2 | 4/2012 | Baker |
| 8,153,380 | B2 | 4/2012 | Baker |
| 8,198,024 | B2 | 6/2012 | Baker |
| 8,206,919 | B2 | 6/2012 | Baker |
| 8,273,537 | B2 | 9/2012 | Baker |
| 8,367,345 | B2 | 2/2013 | Baker |
| 8,451,450 | B2 | 5/2013 | Heng |
| 8,518,639 | B2 | 8/2013 | Rihet |
| 8,541,170 | B2 | 9/2013 | Kennedy |
| 8,632,980 | B2 | 1/2014 | Baker |
| 8,703,736 | B2 | 4/2014 | Han |
| 8,725,426 | B2 | 5/2014 | Cherbavaz |
| 8,741,605 | B2 | 6/2014 | Baker |
| 8,762,069 | B2 | 6/2014 | Agur |
| 8,765,383 | B2 | 7/2014 | Collin |
| 8,808,994 | B2 | 8/2014 | Baker |
| 8,868,352 | B2 | 10/2014 | Baker |
| 8,906,625 | B2 | 12/2014 | Baker |
| 8,911,940 | B2 | 12/2014 | Kim |
| 9,076,104 | B2 | 7/2015 | Chang |
| 2005/0019785 | A1 | 1/2005 | Baker |
| 2013/0042333 | A1 | 2/2013 | Cairo |
| 2013/0178391 | A1 | 7/2013 | Bergstrom |
| 2014/0156200 | A1 | 6/2014 | Alves |
| 2014/0342924 | A1 | 11/2014 | Harkin |
| 2015/0232926 | A1 | 8/2015 | Wu |
| 2016/0117439 | A1 | 4/2016 | Brussel |
| 2016/0296480 | A1 | 10/2016 | Frank |

FOREIGN PATENT DOCUMENTS

| | | | |
|---|---|---|---|
| WO | 2014102668 | A2 | 7/2014 |
| WO | 2014174003 | A1 | 10/2014 |
| WO | 2015101635 | A1 | 7/2015 |
| WO | 2015193212 | A1 | 12/2015 |
| WO | 2016062891 | A1 | 4/2016 |

OTHER PUBLICATIONS

Zellmer, Victoria et al "Evolving concepts of tumor heterogeneity", Cell and Bioscience 2014, 4:69.

Verhaegh, W. et al., "Selection of personalized patient therapy through the use of knowledge-based computational models that identify tumor-driving signal transduction pathways", Cancer Research, vol. 74, No. 11, 2014, pp. 2936 to 2945.

Mudduluro, Giridhar et al, "PMA up-regulates the transcription of Axl by AP-1 transcription factor binding to TRE sequences via the MAPK cascade in leukaemia cells", Biology of the Cell, P vol. 103, pp. 21 to 33, 2010.

Miagkoufopoulou, C. et al., "A transcriptomics-based in vitro assay for predicting chemical genotoxicity in vivo", Carcinogenesis, vol. 33, No. 7, pp. 1421 to 1429, 2012.

Perego, Paola et al., "Modulation of cell sensitivity to antitumor agents by targeting survival pathways", Biochemical Pharmacology, 2010, vol. 80, No. 10, pp. 1459 to 1465—Abstract Only.

Ramsey, Jon E. et al., "The Zinc Finger Transcription Factor ZXDC Activates CCL2 Gene Expression by Opposing BCL6-mediated Repression", Molocular Immunology, vol. 56, No. 4, pp. 768 to 780, 2013.

Rogers, Simon et al. "Bayesian Model-Based Inference of Transcription Factor Activity", BMC Bioinformatics, 2007, vol. 8.

Su, Junjie et al "Accurate and reliable Cancer classification based on Probabilistic Inference of Pathway Activity", Plos One, vol. 4 ,(12), 2009.

Zhao, Chunyan et al "Genome-Wide Profiling of AP-1 Regulated transcription provides insights into the Invasiveness of Triple-Gegative Breast cancer", American Association for Cancer Research, 2014.

Comincini, Sergio et al "Gene Expression Analysis of an EGFR Indirectly related Pathway Identified PTEN and MMP9 as reliable Diagnostic Markers for Human Glial Tumor Specimens", Journal of Biomedicine and Biotechnology, 2009.

Kandasamy, K. et al "EGFR1 Signaling Pathway", Genome Biology, 2010.

Yamauchi, Mai et al "Epidermal growth factor Receptor Tyrosine Kinase Defines Critical prognostic Genes of Stage I Lung Adenocarcinoma", Plos One 2012.

Fröhlich, Holger et al "Dynamic Bayesian Network Modelin gof the Interplay between EGFR and hedgehog Signaling," Journals Plos One, 2015.

Shibata, Tatsuhiro et al "Gene Expression Profiling of Epedermal growth Factor receptio/KRAS Pathway Activation in Lung Adenocarcinoma", Cancer Science, Jul. 2007, vol. 98, No. 7, pp. 985-991.

Sene names of the 139 genes identified for stage IA prediction and their biological functions, Plus One 2012, vol. 7, No. 9.

Deferme, Lize et al., "Oxidative stress mechanisms do not discriminate between genotoxic and nongenotoxic liver carcinogens", Chemical Research in Toxicology, vol. 20 28, No. 8, pp. 1636 to 1646, 2015.

Goodfellow, Sarah J. etal., "WT1 and its transcriptional cofactor BASP1 redirect the differentiation pathway of an established blood cell line", Biochemical Journal, vol. 435, pp. 113 to 125, 2011.

Dyama, Masaaki et al., "Integrated quantitative analysis of the phosphoproteome and transcriptome in taximofen-resistant breast cancer", The Journal Of Biological Chemistry, vol. 286, No. 1, pp. 818 to 829, 2011.

Navarro, Francisco et al., "miR-34a contributes to megakaryocytic differentiation of K562 cells independently of p53", Blood, vol. 114, No. 10., pp. 2181 to 2192, 2009.

Yarden, Yosef et al., "Untangling the ErbB Signalling Network" Nature Reviews, Molecular Cell Biology, vol. 2, (2001) pp. 127-137.

SEQUENCE LISTING

<160> NUMBER OF SEQ ID NOS: 24

<210> SEQ ID NO 1
<211> LENGTH: 5106
<212> TYPE: DNA
<213> ORGANISM: Homo sapiens

<400> SEQUENCE: 1

```
acttcgctcc gcgcagccgc ctggtctgca gtttgttgga gctctgcgtc cagcgccgct      60

gccgctgccg ccgccgccgc cgccgccgcc gccgccgccg ccgccgccac taccaccact     120

tgattcttgc agccaccctg cgaaccctgc cacactgcga tcgcatcatc gcggtattcg     180

gttcgctgcg ttcccgccgc caccgcctcg gcgccctttc ttggcccttg ttcccccaaa     240

tgtctgactc tgactctcgg actgagaaac gcaagaaaaa aagaccaaat ggcaaagcaa     300

ccttctgatg taagttctga gtgtgaccga gaaggtagac aattgcagcc tgcggagagg     360

cctccccagc tcagacctgg ggcccctacc tccctacaga cagagccaca aggtaatcct     420

gaaggcaatc acggaggtga aggggacagc tgcccccacg gcagccctca gggcccgctg     480

gccccacctg ccagccctgg ccctttttgct accagatccc cgcttttcat ctttatgaga     540

agatcctccc tgctgtctcg atcctccagt gggtatttct cttttgacac agacaggagc     600

ccagcaccca tgagttgtga caaatcaaca caaaccccaa gtcctccttg ccaggccttc     660
```

```
aaccactatc tcagtgcaat ggcttccatg aggcaggctg aacctgcaga tatgcgccca    720
gagatatgga tcgcccaaga gttgcggcgt attggagacg agtttaacgc ttactatgca    780
aggagggtat ttttgaataa ttaccaagca gccgaagacc acccacgaat ggttatctta    840
cgactgttac gttacattgt ccgcctggtg tggagaatgc attgacaggt tctttgcgga    900
gccgagatac catgcagaca ttttgcttgt tcaaaccaac aagacccagc accgcggtct    960
cctggtgcca ttattatgca gccagcggtt ctcttgtgga gggggcaggt gacgtttcag   1020
aagacaccga gctggatggg actacctttc tgttcatcac cacacagcag aatttctaat   1080
ggaagtttgt tgtgaatgta aaggagggag cattctttgc tttttaatat acaaaccatg   1140
gtttttgga gcaggatttt gtgtaagaat ggtgtttaca tgcagtgtgt tttccccctc   1200
accttcaata aggtttttca aaaaggaaat ggaaactttt taaccaattt gtgaataact   1260
tttgtattaa aattttaaga acctacggcc tattctcaga ggattatgta acccctgcag   1320
tggaaactga gccagctaac ttaaaaagct gccttagttt atttttagag attacagaat   1380
ttttaaacag ggagacgtgt gatatactcc ctcccttccc tactattgcc tctctgacct   1440
ttttaaatta tttttaatac caaaagagtt cttttgaaat ggaactgatt aaaagggcag   1500
agggtctgtt gccagcctgc attgatatac cagtcccatt tgtaaatatt tacgtacctt   1560
tataaattca gttgcatctg tggcaaaatt tcagactatt tttgcgtctt tcctcatcac   1620
tttttgtgat gcaactccag tctggactca gatgcataga tttggtccag tgtattttca   1680
tgataaagtg aaattgagtc agaacaagag ttaatatctg cctgtatctt gcacagttcg   1740
agcgatctgt tattaactgg gaagcatttg gtgttggttt tcattccatt tcgacgagca   1800
tgttattggg aagtattctg aagaggcaat agcagtaata acaacagact taagtgctac   1860
gccccttttgt gctgctggct tttctggttg caggctttcc catggtcaca ggatgcactg   1920
tcagcatcag gtcccagagg gccaccgtgt ccattacagc agagtccagc tgcagcatcc   1980
agctcacgcc ctcatgggaa ttggcacagg cctggggcag ggcttctgat ggccatttgc   2040
ttggcctcct gcattttagt ccaactcaca gtccactagc ttcactcctt taaattcact   2100
ttgaaacagg cctcatccca cttccaccag caccatagaa gaataattct gggcagaagt   2160
ctgttttttt tcatttttcc aggacagttg gatattgtca ggccacttgt gaccccagcc   2220
atgtagtgag ggtgctcttt ctctgtgcct gctccttatg agtgcagtgg aaggaagcca   2280
cacactggtc agtcatttca gaggcagcag atgcccaggg agacccaaga aagagtcagg   2340
ttagggagca gtgaaagtga ggagggaaga caattctgtg aactctgtaa ctcttaaaat   2400
ttttgaaaac tccatcgtta aacaactttt aaaagaaata actaaatttt caaatgagta   2460
agcagtgcca ccaactagtg ttttgcccga tagaagagcc agcatgttca cgttatttaa   2520
attaggtgga aaaatctaaa catttttatc ttcataattt aaaaaatata tatgtatata   2580
ttgcatattc actttttcct ttaggtagag atgatttcaa tccaaatact cttactttaa   2640
aaaatttcct ttccccaaga atctccttgg gactttgact tatttttaaa gctgtgttgg   2700
agctcatctt gttccctgat gtgtctcgag cccattggta gggtcataca aagcccacgg   2760
ttacaagcag tggtaggatt gcagccgtgg gcctgctgga cacacacata caccaaagat   2820
gtatttggat ctgggcaccc cctcccagga tccctgtact cacgtgccag tctcctgact   2880
agagcacttt actctgtttc ctcagccctg cagcccctgg gagcacacac tgggtgcagc   2940
cctgggccag gcacgggagg ccctgccctg tgctgcccag ggctgtgtg caccacatga   3000
```

```
gcacatttcc ctctggcctg gcggcctcca ggctggctgt ggaaacagtt cctgaggaaa   3060

ttagagattc tatgaattgt aggagtatta aagaccaggc tgttggcacc agaacttaaa   3120

gcgatgactg gatgtctctg tactgtatgt atctggttat caagatgcct ctgtgcagaa   3180

agtatgcctc ccgtgggtat acgtttttac ctttttttaaa aaacattttt gtagaaaaaa   3240

taattaaatc cccttttttgg aaacttactg caggttttgt gccttgacaa cctctcccta   3300

tgtgaggttt gtaaaaagtg tcctgtgact taacacagaa acgcaataaa cacacacaaa   3360

atagtttcat gagtgattct tcagatgccc ttcccaactg gttagttgat caagaatttt   3420

gggggtgggg gttgcggaga aatcaagttt aaaattcctt ctgattaaaa aaatatagtg   3480

gaatacaatt gtctgccgtt tcccccttctt aatgtatata ttgtgagtat ttattagatt   3540

cgtaggtcat attacttatc aactgagcca aatgtctgtg tgcaattgtg tttcctttac   3600

cttgtaaaat tttgtacagc ataaataagt aaaaaaatca ctgtttttct caactttttc   3660

aaaatcaagg attgtaaata ttgtagattc tttttctgtg tgatgtgtcc tactgtttca   3720

taatgctgta acttgtagaa atattgtata tttattttct gcttatttaa tgtcttaatt   3780

tctgaaaagt attaacatcc ctgtctccca ctcccctgcc gtcccatgaa gttaactcct   3840

gagagttgtc gggggtgact ggagagctca ttgcagacca cgtggtcctc cagggtggct   3900

ctccaccttc gggtcctggt atttccagtc aagtgggttt caattcttgg gctttgccgc   3960

ccttatgatg aagtgtgtgt ttgatgccag tgagaaactc agtctggcag gctacaaaat   4020

tctactccaa gaaataccca gcaaccttct gtttgttcca aagcaactag cttatcatgc   4080

aagcaaattt tgctgactcc aggctttatc tttaggaaaa caaaaaaacc aaagtattat   4140

cagcaggtgg gaaagatttt tctattgaaa atttatccct gacaactcag cgtttagaaa   4200

agaaataaaa tgtgccactt ccagaggtgc tgcattgcag ttgttcaggg ctagggccag   4260

gcaggacaag tgaatgggtg ggacaggtgg ctcctgccta aggaccacct caggccacta   4320

acccccttgtg gacaactgtg agtagctggg ttttccccca cctgctgtgc aacttcctgt   4380

gctttgaggt tggactaact tgtcttcagg agctaattaa ctgtacagcc ctccccacgc   4440

cccacccata cggtcactgc atttggtcag cctgcttctt caggtcgatg ccctccttct   4500

gatactccat ctccttcagg ggaggttggg gccccactgg actgggtgtc aagatgtgaa   4560

agcttatggg agctttaagg agacttcatg gtggttccat gcaggtggtt ctgccatccc   4620

tgctgattta gcctggtgcc tgtgtgtgtc cactcacgta cacgtggggt gggggaaacg   4680

tgtctacaga tgacgctaaa tcagttgggg tctactctaa acagcattgt gtgtaagaag   4740

catcctcaag ctcccagtta agtaacttga ctacttttat ttgggaattt cagactatag   4800

aagctctctt atgttttatg tccagattct gtgaccacta gttactgtat cagaactcat   4860

caggtaccca cttataaata gcactgatct ggctgtatac tgatccatca ctaacctgtt   4920

ttctaggacc cagcgtatgt agcatttgta ttgcagtttc cctggcttac ttgtgttttg   4980

cactgatgaa ttttgacagg gtaattgcca ctttacttgt gcaatactgc tgtaaataac   5040

tgcagatttt taaacaatct tttatgttaa ttttataaaa ataaaacttt caactagtta   5100

aaaaaa                                                              5106
```

<210> SEQ ID NO 2
<211> LENGTH: 4304
<212> TYPE: DNA
<213> ORGANISM: Homo sapiens

<400> SEQUENCE: 2

-continued

```
cacacggact acaggggagt tttgttgaag ttgcaaagtc ctggagcctc cagagggctg     60
tcggcgcagt agcagcgagc agcagagtcc gcacgctccg gcgaggggca gaagagcgcg    120
agggagcgcg gggcagcaga agcgagagcc gagcgcggac ccagccagga cccacagccc    180
tccccagctg cccaggaaga gccccagcca tggaacacca gctcctgtgc tgcgaagtgg    240
aaaccatccg ccgcgcgtac cccgatgcca acctcctcaa cgaccgggtg ctgcgggcca    300
tgctgaaggc ggaggagacc tgcgcgccct cggtgtccta cttcaaatgt gtgcagaagg    360
aggtcctgcc gtccatgcgg aagatcgtcg ccacctggat gctggaggtc tgcgaggaac    420
agaagtgcga ggaggaggtc ttcccgctgg ccatgaacta cctggaccgc ttcctgtcgc    480
tggagcccgt gaaaaagagc cgcctgcagc tgctgggggc cacttgcatg ttcgtggcct    540
ctaagatgaa ggagaccatc cccctgacgg ccgagaagct gtgcatctac accgacaact    600
ccatccggcc cgaggagctg ctgcaaatgg agctgctcct ggtgaacaag ctcaagtgga    660
acctggccgc aatgaccccg cacgatttca ttgaacactt cctctccaaa atgccagagg    720
cggaggagaa caaacagatc atccgcaaac acgcgcagac cttcgttgcc ctctgtgcca    780
cagatgtgaa gttcatttcc aatccgccct ccatggtggc agcggggagc gtggtggccg    840
cagtgcaagg cctgaacctg aggagcccca acaacttcct gtcctactac cgcctcacac    900
gcttcctctc cagagtgatc aagtgtgacc cggactgcct ccgggcctgc caggagcaga    960
tcgaagccct gctggagtca agcctgcgcc aggcccagca gaacatggac cccaaggccg   1020
ccgaggagga ggaagaggag gaggaggagg tggacctggc ttgcacaccc accgacgtgc   1080
gggacgtgga catctgaggg cgccaggcag gcgggcgcca ccgccacccg cagcgagggc   1140
ggagccggcc ccaggtgctc ccctgacagt ccctcctctc cggagcattt tgataccaga   1200
agggaaagct tcattctcct tgttgttggt tgtttttttcc tttgctcttt ccccccttcca   1260
tctctgactt aagcaaaaga aaaagattac ccaaaaactg tctttaaaag agagagagag   1320
aaaaaaaaaa tagtatttgc ataaccctga gcggtggggg aggagggttg tgctacagat   1380
gatagaggat tttatacccc aataatcaac tcgtttttat attaatgtac ttgtttctct   1440
gttgtaagaa taggcattaa cacaaaggag gcgtctcggg agaggattag gttccatcct   1500
ttacgtgttt aaaaaaaagc ataaaaacat tttaaaaaca tagaaaaatt cagcaaacca   1560
tttttaaagt agaagagggt tttaggtaga aaaacatatt cttgtgcttt tcctgataaa   1620
gcacagctgt agtggggttc taggcatctc tgtactttgc ttgctcatat gcatgtagtc   1680
actttataag tcattgtatg ttattatatt ccgtaggtag atgtgtaacc tcttcacctt   1740
attcatggct gaagtcacct cttggttaca gtagcgtagc gtgcccgtgt gcatgtcctt   1800
tgcgcctgtg accaccaccc caacaaacca tccagtgaca aaccatccag tggaggtttg   1860
tcgggcacca gccagcgtag cagggtcggg aaaggccacc tgtcccactc ctacgatacg   1920
ctactataaa gagaagacga aatagtgaca taatatattc tatttttata ctcttcctat   1980
ttttgtagtg acctgtttat gagatgctgg ttttctaccc aacggccctg cagccagctc   2040
acgtccaggt tcaacccaca gctacttggt ttgtgttctt cttcatattc taaaaccatt   2100
ccatttccaa gcactttcag tccaataggt gtaggaaata gcgctgtttt tgttgtgtgt   2160
gcagggaggg cagttttcta atggaatggt ttgggaatat ccatgtactt gtttgcaagc   2220
aggactttga ggcaagtgtg ggccactgtg gtggcagtgg aggtggggtg tttgggaggc   2280
tgcgtgccag tcaagaagaa aaaggtttgc attctcacat tgccaggatg ataagttcct   2340
```

```
ttccttttct ttaaagaagt tgaagtttag gaatcctttg gtgccaactg gtgtttgaaa   2400

gtagggacct cagaggttta cctagagaac aggtggtttt taagggttat cttagatgtt   2460

tcacaccgga aggtttttaa acactaaaat atataattta tagttaaggc taaaaagtat   2520

atttattgca gaggatgttc ataaggccag tatgatttat aaatgcaatc tccccttgat   2580

ttaaacacac agatacacac acacacacac acacacacaa accttctgcc tttgatgtta   2640

cagatttaat acagtttatt tttaaagata gatcctttta taggtgagaa aaaaacaatc   2700

tggaagaaaa aaaccacaca aagacattga ttcagcctgt ttggcgtttc ccagagtcat   2760

ctgattggac aggcatgggt gcaaggaaaa ttagggtact caacctaagt tcggttccga   2820

tgaattctta tcccctgccc cttcctttaa aaaacttagt gacaaaatag acaatttgca   2880

catcttggct atgtaattct tgtaattttt atttaggaag tgttgaaggg aggtggcaag   2940

agtgtggagg ctgacgtgtg agggaggaca ggcgggagga ggtgtgagga ggaggctccc   3000

gaggggaagg ggcggtgccc acaccgggga caggccgcag ctccattttc ttattgcgct   3060

gctaccgttg acttccaggc acggtttgga aatattcaca tcgcttctgt gtatctcttt   3120

cacattgttt gctgctattg gaggatcagt tttttgtttt acaatgtcat atactgccat   3180

gtactagttt tagttttctc ttagaacatt gtattacaga tgcctttttt gtagtttttt   3240

ttttttttat gtgatcaatt ttgacttaat gtgattactg ctctattcca aaaaggttgc   3300

tgtttcacaa tacctcatgc ttcacttagc catggtggac ccagcgggca ggttctgcct   3360

gctttggcgg gcagacacgc gggcgcgatc ccacacaggc tggcgggggc cggccccgag   3420

gccgcgtgcg tgagaaccgc gccggtgtcc ccagagacca ggctgtgtcc ctcttctctt   3480

ccctgcgcct gtgatgctgg gcacttcatc tgatcggggg cgtagcatca tagtagtttt   3540

tacagctgtg ttattctttg cgtgtagcta tggaagttgc ataattatta ttattattat   3600

tataacaagt gtgtcttacg tgccaccacg gcgttgtacc tgtaggactc tcattcggga   3660

tgattggaat agcttctgga atttgttcaa gttttgggta tgtttaatct gttatgtact   3720

agtgttctgt ttgttattgt tttgttaatt acaccataat gctaatttaa agagactcca   3780

aatctcaatg aagccagctc acagtgctgt gtgccccggt cacctagcaa gctgccgaac   3840

caaaagaatt tgcaccccgc tgcgggccca cgtggttggg gccctgccct ggcagggtca   3900

tcctgtgctc ggaggccatc tcgggcacag gcccaccccg ccccacccct ccagaacacg   3960

gctcacgctt acctcaacca tcctggctgc ggcgtctgtc tgaaccacgc gggggccttg   4020

agggacgctt tgtctgtcgt gatggggcaa gggcacaagt cctggatgtt gtgtgtatcg   4080

agaggccaaa ggctggtggc aagtgcacgg ggcacagcgg agtctgtcct gtgacgcgca   4140

agtctgaggg tctgggcggc gggcggctgg gtctgtgcat ttctggttgc accgcggcgc   4200

ttcccagcac caacatgtaa ccggcatgtt tccagcagaa gacaaaaaga caaacatgaa   4260

agtctagaaa taaaactggt aaaaccccaa aaaaaaaaaa aaaa                    4304
```

```
<210> SEQ ID NO 3
<211> LENGTH: 924
<212> TYPE: DNA
<213> ORGANISM: Homo sapiens

<400> SEQUENCE: 3

gaggtcagag acttaagtct aaggcactga gcgtatcatg ttaaagatga gcgggtggca     60

gcgacagagc caaaatcaga gctggaacct gaggagagag tgttcaagaa ggaagtgtat    120

cttcatacat caccacacct gaaagcagat gtgcttttcc agactgatcc aactgcagag    180
```

atggcagctg agtcattgcc tttctccttc gggacactgt ccagctggga gctggaagcc 240
tggtatgagg acctgcaaga ggtcctgtct tcagatgaaa atgggggtac ctatgtttca 300
cctcctggaa atgaagagga agaatcaaaa atcttcacca ctcttgaccc tgcttctctg 360
gcttggctga ctgaggagga gccagaacca gcagaggtca caagcacctc ccagagccct 420
cactctccag attccagtca gagctccctg gctcaggagg aagaggagga agaccaaggg 480
agaaccagga aacggaaaca gagtggtcat tccccagccc gggctggaaa gcagcgcatg 540
aaggagaaag aacaggagaa tgaaaggaaa gtggcacagc tagctgaaga gaatgaacgg 600
ctcaagcagg aaatcgagcg cctgaccagg gaagtagagg cgactcgccg agctctgatt 660
gaccgaatgg tgaatctgca ccaagcatga acaattggga gcatcagtcc cccacttggg 720
ccacactacc cacctttccc agaagtggct actgactacc ctctcactag tgccaatgat 780
gtgaccctca atcccacata cgcaggggga aggcttggag tagacaaaag gaaaggtctc 840
agcttgtata tagagattgt acatttattt attactgtcc ctatctatta aagtgacttt 900
ctatgagcca aaaaaaaaaa aaaa 924

<210> SEQ ID NO 4
<211> LENGTH: 5422
<212> TYPE: DNA
<213> ORGANISM: Homo sapiens

<400> SEQUENCE: 4
tccgcgtggg gggggtgtgt gcccgccttg cgcatgcgtg ttccctgggc atggccggct 60
ccgttccatc cttctgcaca gggtatcgcc tctctccgtt tggtacatcc cctcctcccc 120
cacgcccgga ctggggtggt agacgccgcc tccgctcatc gcccctcccc atcggtttcc 180
gcgcgaaaag ccggggcgcc tgcgctgccg ccgccgcgtc tgctgaagcc tccgagatgc 240
cggcgcgtac cgccccagcc cgggtgccca cactggccgt cccggccatc tcgctgcccg 300
acgatgtccg caggcggctc aaagatttgg aaagagacag cttaacagaa aaggaatgtg 360
tgaaggagaa attgaatctc ttgcacgaat ttctgcaaac agaaataaag aatcagttat 420
gtgacttgga aaccaaatta cgtaaagaag aattatccga ggagggctac ctggctaaag 480
tcaaatccct tttaaataaa gatttgtcct tggagaacgg tgctcatgct tacaaccggg 540
aagtgaatgg acgtctagaa aacgggaacc aagcaagaag tgaagcccgt agagtgggaa 600
tggcagatgc caacagcccc cccaaacccc tttccaaacc tcgcacgccc aggaggagca 660
agtccgatgg agaggctaag cctgaacctt cacctagccc caggattaca aggaaaagca 720
ccaggcaaac caccatcaca tctcattttg caaagggccc tgccaaacgg aaacctcagg 780
aagagtctga aagagccaaa tcggatgagt ccatcaagga agaagacaaa gaccaggatg 840
agaagagacg tagagttaca tccagagaac gagttgctag accgcttcct gcagaagaac 900
ctgaaagagc aaaatcagga acgcgcactg aaaaggaaga agaaagagat gaaaaagaag 960
aaaagagact ccgaagtcaa accaaagaac caacacccaa acagaaactg aaggaggagc 1020
cggacagaga agccagggca ggcgtgcagg ctgacgagga cgaagatgga gacgagaaag 1080
atgagaagaa gcacagaagt caacccaaag atctagctgc caaacggagg cccgaagaaa 1140
aagaacctga aaaagtaaat ccacagattt ctgatgaaaa agacgaggat gaaaaggagg 1200
agaagagacg caaaacgacc cccaaagaac caacggagaa aaaaatggct cgcgccaaaa 1260
cagtcatgaa ctccaagacc caccctccca agtgcattca gtgcgggcag tacctggacg 1320

-continued

```
accctgacct caaatatggg cagcacccac cagacgcggt ggatgagcca cagatgctga   1380
caaatgagaa gctgtccatc tttgatgcca acgagtctgg ctttgagagt tatgaggcgc   1440
ttccccagca caaactgacc tgcttcagtg tgtactgtaa gcacggtcac ctgtgtccca   1500
tcgacaccgg cctcatcgag aagaatatcg aactcttctt ttctggttca gcaaaaccaa   1560
tctatgatga tgacccatct cttgaaggtg gtgttaatgg caaaaatctt ggccccataa   1620
atgaatggtg gatcactggc tttgatggag gtgaaaaggc cctcatcggc ttcagcacct   1680
catttgccga atacattctg atggatccca gtcccgagta tgcgcccata tttgggctga   1740
tgcaggagaa gatctacatc agcaagattg tggtggagtt cctgcagagc aattccgact   1800
cgacctatga ggacctgatc aacaagatcg agaccacggt tcctccttct ggcctcaact   1860
tgaaccgctt cacagaggac tccctcctgc gacacgcgca gtttgtggtg gagcaggtgg   1920
agagttatga cgaggccggg gacagtgatg agcagcccat cttcctgaca ccctgcatgc   1980
gggacctgat caagctggct ggggtcacgc tgggacagag gcgagcccag gcgaggcggc   2040
agaccatcag gcattctacc agggagaagg acaggggacc cacgaaagcc accaccacca   2100
agctggtcta ccagatcttc gatactttct tcgcagagca aattgaaaag gatgacagag   2160
aagacaagga gaacgccttt aagcgccggc gatgtggcgt ctgtgaggtg tgtcagcagc   2220
ctgagtgtgg gaaatgtaaa gcctgcaagg acatggttaa atttggtggc agtggacgga   2280
gcaagcaggc ttgccaagag cggaggtgtc ccaatatggc catgaaggag gcagatgacg   2340
atgaggaagt cgatgataac atcccagaga tgccgtcacc caaaaaaatg caccagggga   2400
agaagaagaa acagaacaag aatcgcatct cttgggtcgg agaagccgtc aagactgatg   2460
ggaagaagag ttactataag aaggtgtgca ttgatgcgga aaccctggaa gtgggggact   2520
gtgtctctgt tattccagat gattcctcaa aaccgctgta tctagcaagg gtcacggcgc   2580
tgtgggagga cagcagcaac gggcagatgt ttcacgccca ctggttctgc gctgggacag   2640
acacagtcct cggggccacg tcggaccctc tggagctgtt cttggtggat gaatgtgagg   2700
acatgcagct ttcatatatc cacagcaaag tgaaagtcat ctacaaagcc ccctccgaaa   2760
actgggccat ggagggaggc atggatcccg agtccctgct ggagggggac gacgggaaga   2820
cctacttcta ccagctgtgg tatgatcaag actacgcgag attcgagtcc cctccaaaaa   2880
cccagccaac agaggacaac aagttcaaat tctgtgtgag ctgtgcccgt ctggctgaga   2940
tgaggcaaaa agaaatcccc agggtcctgg agcagctcga ggacctggat agccgggtcc   3000
tctactactc agccaccaag aacggcatcc tgtaccgagt tggtgatggt gtgtacctgc   3060
cccctgaggc cttcacgttc aacatcaagc tgtccagtcc cgtgaaacgc ccacggaagg   3120
agcccgtgga tgaggacctg tacccagagc actaccggaa atactccgac tacatcaaag   3180
gcagcaacct ggatgcccct gagccctacc gaattggccg gatcaaagag atcttctgtc   3240
ccaagaagag caacggcagg cccaatgaga ctgacatcaa aatccgggtc aacaagttct   3300
acaggcctga gaacacccac aagtccactc cagcgagcta ccacgcagac atcaacctgc   3360
tctactggag cgacgaggag gccgtggtgg acttcaaggc tgtgcagggc cgctgcaccg   3420
tggagtatgg ggaggacctg cccgagtgcg tccaggtgta ctccatgggc ggccccaacc   3480
gcttctactt cctcgaggcc tataatgcaa agagcaaaag ctttgaagat cctcccaacc   3540
atgcccgtag ccctggaaac aaagggaagg gcaagggaaa agggaagggc aagcccaagt   3600
cccaagcctg tgagccgagc gagccagaga tagagatcaa gctgcccaag ctgcggaccc   3660
tggatgtgtt ttctggctgc ggggggttgt cggagggatt ccaccaagca ggcatctctg   3720
```

```
acacgctgtg ggccatcgag atgtgggacc ctgcggccca ggcgttccgg ctgaacaacc   3780

ccggctccac agtgttcaca gaggactgca acatcctgct gaagctggtc atggctgggg   3840

agaccaccaa ctcccgcggc cagcggctgc cccagaaggg agacgtggag atgctgtgcg   3900

gcgggccgcc ctgccagggc ttcagcggca tgaaccgctt caattcgcgc acctactcca   3960

agttcaaaaa ctctctggtg gtttccttcc tcagctactg cgactactac cggccccggt   4020

tcttcctcct ggagaatgtc aggaactttg tctccttcaa gcgctccatg gtcctgaagc   4080

tcaccctccg ctgcctggtc cgcatgggct atcagtgcac cttcggcgtg ctgcaggccg   4140

gtcagtacgg cgtggcccag actaggaggc gggccatcat cctggccgcg gcccctggag   4200

agaagctccc tctgttcccg gagccactgc acgtgtttgc tccccgggcc tgccagctga   4260

gcgtggtggt ggatgacaag aagtttgtga gcaacataac caggttgagc tcgggtcctt   4320

tccggaccat cacggtgcga gacacgatgt ccgacctgcc ggaggtgcgg aatggagcct   4380

cggcactgga gatctcctac aacggggagc ctcagtcctg gttccagagg cagctccggg   4440

gcgcacagta ccagcccatc ctcagggacc acatctgtaa ggacatgagt gcattggtgg   4500

ctgcccgcat gcggcacatc cccttggccc cagggtcaga ctggcgcgat ctgcccaaca   4560

tcgaggtgcg gctctcagac ggcaccatgg ccaggaagct gcggtatacc caccatgaca   4620

ggaagaacgg ccgcagcagc tctggggccc tccgtggggt ctgctcctgc gtggaagccg   4680

gcaaagcctg cgaccccgca gccaggcagt tcaacaccct catcccctgg tgcctgcccc   4740

acaccgggaa ccggcacaac cactgggctg gcctctatgg aaggctcgag tgggacggct   4800

tcttcagcac aaccgtcacc aaccccgagc ccatgggcaa gcagggccgc gtgctccacc   4860

cagagcagca ccgtgtggtg agcgtgcggg agtgtgcccg ctcccagggc ttccctgaca   4920

cctaccggct cttcggcaac atcctggaca agcaccggca ggtgggcaat gccgtgccac   4980

cgcccctggc caaagccatt ggcttggaga tcaagctttg tatgttggcc aaagcccgag   5040

agagtgcctc agctaaaata aaggaggagg aagctgctaa ggactagttc tgccctcccg   5100

tcacccctgt ttctggcacc aggaatcccc aacatgcact gatgttgtgt ttttaacatg   5160

tcaatctgtc cgttcacatg tgtggtacat ggtgtttgtg gccttggctg acatgaagct   5220

gttgtgtgag gttcgcttat caactaatga tttagtgatc aaattgtgca gtactttgtg   5280

cattctggat tttaaaagtt ttttattatg cattatatca aatctaccac tgtatgagtg   5340

gaaattaaga ctttatgtag tttttatatg ttgtaatatt tcttcaaata aatctctcct   5400

ataaaccacc aaaaaaaaaa aa                                            5422
```

<210> SEQ ID NO 5
<211> LENGTH: 6369
<212> TYPE: DNA
<213> ORGANISM: Homo sapiens

<400> SEQUENCE: 5

```
gtccgggcag cccccggcgc agcgcggccg cagcagcctc cgcccccgc acggtgtgag     60

cgcccgacgc ggccgaggcg gccggagtcc cgagctagcc ccggcggccg ccgccgccca    120

gaccggacga caggccacct cgtcggcgtc cgcccgagtc cccgcctcgc cgccaacgcc    180

acaaccaccg cgcacggccc cctgactccg tccagtattg atcgggagag ccggagcgag    240

ctcttcgggg agcagcgatg cgaccctccg ggacggccgg ggcagcgctc ctggcgctgc    300

tggctgcgct ctgcccggcg agtcgggctc tggaggaaaa gaaagtttgc caaggcacga    360
```

-continued

```
gtaacaagct cacgcagttg ggcacttttg aagatcattt tctcagcctc cagaggatgt    420
tcaataactg tgaggtggtc cttgggaatt tggaaattac ctatgtgcag aggaattatg    480
atctttcctt cttaaagacc atccaggagg tggctggtta tgtcctcatt gccctcaaca    540
cagtggagcg aattcctttg gaaaacctgc agatcatcag aggaaatatg tactacgaaa    600
attcctatgc cttagcagtc ttatctaact atgatgcaaa taaaaccgga ctgaaggagc    660
tgcccatgag aaatttacag gaaatcctgc atggcgccgt gcggttcagc aacaaccctg    720
ccctgtgcaa cgtggagagc atccagtggc gggacatagt cagcagtgac tttctcagca    780
acatgtcgat ggacttccag aaccacctgg gcagctgcca aaagtgtgat ccaagctgtc    840
ccaatgggag ctgctggggt gcaggagagg agaactgcca gaaactgacc aaaatcatct    900
gtgcccagca gtgctccggg cgctgccgtg gcaagtcccc cagtgactgc tgccacaacc    960
agtgtgctgc aggctgcaca ggcccccggg agagcgactg cctggtctgc cgcaaattcc   1020
gagacgaagc cacgtgcaag gacacctgcc ccccactcat gctctacaac cccaccacgt   1080
accagatgga tgtgaacccc gagggcaaat acagctttgg tgccacctgc gtgaagaagt   1140
gtccccgtaa ttatgtggtg acagatcacg gctcgtgcgt ccgagcctgt ggggccgaca   1200
gctatgagat ggaggaagac ggcgtccgca agtgtaagaa gtgcgaaggg ccttgccgca   1260
aagtgtgtaa cggaataggt attggtgaat ttaaagactc actctccata aatgctacga   1320
atattaaaca cttcaaaaac tgcacctcca tcagtggcga tctccacatc ctgccggtgg   1380
catttagggg tgactccttc acacatactc ctcctctgga tccacaggaa ctggatattc   1440
tgaaaaccgt aaaggaaatc acagggtttt tgctgattca ggcttggcct gaaaacagga   1500
cggacctcca tgcctttgag aacctagaaa tcatacgcgg caggaccaag caacatggtc   1560
agttttctct tgcagtcgtc agcctgaaca taacatcctt gggattacgc tccctcaagg   1620
agataagtga tggagatgtg ataatttcag gaaacaaaaa tttgtgctat gcaaatacaa   1680
taaactggaa aaaactgttt gggacctccg gtcagaaaac caaaattata agcaacagag   1740
gtgaaaacag ctgcaaggcc acaggccagg tctgccatgc cttgtgctcc cccgagggct   1800
gctggggccc ggagcccagg gactgcgtct cttgccggaa tgtcagccga ggcagggaat   1860
gcgtggacaa gtgcaacctt ctggagggtg agccaaggga gtttgtggag aactctgagt   1920
gcatacagtg ccacccagag tgcctgcctc aggccatgaa catcacctgc acaggacggg   1980
gaccagacaa ctgtatccag tgtgcccact acattgacgg cccccactgc gtcaagacct   2040
gcccggcagg agtcatggga gaaaacaaca ccctggtctg gaagtacgca gacgccggcc   2100
atgtgtgcca cctgtgccat ccaaactgca cctacggatg cactgggcca ggtcttgaag   2160
gctgtccaac gaatgggcct aagatcccgt ccatcgccac tgggatggtg ggggccctcc   2220
tcttgctgct ggtggtggcc ctggggatcg gcctcttcat gcgaaggcgc cacatcgttc   2280
ggaagcgcac gctgcggagg ctgctgcagg agagggagct tgtggagcct cttacaccca   2340
gtggagaagc tcccaaccaa gctctcttga ggatcttgaa ggaaactgaa ttcaaaaaga   2400
tcaaagtgct gggctccggt gcgttcggca cggtgtataa gggactctgg atcccagaag   2460
gtgagaaagt taaaattccc gtcgctatca aggaattaag agaagcaaca tctccgaaag   2520
ccaacaagga aatcctcgat gaagcctacg tgatggccag cgtggacaac ccccacgtgt   2580
gccgcctgct gggcatctgc ctcacctcca ccgtgcagct catcacgcag ctcatgccct   2640
tcggctgcct cctggactat gtccgggaac acaaagacaa tattggctcc cagtacctgc   2700
tcaactggtg tgtgcagatc gcaaagggca tgaactactt ggaggaccgt cgcttggtgc   2760
```

```
accgcgacct ggcagccagg aacgtactgg tgaaaacacc gcagcatgtc aagatcacag   2820
attttgggct ggccaaactg ctgggtgcgg aagagaaaga ataccatgca gaaggaggca   2880
aagtgcctat caagtggatg gcattggaat caattttaca cagaatctat acccaccaga   2940
gtgatgtctg gagctacggg gtgactgttt gggagttgat gacctttgga tccaagccat   3000
atgacggaat ccctgccagc gagatctcct ccatcctgga gaaaggagaa cgcctccctc   3060
agccacccat atgtaccatc gatgtctaca tgatcatggt caagtgctgg atgatagacg   3120
cagatagtcg cccaaagttc cgtgagttga tcatcgaatt ctccaaaatg gcccgagacc   3180
cccagcgcta ccttgtcatt caggggggatg aaagaatgca tttgccaagt cctacagact   3240
ccaacttcta ccgtgccctg atggatgaag aagacatgga cgacgtggtg gatgccgacg   3300
agtacctcat cccacagcag ggcttcttca gcagcccctc cacgtcacgg actcccctcc   3360
tgagctctct gagtgcaacc agcaacaatt ccaccgtggc ttgcattgat agaaatgggc   3420
tgcaaagctg tcccatcaag gaagacagct tcttgcagcg atacagctca gaccccacag   3480
gcgccttgac tgaggacagc atagacgaca ccttcctccc agtgcctgaa tacataaacc   3540
agtccgttcc caaaaggccc gctggctctg tgcagaatcc tgtctatcac aatcagcctc   3600
tgaaccccgc gcccagcaga gacccacact accaggaccc ccacagcact gcagtgggca   3660
accccgagta tctcaacact gtccagccca cctgtgtcaa cagcacattc gacagccctg   3720
cccactgggc ccagaaaggc agccaccaaa ttagcctgga caaccctgac taccagcagg   3780
acttctttcc caaggaagcc aagccaaatg gcatctttaa gggctccaca gctgaaaatg   3840
cagaatacct aagggtcgcg ccacaaagca gtgaatttat tggagcatga ccacggagga   3900
tagtatgagc cctaaaaatc cagactcttt cgatacccag gaccaagcca cagcaggtcc   3960
tccatcccaa cagccatgcc cgcattagct cttagaccca cagactggtt ttgcaacgtt   4020
tacaccgact agccaggaag tacttccacc tcgggcacat tttgggaagt tgcattcctt   4080
tgtcttcaaa ctgtgaagca tttacagaaa cgcatccagc aagaatattg tccctttgag   4140
cagaaattta tctttcaaag aggtatattt gaaaaaaaaa aaaagtatat gtgaggattt   4200
ttattgattg gggatcttgg agtttttcat tgtcgctatt gatttttact tcaatgggct   4260
cttccaacaa ggaagaagct tgctggtagc acttgctacc ctgagttcat ccaggcccaa   4320
ctgtgagcaa ggagcacaag ccacaagtct tccagaggat gcttgattcc agtggttctg   4380
cttcaaggct tccactgcaa aacactaaag atccaagaag gccttcatgg ccccagcagg   4440
ccggatcggt actgtatcaa gtcatggcag gtacagtagg ataagccact ctgtcccttc   4500
ctgggcaaag aagaaacgga ggggatggaa ttcttcctta gacttacttt tgtaaaaatg   4560
tccccacggt acttactccc cactgatgga ccagtggttt ccagtcatga gcgttagact   4620
gacttgtttg tcttccattc cattgttttg aaactcagta tgctgcccct gtcttgctgt   4680
catgaaatca gcaagagagg atgacacatc aaataataac tcggattcca gcccacattg   4740
gattcatcag catttggacc aatagcccac agctgagaat gtggaatacc taaggatagc   4800
accgcttttg ttctcgcaaa aacgtatctc ctaatttgag gctcagatga aatgcatcag   4860
gtcctttggg gcatagatca gaagactaca aaaatgaagc tgctctgaaa tctcctttag   4920
ccatcacccc aacccccaa aattagtttg tgttacttat ggaagatagt tttctccttt   4980
tacttcactt caaaagcttt ttactcaaag agtatatgtt ccctccaggt cagctgcccc   5040
caaacccct ccttacgctt tgtcacacaa aaagtgtctc tgccttgagt catctattca   5100
```

```
agcacttaca gctctggcca caacagggca ttttacaggt gcgaatgaca gtagcattat   5160

gagtagtgtg gaattcaggt agtaaatatg aaactagggt ttgaaattga taatgctttc   5220

acaacatttg cagatgtttt agaaggaaaa aagttccttc ctaaaataat ttctctacaa   5280

ttggaagatt ggaagattca gctagttagg agcccacctt ttttcctaat ctgtgtgtgc   5340

cctgtaacct gactggttaa cagcagtcct ttgtaaacag tgttttaaac tctcctagtc   5400

aatatccacc ccatccaatt tatcaaggaa gaaatggttc agaaaatatt ttcagcctac   5460

agttatgttc agtcacacac acatacaaaa tgttcctttt gcttttaaag taatttttga   5520

ctcccagatc agtcagagcc cctacagcat tgttaagaaa gtatttgatt tttgtctcaa   5580

tgaaaataaa actatattca tttccactct attatgctct caaatacccc taagcatcta   5640

tactagcctg gtatgggtat gaaagataca aagataaata aaacatagtc cctgattcta   5700

agaaattcac aatttagcaa aggaaatgga ctcatagatg ctaaccttaa aacaacgtga   5760

caaatgccag acaggaccca tcagccaggc actgtgagag cacagagcag ggaggttggg   5820

tcctgcctga ggagacctgg aagggaggcc tcacaggagg atgaccaggt ctcagtcagc   5880

ggggaggtgg aaagtgcagg tgcatcaggg gcaccctgac cgaggaaaca gctgccagag   5940

gcctccactg ctaaagtcca cataaggctg aggtcagtca ccctaaacaa cctgctccct   6000

ctaagccagg ggatgagctt ggagcatccc acaagttccc taaaagttgc agcccccagg   6060

gggattttga gctatcatct ctgcacatgc ttagtgagaa gactacacaa catttctaag   6120

aatctgagat tttatattgt cagttaacca ctttcattat tcattcacct caggacatgc   6180

agaaatattt cagtcagaac tgggaaacag aaggacctac attctgctgt cacttatgtg   6240

tcaagaagca gatgatcgat gaggcaggtc agttgtaagt gagtcacatt gtagcattaa   6300

attctagtat ttttgtagtt tgaaacagta acttaataaa agagcaaaag ctaaaaaaaa   6360

aaaaaaaaa                                                           6369
```

<210> SEQ ID NO 6
<211> LENGTH: 3278
<212> TYPE: DNA
<213> ORGANISM: Homo sapiens

<400> SEQUENCE: 6

```
aatagactaa acccagagcc tcaaagcagt gcactccgtg aaggcaaaga gaacacgctg     60

caaaaggctt tccaagaatc ctcgacatgg caaggaggag ctcgttccag tcgtgtcaga    120

taatatccct gttcactttt gccgttggag tcaatatctg cttaggattc actgcacatc    180

gaattaagag agcagaagga tgggaggaag gtcctcctac agtgctatca gactccccct    240

ggaccaacat ctccggatct tgcaagggca ggtgctttga acttcaagag gctggacctc    300

ctgattgtcg ctgtgacaac ttgtgtaaga gctataccag ttgctgccat gactttgatg    360

agctgtgttt gaagacagcc cgtggctggg agtgtactaa ggacagatgt ggagaagtca    420

gaaatgaaga aaatgcctgt cactgctcag aggactgctt ggccagggga gactgctgta    480

ccaattacca agtggtttgc aaaggagagt cgcattgggt tgatgatgac tgtgaggaaa    540

taaaggccgc agaatgccct gcagggtttg ttcgccctcc attaatcatc ttctccgtgg    600

atggcttccg tgcatcatac atgaagaaag gcagcaaagt catgcctaat attgaaaaac    660

taaggtcttg tggcacacac tctccctaca tgaggccggt gtacccaact aaaacctttc    720

ctaacttata cactttggcc actgggctat atccagaatc acatggaatt gttggcaatt    780

caatgtatga tcctgtattt gatgccactt ttcatctgcg agggcgagag aaatttaatc    840
```

```
atagatggtg gggaggtcaa ccgctatgga ttacagccac caagcaaggg gtgaaagctg    900
gaacattctt ttggtctgtt gtcatccctc acgagcggag aatattaacc atattgcagt    960
ggctcaccct gccagatcat gagaggcctt cggtctatgc cttctattct gagcaacctg   1020
atttctctgg acacaaatat ggccctttcg gccctgagga gagtagttat ggctcacctt   1080
ttactccggc taagagacct aagaggaaag ttgcccctaa gaggagacag gaaagaccag   1140
ttgctcctcc aaagaaaaga agaagaaaaa tacataggat ggatcattat gctgcggaaa   1200
ctcgtcagga caaaatgaca aatcctctga gggaaatcga caaaattgtg gggcaattaa   1260
tggatggact gaaacaacta aaactgcatc ggtgtgtcaa cgtcatcttt gtcggagacc   1320
atggaatgga agatgtcaca tgtgatagaa ctgagttctt gagtaattac ctaactaatg   1380
tggatgatat tactttagtg cctggaactc taggaagaat tcgatccaaa tttagcaaca   1440
atgctaaata tgaccccaaa gccattattg ccaatctcac gtgtaaaaaa ccagatcagc   1500
actttaagcc ttacttgaaa cagcaccttc ccaaacgttt gcactatgcc aacaacagaa   1560
gaattgagga tatccattta ttggtggaac gcagatggca tgttgcaagg aaacctttgg   1620
atgtttataa gaaaccatca ggaaaatgct ttttccaggg agaccacgga tttgataaca   1680
aggtcaacag catgcagact gtttttgtag gttatggctc aacatttaag tacaagacta   1740
aagtgcctcc atttgaaaac attgaacttt acaatgttat gtgtgatctc ctgggattga   1800
agccagctcc taataatggg acccatggaa gtttgaatca tctcctgcgc actaatacct   1860
tcaggccaac catgccagag gaagttacca gacccaatta tccagggatt atgtaccttc   1920
agtctgattt tgacctgggc tgcacttgtg atgataaggt agagccaaag aacaagttgg   1980
atgaactcaa caaacggctt catacaaaag ggtctacaga agagagacac ctcctctatg   2040
ggcgacctgc agtgctttat cggactagat atgatatctt atatcacact gactttgaaa   2100
gtggttatag tgaaatattc ctaatgccac tctggacatc atatactgtt tccaaacagg   2160
ctgaggtttc cagcgttcct gaccatctga ccagttgcgt ccggcctgat gtccgtgttt   2220
ctccgagttt cagtcagaac tgtttggcct acaaaaatga taagcagatg tcctacggat   2280
tcctctttcc tccttatctg agctcttcac cagaggctaa atatgatgca ttccttgtaa   2340
ccaatatggt tccaatgtat cctgctttca aacgggtctg gaattatttc caaagggtat   2400
tggtgaagaa atatgcttcg gaaagaaatg gagttaacgt gataagtgga ccaatcttcg   2460
actatgacta tgatggctta catgacacag aagacaaaat aaaacagtac gtggaaggca   2520
gttccattcc tgttccaact cactactaca gcatcatcac cagctgtctg gatttcactc   2580
agcctgccga caagtgtgac ggccctctct ctgtgtcctc cttcatcctg cctcaccggc   2640
ctgacaacga ggagagctgc aatagctcag aggacgaatc aaaatgggta gaagaactca   2700
tgaagatgca cacagctagg gtgcgtgaca ttgaacatct caccagcctg gacttcttcc   2760
gaaagaccag ccgcagctac ccagaaatcc tgacactcaa gacatacctg catacatatg   2820
agagcgagat ttaactttct gagcatctgc agtacagtct tatcaactgg ttgtatattt   2880
ttatattgtt tttgtattta ttaatttgaa accaggacat taaaaatgtt agtattttaa   2940
tcctgtacca aatctgacat attatgcctg aatgactcca ctgtttttct ctaatgcttg   3000
atttaggtag ccttgtgttc tgagtagagc ttgtaataaa tactgcagct tgagttttta   3060
gtggaagctt ctaaatggtg ctgcagattt gatatttgca ttgaggaaat attaattttc   3120
caatgcacag ttgccacatt tagtcctgta ctgtatggaa acactgattt tgtaaagttg   3180
```

```
cctttatttg ctgttaactg ttaactatga cagatatatt taagccttat aaaccaatct   3240

taaacataat aaatcacaca ttcagttttt tctggttt                           3278


<210> SEQ ID NO 7
<211> LENGTH: 3172
<212> TYPE: DNA
<213> ORGANISM: Homo sapiens

<400> SEQUENCE: 7

agtgctgggc ggggcgctga ctcacccggg cccgggctgg ccggttctta agcggcagcg     60

cgctgcgggc gccgagtgtc gggcgcggca ggaggacgag gcagggcggg cgggcgctct    120

aagggttctg ctctgactcc aggttgggac agcgtcttcg ctgctgctgg atagtcgtgt    180

tttcggggat cgaggatact caccagaaac cgaaaatgcc gaaaccaatc aatgtccgag    240

ttaccaccat ggatgcagag ctggagtttg caatccagcc aaatacaact ggaaaacagc    300

tttttgatca ggtggtaaag actatcggcc tccgggaagt gtggtacttt ggcctccact    360

atgtggataa taaaggattt cctacctggc tgaagctgga taagaaggtg tctgcccagg    420

aggtcaggaa ggagaatccc ctccagttca agttccgggc caagttctac cctgaagatg    480

tggctgagga gctcatccag gacatcaccc agaaactttt cttcctccaa gtgaaggaag    540

gaatccttag cgatgagatc tactgccccc ctgagactgc cgtgctcttg ggtcctacg    600

ctgtgcaggc caagtttggg gactacaaca aagaagtgca caagtctggg tacctcagct    660

ctgagcggct gatccctcaa agagtgatgg accagcacaa acttaccagg gaccagtggg    720

aggaccggat ccaggtgtgg catgcggaac accgtgggat gctcaaagat aatgctatgt    780

tggaatacct gaagattgct caggacctgg aaatgtatgg aatcaactat ttcgagataa    840

aaaacaagaa aggaacagac ctttggcttg gagttgatgc ccttggactg aatatttatg    900

agaaagatga taagttaacc ccaaagattg gctttccttg gagtgaaatc aggaacatct    960

ctttcaatga caaaaagttt gtcattaaac ccatcgacaa gaaggcacct gactttgtgt   1020

tttatgcccc acgtctgaga atcaacaagc ggatcctgca gctctgcatg ggcaaccatg   1080

agttgtatat gcgccgcagg aagcctgaca ccatcgaggt gcagcagatg aaggcccagg   1140

cccgggagga gaagcatcag aagcagctgg agcggcaaca gctggaaaca gagaagaaaa   1200

ggagagaaac cgtggagaga gagaaagagc agatgatgcg cgagaaggag gagttgatgc   1260

tgcggctgca ggactatgag gagaagacaa agaaggcaga gagagagctc tcggagcaga   1320

ttcagagggc cctgcagctg gaggaggaga ggaagcgggc acaggaggag gccgagcgcc   1380

tagaggctga ccgtatggct gcactgcggg ctaaggagga gctggagaga caggcggtgg   1440

atcagataaa gagccaggag cagctggctg cggagcttgc agaatacact gccaagattg   1500

ccctcctgga agaggcgcgg aggcgcaagg aggatgaagt tgaagagtgg cagcacaggg   1560

ccaaagaagc ccaggatgac ctggtgaaga ccaaggagga gctgcacctg gtgatgacag   1620

cacccccgcc cccaccaccc cccgtgtacg agccggtgag ctaccatgtc caggagagct   1680

tgcaggatga gggcgcagag cccacgggct acagcgcgga gctgtctagt gagggcatcc   1740

gggatgaccg caatgaggag aagcgcatca ctgaggcaga gaagaacgag cgtgtgcagc   1800

ggcagctgct gacgctgagc agcgagctgt cccaggcccg agatgagaat aagaggaccc   1860

acaatgacat catccacaac gagaacatga ggcaaggccg ggacaagtac aagacgctgc   1920

ggcagatccg gcagggcaac accaagcagc gcatcgacga gttcgaggcc ctgtaacagc   1980

caggccagga ccaagggcag aggggtgctc atagcgggcg ctgccagccc cgccacgctt   2040
```

```
gtgtctttag tgctccaagt ctaggaactc cctcagatcc cagttccttt agaaagcagt   2100

tacccaacag aaacattctg ggctgggaac caggaggcg ccctggtttg ttttccccag   2160

ttgtaatagt gccaagcagg cctgattctc gcgattattc tcgaatcacc tcctgtgttg   2220

tgctgggagc aggactgatt gaattacgga aaatgcctgt aaagtctgag taagaaactt   2280

catgctggcc tgtgtgatac aagagtcagc atcattaaag gaaacgtggc aggacttcca   2340

tctgtgccat acttgttctg tattcgaaat gagctcaaat tgatttttta atttctatga   2400

aggatccatc tttgtatatt tacatgctta gaggggtgaa aattattttg gaaattgagt   2460

ctgaagcact ctcgcacaca cagtgattcc ctcctcccgt cactccacgc agctggcaga   2520

gagcacagtg atcaccagcg tgagtggtgg aggaggacac ttggattttt tttttgttt    2580

ttttttttt tgcttaacag ttttagaata cattgtactt atacacctta ttaatgatca    2640

gctatatact atttatatac aagtgataat acagatttgt aacattagtt ttaaaaaggg   2700

aaagttttgt tctgtatatt ttgttacctt ttacagaata aaagaattac atatgaaaaa   2760

ccctctaaac catggcactt gatgtgatgt ggcaggaggg cagtggtgga gctggacctg   2820

cctgctgcag tcacgtgtaa acaggattat tattagtgtt ttatgcatgt aatggactat   2880

gcacactttt aattttgtca gattcacaca tgccactatg agctttcaga ctccagctgt   2940

gaagagactc tgtttgcttg tgtttgtttg tttgcagtct ctctctgcca tggccttggc   3000

aggctgctgg aaggcagctt gtggaggccg ttggttccgc ccactcattc cttctcgtgc   3060

actgctttct ccttcacagc taagatgcca tgtgcaggtg gattccatgc cgcagacatg   3120

aaataaaagc tttgcaaagg cacgaagcaa aaaaaaaaaa aaaaaaaaaa aa           3172
```

<210> SEQ ID NO 8
<211> LENGTH: 1907
<212> TYPE: DNA
<213> ORGANISM: Homo sapiens

<400> SEQUENCE: 8

```
agaatcagag agagagagat agagaaagag aaagacagag gtgtttccct tagctatgga     60

aactctataa gagagatcca gcttgcctcc tcttgagcag tcagcaacag ggtcccgtcc    120

ttgacacctc agcctctaca ggactgagaa gaagtaaaac cgtttgctgg ggctggcctg    180

actcaccagc tgccatgcag cagcccttca attacccata tccccagatc tactgggtgg    240

acagcagtgc cagctctccc tgggcccctc caggcacagt tcttccctgt ccaacctctg    300

tgcccagaag gcctggtcaa aggaggccac caccaccacc gccaccgcca ccactaccac    360

ctccgccgcc gccgccacca ctgcctccac taccgctgcc acccctgaag aagagaggga    420

accacagcac aggcctgtgt ctccttgtga tgtttttcat ggttctggtt gccttggtag    480

gattgggcct ggggatgttt cagctcttcc acctacagaa ggagctggca gaactccgag    540

agtctaccag ccagatgcac acagcatcat ctttggagaa gcaaataggc caccccagtc    600

cacccccctga aaaaaaggag ctgaggaaag tggcccattt aacaggcaag tccaactcaa   660

ggtccatgcc tctggaatgg gaagacacct atggaattgt cctgctttct ggagtgaagt    720

ataagaaggg tggccttgtg atcaatgaaa ctgggctgta ctttgtatat tccaaagtat    780

acttccgggg tcaatcttgc aacaacctgc ccctgagcca caaggtctac atgaggaact    840

ctaagtatcc ccaggatctg gtgatgatgg aggggaagat gatgagctac tgcactactg    900

ggcagatgtg ggcccgcagc agctacctgg gggcagtgtt caatcttacc agtgctgatc    960
```

```
atttatatgt caacgtatct gagctctctc tggtcaattt tgaggaatct cagacgtttt   1020
tcggcttata taagctctaa gagaagcact ttgggattct ttccattatg attctttgtt   1080
acaggcaccg agaatgttgt attcagtgag ggtcttctta catgcatttg aggtcaagta   1140
agaagacatg aaccaagtgg accttgagac cacagggttc aaaatgtctg tagctcctca   1200
actcacctaa tgtttatgag ccagacaaat ggaggaatat gacggaagaa catagaactc   1260
tgggctgcca tgtgaagagg gagaagcatg aaaaagcagc taccaggtgt tctacactca   1320
tcttagtgcc tgagagtatt taggcagatt gaaaaggaca ccttttaact cacctctcaa   1380
ggtgggcctt gctacctcaa gggggactgt ctttcagata catggttgtg acctgaggat   1440
ttaagggatg gaaaaggaag actagaggct tgcataataa gctaaagagg ctgaaagagg   1500
ccaatgcccc actggcagca tcttcacttc taaatgcata tcctgagcca tcggtgaaac   1560
taacagataa gcaagagaga tgttttgggg actcatttca ttcctaacac agcatgtgta   1620
tttccagtgc aattgtaggg gtgtgtgtgt gtgtgtgtgt gtgtgtgtgt gtatgactaa   1680
agagagaatg tagatattgt gaagtacata ttaggaaaat atgggttgca tttggtcaag   1740
attttgaatg cttcctgaca atcaactcta atagtgctta aaaatcattg attgtcagct   1800
actaatgatg ttttcctata atataataaa tatttatgta gatgtgcatt tttgtgaaat   1860
gaaaacatgt aataaaaagt atatgttagg atacaaaaaa aaaaaaa                 1907
```

<210> SEQ ID NO 9
<211> LENGTH: 2084
<212> TYPE: DNA
<213> ORGANISM: Homo sapiens

<400> SEQUENCE: 9

```
aagacacatg cttctgcaag cttccatgaa ggttgtgcaa aaaagtttca atccagagtt     60
gggttccagc tttctgtagc tgtaagcatt ggtggccaca ccacctcctt acaaagcaac    120
tagaacctgc ggcatacatt ggagagattt ttttaatttt ctggacatga agtaaattta    180
gagtgctttc taatttcagg tagaagacat gtccaccttc tgattatttt tggagaacat    240
tttgattttt ttcatctctc tctccccacc cctaagattg tgcaaaaaaa gcgtaccttg    300
cctaattgaa ataatttcat tggattttga tcagaactga ttatttggtt ttctgtgtga    360
agttttgagg tttcaaactt tccttctgga gaatgccttt tgaaacaatt ttctctagct    420
gcctgatgtc aactgcttag taatcagtgg atattgaaat attcaaaatg tacagagagt    480
gggtagtggt gaatgttttc atgatgttgt acgtccagct ggtgcagggc tccagtaatg    540
aacatggacc agtgaagcga tcatctcagt ccacattgga acgatctgaa cagcagatca    600
gggctgcttc tagtttggag gaactacttc gaattactca ctctgaggac tggaagctgt    660
ggagatgcag gctgaggctc aaaagtttta ccagtatgga ctctcgctca gcatcccatc    720
ggtccactag gtttgcggca actttctatg acattgaaac actaaaagtt atagatgaag    780
aatggcaaag aactcagtgc agccctagag aaacgtgcgt ggaggtggcc agtgagctgg    840
ggaagagtac caacacattc ttcaagcccc cttgtgtgaa cgtgttccga tgtggtggct    900
gttgcaatga agagagcctt atctgtatga acaccagcac ctcgtacatt tccaaacagc    960
tctttgagat atcagtgcct ttgacatcag tacctgaatt agtgcctgtt aaagttgcca   1020
atcatacagg ttgtaagtgc ttgccaacag ccccccgcca tccatactca attatcagaa   1080
gatccatcca gatccctgaa gaagatcgct gttcccattc caagaaactc tgtcctattg   1140
acatgctatg ggatagcaac aaatgtaaat gtgttttgca ggaggaaaat ccacttgctg   1200
```

```
gaacagaaga ccactctcat ctccaggaac cagctctctg tgggccacac atgatgtttg   1260

acgaagatcg ttgcgagtgt gtctgtaaaa caccatgtcc caaagatcta atccagcacc   1320

ccaaaaactg cagttgcttt gagtgcaaag aaagtctgga gacctgctgc cagaagcaca   1380

agctatttca cccagacacc tgcagctgtg aggacagatg cccctttcat accagaccat   1440

gtgcaagtgg caaaacagca tgtgcaaagc attgccgctt tccaaaggag aaaagggctg   1500

cccaggggcc ccacagccga aagaatcctt gattcagcgt tccaagttcc ccatccctgt   1560

catttttaac agcatgctgc tttgccaagt tgctgtcact gttttttttcc caggtgttaa   1620

aaaaaaaatc cattttacac agcaccacag tgaatccaga ccaaccttcc attcacacca   1680

gctaaggagt ccctggttca ttgatggatg tcttctagct gcagatgcct ctgcgcacca   1740

aggaatggag aggaggggac ccatgtaatc cttttgttta gttttgtttt tgtttttttgg   1800

tgaatgagaa aggtgtgctg gtcatggaat ggcaggtgtc atatgactga ttactcagag   1860

cagatgagga aaactgtagt ctctgagtcc tttgctaatc gcaactcttg tgaattattc   1920

tgattctttt ttatgcagaa tttgattcgt atgatcagta ctgactttct gattactgtc   1980

cagcttatag tcttccagtt taatgaacta ccatctgatg tttcatattt aagtgtattt   2040

aaagaaaata aacaccatta ttcaagccat ataaaaaaaa aaaa                    2084
```

<210> SEQ ID NO 10
<211> LENGTH: 1661
<212> TYPE: DNA
<213> ORGANISM: Homo sapiens

<400> SEQUENCE: 10

```
attgcattcc tgggcattgc taactagtga agtataccag atggaaatgt cttcgaagct     60

gtccctttaa aactcgagca agctaccagg caaactccgc ctccagggag gttccttatt    120

aaataggagc caactggctg ggtcggggct caataccccca agcaatacct gcaactgagg    180

attcttcccg gggagaccgc agcccatcgg catggctcaa gagtttgtga actgcaaaat    240

ccagcctggg aaggtggttg tgttcatcaa gcccacctgc ccgtactgca ggagggccca    300

agagatcctc agtcaattgc ccatcaaaca agggcttctg gaatttgtcg atatcacagc    360

caccaaccac actaacgaga ttcaagatta tttgcaacag ctcacgggag caagaacggt    420

gcctcgagtc tttattggta aagattgtat aggcggatgc agtgatctag tctctttgca    480

acagagtggg gaactgctga cgcggctaaa gcagattgga gctctgcagt aaccacagaa    540

caggccccat gctgacgtcc ctcctcaaga gctggatggc attgcaaatg atgacagcac    600

ttctggtgga tgaatttggg ggcacaaaca gcttttttcc tcttttggct cagtatttaa    660

aagtggacca acttgctctt aatcacaggg ccaagaaggt tgacgggcca tcttggtttt    720

cttctggatg tgctctttgg ttttcagaag actgtgacaa gttctggccc aggattcgct    780

cactgaccct caattgtcct ctttggcatg cgtttcttac tgttctccat gtgtcggcat    840

gtctctacct ctaagccagt gtttttcaac tatgtttatc cagactcctt ctccacaatg    900

atgaatccac agttggttat ctgctactgc ccattagcta aaatcatttt gctgcttgac    960

tttatggagt ttgtattatg aaatcagtgg gtattttgaa tgtgttcttt ctaactacat   1020

gcatctctcc actcaactcc accccatccc atcccacctt gaaaatcact gctctgaacc   1080

agtgttctcc accttgtcct ccacagatct cataggaaat gttcaacaat tctgtgaaag   1140

gtcacaggac ccaattggag aaatcatatg aaaagcatag ttggtcttgg tgtcatatgg   1200
```

```
atcagaggca caagtgcaga ggctgtggtc atgcggaaca ctctgttatt taagatggct   1260
atccagataa tcctgaacac tgtgtattta ttttatttag actaccagca aagattaaag   1320
catgaaatgt aaaacatctg ataaaactta cagcccccta caccaagagt gtatctgtga   1380
aagagctcct acactttgaa aacttaagaa tcccttatca tgaagtttgc ctgttctaga   1440
attgtaagat tgttaatttc cttcaatctc tagtgacaac acttaatttc ttttctaata   1500
aaaaaaacct atagatgatt cagtgatttt tgtccaattc atttgcatgt tctcaagaca   1560
ttaaggaatg ttatgcgaaa tacactaact taaaactgtg tttatatttg gccctgccat   1620
tataaataaa gacacgtgct gctgtcaaaa aaaaaaaaaa a                        1661
```

<210> SEQ ID NO 11
<211> LENGTH: 822
<212> TYPE: DNA
<213> ORGANISM: Homo sapiens

<400> SEQUENCE: 11

```
agttccctat cactctcttt aatcactact cacagtaacc tcaactcctg ccacaatgta     60
caggatgcaa ctcctgtctt gcattgcact aagtcttgca cttgtcacaa acagtgcacc    120
tacttcaagt tctacaaaga aaacacagct acaactggag catttactgc tggatttaca    180
gatgattttg aatggaatta ataattacaa gaatcccaaa ctcaccagga tgctcacatt    240
taagttttac atgcccaaga aggccacaga actgaaacat cttcagtgtc tagaagaaga    300
actcaaacct ctggaggaag tgctaaattt agctcaaagc aaaaactttc acttaagacc    360
cagggactta atcagcaata tcaacgtaat agttctggaa ctaaagggat ctgaaacaac    420
attcatgtgt gaatatgctg atgagacagc aaccattgta gaatttctga acagatggat    480
taccttttgt caaagcatca tctcaacact gacttgataa ttaagtgctt cccacttaaa    540
acatatcagg ccttctattt atttaaatat ttaaatttta tatttattgt tgaatgtatg    600
gtttgctacc tattgtaact attattctta atcttaaaac tataaatatg gatcttttat    660
gattcttttt gtaagcccta ggggctctaa aatggtttca cttatttatc ccaaaatatt    720
tattattatg ttgaatgtta aatatagtat ctatgtagat tggttagtaa aactatttaa    780
taaatttgat aaatataaaa aaaaaaaaaa aaaaaaaaaa aa                       822
```

<210> SEQ ID NO 12
<211> LENGTH: 2183
<212> TYPE: DNA
<213> ORGANISM: Homo sapiens

<400> SEQUENCE: 12

```
tcagcactcc accaaagcct ctgcctcagc cttactgtga gtctggttga cagtagcttc     60
taagatgtcc cagcaacaca cactgccagt gaccctctcc cctgccctca gtcaggagct    120
cctcaagact gttcctcctc cagtcaatac ccatcaggag caaatgaaac agccaactcc    180
actgcctccc ccatgccaga aggtgcctgt cgagctccca gtggaggtcc catcaaagca    240
agaggaaaag cacatgactg ctgtaaaggg actgcctgag caagaatgtg agcaacagca    300
gaaggagcca caggagcagg agctgcagca acagcactgg gaacagcatg aggaatatca    360
gaaagcagaa aacccagagc agcagcttaa gcaggagaaa acacaaaggg atcagcagct    420
aaacaaacag ctggaagaag agaagaagct cttagaccag caactggatc aagagctagt    480
caagagagat gagcaactgg gaatgaagaa agagcaactg ttggagctcc cagagcagca    540
ggagggggcac ctgaagcacc tagagcagca ggagggacag ctgaagcacc cggagcagca    600
```

```
ggaggggcag ctggagctcc cagagcagca ggaggggcag ctggagctcc cagagcagca    660
ggaggggcag ctggagctcc cagagcagca ggaggggcag ctggagctcc cagagcagca    720
ggaggggcag ctggagctcc cagagcagca ggaggggcag ctggagctcc cacagcagca    780
ggaggggcag ctggagctct ctgagcagca ggaggggcag ctggagctct ctgagcagca    840
ggagggacag ctgaagcacc tggagcacca ggaggggcag ctggaggtcc cagaggagca    900
gatggggcag ctgaagtacc tggaacagca ggaggggcag ctgaagcacc tggatcagca    960
ggagaagcag ccagagctcc cagagcagca gatggggcag ctgaagcacc tggagcagca   1020
ggaggggcag cctaagcatc tggagcagca ggaggggcaa ctggagcagc tggaggagca   1080
ggaggggcag ctgaagcacc tggagcagca ggaggggcag ctggagcacc tggagcacca   1140
ggaagggcag ctggggctcc cagagcagca ggtgctgcag ctgaagcagc tagagaagca   1200
gcaggggcag ccaaagcacc tggaggagga ggaggggcag ctgaagcacc tggtgcagca   1260
ggaggggcag ctgaagcatc tggtgcagca ggaggggcag ctggagcagc aggagaggca   1320
ggtggagcac ctggagcagc aggtggggca gctgaagcac ctagaggagc aggagggaca   1380
actgaagcat ctggagcagc agcaggggca gttggaggtc ccagagcagc aggtggggca   1440
gccaaagaac ctggagcagg aggagaagca actggagctc ccagagcagc aagagggcca   1500
ggtgaagcac ctggagaagc aggaggcaca gctggagctc ccagagcagc aggtaggaca   1560
gccaaagcac ctggaacagc aggaaaagca cctagagcac ccagagcagc aggacggaca   1620
actaaaacat ctggagcagc aggaggggca gctgaaggac ctggagcagc agaaggggca   1680
gctggagcag cctgtgtttg ccccagctcc aggccaggtc caagacattc aaccagccct   1740
gcccacaaag ggagaagtat tgcttcctgt agagcaccag cagcagaagc aggaggtgca   1800
gtggccaccc aaacataaat aaccacccgc agtgtccaga ggccctcaga tcgtctcata   1860
caagggaaga gagagccact ggctccactt atttcgggtc cgctaggtgg cccgtctcat   1920
ctgtgaactt gactctgtcc ctctacatgt ctctttaatg gggtgagggt gggggagaga   1980
gggaattatt gtccagtgcc aaccccaatg accccaatcc caacctcagg tgagcagagc   2040
ctctacttga gggactattg ttactatagg aatccttact tccccagtat tgaagctgaa   2100
tcagtgagtg tgtacaatga tacataataa atcctggaag tcttgggatc ctaaaaaaaa   2160
aaaaaaaaaa aaaaaaaaaa aaa                                           2183
```

<210> SEQ ID NO 13
<211> LENGTH: 1229
<212> TYPE: DNA
<213> ORGANISM: Homo sapiens

<400> SEQUENCE: 13

```
ctctcctcac tcacccttcc tggtgctttg ggctctcctt ccttctcaga caagatgtct     60
tatcagaaaa agcagcccac ccctcagccc ccagtggact gcgtgaagac ctctggcggc    120
ggtggcggtg gcggcggcag cggcggtggt ggctgcggct tcttcggcgg cggcggctca    180
gggggcggta gcagcggttc tggctgcggc tactccggcg gcggtggcta ctctggcggc    240
ggctgcggcg gggctcctc cggcggcggg ggcgggggcg gcattggagg ctgcggaggg     300
ggctccggtg ggagcgtcaa gtactccgga ggcggcggct cctccggcgg gggctctggc    360
tgtttctcca gcggtggggg cggctccggc tgcttctcct ccggtggcgg cggctcctcc    420
gggggcggct ccggctgctt ctccagcggt gggggcggct cctccggggg cggctccggc    480
```

```
tgcttctcct ccggcggcgg cggcttctcg ggccaggcgg tccagtgcca gagctacgga    540

ggcgtctcta gcggcggctc ctccgggggc ggctccggct gcttctccag cggcgggggc    600

ggcggctctg tctgcggcta ctctggcggc ggctctggct gcggcggagg ctcctctggc    660

ggcagcggct ccggctacgt ctcctcgcag caggtcactc agacctcgtg cgcgccccag    720

ccgagttacg gaggggggtc gtccggcggc ggcggcagcg gcggaagcgg ctgcttctcc    780

agcggcgggg gcggcgggag ctccggctgc ggcggcggct cctccgggat tggcagcggc    840

tgcatcatca gtggcggggg ctccgtctgc ggaggtggtt cctctggagg cggcggcggc    900

ggctcctccg tgggtggctc cgggagtggc aagggcgtcc cgatctgcca ccagacccag    960

cagaagcagg cgcctacctg gccgtccaaa tagatccccc agggtaccac ggaggcgaag   1020

gagttggagg tgttttccag gggcaccgat gggcttagag ctctcatgat gctacccgag   1080

gtttgcaaat ccttcatgtc ttaacctacc tggaagaagc cattgagctc tccggctgca   1140

tctagttctg ctgtttagcc tctttggttt ctgtacaact acctcccaac cccagtgcct   1200

cagtcaataa atttgcaaat tcatgagaa                                     1229
```

```
<210> SEQ ID NO 14
<211> LENGTH: 2081
<212> TYPE: DNA
<213> ORGANISM: Homo sapiens

<400> SEQUENCE: 14

agcatgagtc agacagcctc tggctttctg gaagggcaag gactctatat atacagaggg     60

agcttcctag ctgggatatt ggagcagcaa gaggctggga agccatcact taccttgcac    120

tgagaaagaa gacaaaggcc agtatgcaca gctttcctcc actgctgctg ctgctgttct    180

ggggtgtggt gtctcacagc ttcccagcga ctctagaaac acaagagcaa gatgtggact    240

tagtccagaa atacctggaa aaatactaca acctgaagaa tgatgggagg caagttgaaa    300

agcggagaaa tagtggccca gtggttgaaa aattgaagca aatgcaggaa ttctttgggc    360

tgaaagtgac tgggaaacca gatgctgaaa ccctgaaggt gatgaagcag cccagatgtg    420

gagtgcctga tgtggctcag tttgtcctca ctgaggggaa ccctcgctgg gagcaaacac    480

atctgaccta caggattgaa aattacacgc cagatttgcc aagagcagat gtggaccatg    540

ccattgagaa agccttccaa ctctggagta atgtcacacc tctgacattc accaaggtct    600

ctgagggtca agcagacatc atgatatctt ttgtcagggg agatcatcgg gacaactctc    660

cttttgatgg acctggagga aatcttgctc atgcttttca accaggccca ggtattggag    720

gggatgctca ttttgatgaa gatgaaaggt ggaccaacaa tttcagagag tacaacttac    780

atcgtgttgc agctcatgaa ctcggccatt ctcttggact ctcccattct actgatatcg    840

gggctttgat gtaccctagc tacaccttca gtggtgatgt tcagctagct caggatgaca    900

ttgatggcat ccaagccata tatggacgtt cccaaaatcc tgtccagccc atcggcccac    960

aaaccccaaa agcgtgtgac agtaagctaa cctttgatgc tataactacg attcggggag   1020

aagtgatgtt ctttaaagac agattctaca tgcgcacaaa tcccttctac ccggaagttg   1080

agctcaattt catttctgtt ttctggccac aactgccaaa tgggcttgaa gctgcttacg   1140

aatttgccga cagagatgaa gtccggtttt tcaaagggaa taagtactgg gctgttcagg   1200

gacagaatgt gctacacgga taccccaagg acatctacag ctcctttggc ttccctagaa   1260

ctgtgaagca tatcgatgct gctctttctg aggaaaacac tggaaaaacc tacttctttg   1320

ttgctaacaa atactggagg tatgatgaat ataaacgatc tatggatcca ggttatccca   1380
```

```
aaatgatagc acatgacttt cctggaattg gccacaaagt tgatgcagtt ttcatgaaag   1440

atggattttt ctatttcttt catggaacaa gacaatacaa atttgatcct aaaacgaaga   1500

gaattttgac tctccagaaa gctaatagct ggttcaactg caggaaaaat tgaacattac   1560

taatttgaat ggaaaacaca tggtgtgagt ccaaagaagg tgttttcctg aagaactgtc   1620

tattttctca gtcattttta acctctagag tcactgatac acagaatata atcttattta   1680

tacctcagtt tgcatatttt tttactattt agaatgtagc ccttttgta ctgatataat    1740

ttagttccac aaatggtggg tacaaaaagt caagtttgtg gcttatggat tcatataggc   1800

cagagttgca aagatctttt ccagagtatg caactctgac gttgatccca gagagcagct   1860

tcagtgacaa acatatcctt tcaagacaga aagagacagg agacatgagt ctttgccgga   1920

ggaaaagcag ctcaagaaca catgtgcagt cactggtgtc accctggata ggcaagggat   1980

aactcttcta acacaaaata agtgttttat gtttggaata aagtcaacct tgtttctact   2040

gttttataca ctttcaaaaa aaaaaaaaaa aaaaaaaaaa a                        2081
```

<210> SEQ ID NO 15
<211> LENGTH: 1906
<212> TYPE: DNA
<213> ORGANISM: Homo sapiens

<400> SEQUENCE: 15

```
aaagcaagga tgagtcaagc tgcgggtgat ccaaacaaac actgtcactc tttaaaagct     60

gcgctcccga ggttggacct acaaggaggc aggcaagaca gcaaggcata gagacaacat    120

agagctaagt aaagccagtg gaaatgaaga gtcttccaat cctactgttg ctgtgcgtgg    180

cagtttgctc agcctatcca ttggatggag ctgcaagggg tgaggacacc agcatgaacc    240

ttgttcagaa atatctagaa aactactacg acctcaaaaa agatgtgaaa cagtttgtta    300

ggagaaagga cagtggtcct gttgttaaaa aaatccgaga aatgcagaag ttccttggat    360

tggaggtgac ggggaagctg gactccgaca ctctggaggt gatgcgcaag cccaggtgtg    420

gagttcctga tgttggtcac ttcagaacct ttcctggcat cccgaagtgg aggaaaaccc    480

accttacata caggattgtg aattatacac cagatttgcc aaaagatgct gttgattctg    540

ctgttgagaa agctctgaaa gtctgggaag aggtgactcc actcacattc tccaggctgt    600

atgaaggaga ggctgatata atgatctctt ttgcagttag agaacatgga gacttttacc    660

cttttgatgg acctggaaat gttttggccc atgcctatgc ccctgggcca gggattaatg    720

gagatgccca ctttgatgat gatgaacaat ggacaaagga tacaacaggg accaatttat    780

ttctcgttgc tgctcatgaa attggccact ccctgggtct ctttcactca gccaacactg    840

aagctttgat gtacccactc tatcactcac tcacagacct gactcggttc cgcctgtctc    900

aagatgatat aaatggcatt cagtccctct atggacctcc ccctgactcc cctgagaccc    960

ccctggtacc cacggaacct gtccctccag aacctgggac gccagccaac tgtgatcctg   1020

ctttgtcctt tgatgctgtc agcactctga ggggagaaat cctgatcttt aaagacaggc   1080

acttttggcg caaatccctc aggaagcttg aacctgaatt gcatttgatc tcttcatttt   1140

ggccatctct tccttcaggc gtggatgccg catatgaagt tactagcaag gacctcgttt   1200

tcatttttaa aggaaatcaa ttctgggcta tcagaggaaa tgaggtacga gctggatacc   1260

caagaggcat ccacacccta ggtttccctc caaccgtgag gaaaatcgat gcagccattt   1320

ctgataagga aaagaacaaa acatatttct ttgtagagga caaatactgg agatttgatg   1380
```

agaagagaaa ttccatggag ccaggctttc ccaagcaaat agctgaagac tttccaggga 1440
ttgactcaaa gattgatgct gtttttgaag aatttgggtt cttttatttc tttactggat 1500
cttcacagtt ggagtttgac ccaaatgcaa agaaagtgac acacactttg aagagtaaca 1560
gctggcttaa ttgttgaaag agatatgtag aaggcacaat atgggcactt taaatgaagc 1620
taataattct tcacctaagt ctctgtgaat tgaaatgttc gttttctcct gcctgtgctg 1680
tgactcgagt cacactcaag ggaacttgag cgtgaatctg tatcttgccg gtcattttta 1740
tgttattaca gggcattcaa atgggctgct gcttagcttg caccttgtca catagagtga 1800
tctttcccaa gagaagggga agcactcgtg tgcaacagac aagtgactgt atctgtgtag 1860
actatttgct tatttaataa agacgatttg tcagttattt tatctt 1906

<210> SEQ ID NO 16
<211> LENGTH: 2387
<212> TYPE: DNA
<213> ORGANISM: Homo sapiens

<400> SEQUENCE: 16
agacacctct gccctcacca tgagcctctg gcagcccctg gtcctggtgc tcctggtgct 60
gggctgctgc tttgctgccc ccagacagcg ccagtccacc cttgtgctct tccctggaga 120
cctgagaacc aatctcaccg acaggcagct ggcagaggaa tacctgtacc gctatggtta 180
cactcgggtg gcagagatgc gtggagagtc gaaatctctg gggcctgcgc tgctgcttct 240
ccagaagcaa ctgtccctgc ccgagaccgg tgagctggat agcgccacgc tgaaggccat 300
gcgaacccca cggtgcgggg tcccagacct gggcagattc caaacctttg agggcgacct 360
caagtggcac caccacaaca tcacctattg gatccaaaac tactcggaag acttgccgcg 420
ggcggtgatt gacgacgcct ttgcccgcgc cttcgcactg tggagcgcgg tgacgccgct 480
caccttcact cgcgtgtaca gccgggacgc agacatcgtc atccagtttg gtgtcgcgga 540
gcacggagac gggtatccct tcgacgggaa ggacgggctc ctggcacacg cctttcctcc 600
tggccccggc attcagggag acgcccattt cgacgatgac gagttgtggt ccctgggcaa 660
gggcgtcgtg gttccaactc ggtttggaaa cgcagatggc gcggcctgcc acttcccctt 720
catcttcgag ggccgctcct actctgcctg caccaccgac ggtcgctccg acggcttgcc 780
ctggtgcagt accacggcca actacgacac cgacgaccgg tttggcttct gccccagcga 840
gagactctac acccaggacg gcaatgctga tgggaaaccc tgccagtttc cattcatctt 900
ccaaggccaa tcctactccg cctgcaccac ggacggtcgc tccgacggct accgctggtg 960
cgccaccacc gccaactacg accgggacaa gctcttcggc ttctgcccga cccgagctga 1020
ctcgacggtg atgggggcca actcggcggg ggagctgtgc gtcttcccct tcactttcct 1080
gggtaaggag tactcgacct gtaccagcga gggccgcgga gatgggcgcc tctggtgcgc 1140
taccacctcg aactttgaca gcgacaagaa gtggggcttc tgcccggacc aaggatacag 1200
tttgttcctc gtggcggcgc atgagttcgg ccacgcgctg ggcttagatc attcctcagt 1260
gccggaggcg ctcatgtacc ctatgtaccg cttcactgag gggcccccct tgcataagga 1320
cgacgtgaat ggcatccggc acctctatgg tcctcgccct gaacctgagc cacggcctcc 1380
aaccaccacc acaccgcagc ccacggctcc cccgacggtc tgccccaccg gacccccac 1440 tgtccacccc tcagagcgcc ccacagctgg ccccacaggt ccccccctcag ctggccccac 1500 aggtccccccc actgctggcc cttctacggc cactactgtg cctttgagtc cggtggacga 1560
tgcctgcaac gtgaacatct tcgacgccat cgcggagatt gggaaccagc tgtatttgtt 1620

```
caaggatggg aagtactggc gattctctga gggcaggggg agccggccgc agggcccctt   1680

ccttatcgcc gacaagtggc ccgcgctgcc ccgcaagctg gactcggtct ttgaggagcg   1740

gctctccaag aagcttttct tcttctctgg gcgccaggtg tgggtgtaca caggcgcgtc   1800

ggtgctgggc ccgaggcgtc tggacaagct gggcctggga gccgacgtgg cccaggtgac   1860

cggggccctc cggagtggca gggggaagat gctgctgttc agcgggcggc gcctctggag   1920

gttcgacgtg aaggcgcaga tggtggatcc ccggagcgcc agcgaggtgg accggatgtt   1980

ccccggggtg cctttggaca cgcacgacgt cttccagtac cgagagaaag cctatttctg   2040

ccaggaccgc ttctactggc gcgtgagttc ccggagtgag ttgaaccagg tggaccaagt   2100

gggctacgtg acctatgaca tcctgcagtg ccctgaggac tagggctccc gtcctgcttt   2160

ggcagtgcca tgtaaatccc cactgggacc aaccctgggg aaggagccag tttgccggat   2220

acaaactggt attctgttct ggaggaaagg gaggagtgga ggtgggctgg gccctctctt   2280

ctcacctttg tttttgttg gagtgtttct aataaacttg gattctctaa cctttaaaaa   2340

aaaaaaaaaa aaaaaaaaaa aaaaaaaaaa aaaaaaaaaa aaaaaaa                 2387
```

<210> SEQ ID NO 17
<211> LENGTH: 3207
<212> TYPE: DNA
<213> ORGANISM: Homo sapiens

<400> SEQUENCE: 17

```
ggcccacaga ggagcacagc tgtgtttggc tgcagggcca agagcgctgt caagaagacc     60

cacacgcccc cctccagcag ctgaattcct gcagctcagc agccgccgcc agagcaggac    120

gaaccgccaa tcgcaaggca cctctgagaa cttcaggatg cagatgtctc cagccctcac    180

ctgcctagtc ctgggcctgg cccttgtctt tggtgaaggg tctgctgtgc accatccccc    240

atcctacgtg gcccacctgg cctcagactt cggggtgagg gtgtttcagc aggtggcgca    300

ggcctccaag gaccgcaacg tggttttctc accctatggg gtggcctcgg tgttggccat    360

gctccagctg acaacaggag gagaaaccca gcagcagatt caagcagcta tgggattcaa    420

gattgatgac aagggcatgg cccccgccct ccggcatctg tacaaggagc tcatggggcc    480

atggaacaag gatgagatca gcaccacaga cgcgatcttc gtccagcggg atctgaagct    540

ggtccagggc ttcatgcccc acttcttcag gctgttccgg agcacggtca agcaagtgga    600

cttttcagag gtggagagag ccagattcat catcaatgac tgggtgaaga cacacacaaa    660

aggtatgatc agcaacttgc ttgggaaagg agccgtggac cagctgacac ggctggtgct    720

ggtgaatgcc ctctacttca acggccagtg gaagactccc ttccccgact ccagcaccca    780

ccgccgcctc ttccacaaat cagacggcag cactgtctct gtgcccatga tggctcagac    840

caacaagttc aactatactg agttcaccac gcccgatggc cattactacg acatcctgga    900

actgccctac cacggggaca ccctcagcat gttcattgct gccccttatg aaaaagaggt    960

gcctctctct gccctcacca acattctgag tgcccagctc atcagccact ggaaaggcaa   1020

catgaccagg ctgccccgcc tcctggttct gcccaagttc tccctggaga ctgaagtcga   1080

cctcaggaag cccctagaga acctgggaat gaccgacatg ttcagacagt ttcaggctga   1140

cttcacgagt ctttcagacc aagagcctct ccacgtcgcg caggcgctgc agaaagtgaa   1200

gatcgaggtg aacgagagtg gcacggtggc ctcctcatcc acagctgtca tagtctcagc   1260

ccgcatggcc cccgaggaga tcatcatgga cagacccttc ctctttgtgg tccggcacaa   1320
```

ccccacagga acagtccttt tcatgggcca agtgatggaa ccctgaccct ggggaaagac 1380
gccttcatct gggacaaaac tggagatgca tcgggaaaga agaaactccg aagaaaagaa 1440
ttttagtgtt aatgactctt tctgaaggaa gagaagacat ttgccttttg ttaaaagatg 1500
gtaaaccaga tctgtctcca agaccttggc ctctccttgg aggaccttta ggtcaaactc 1560
cctagtctcc acctgagacc ctgggagaga agtttgaagc acaactccct taaggtctcc 1620
aaaccagacg gtgacgcctg cgggaccatc tggggcacct gcttccaccc gtctctctgc 1680
ccactcgggt ctgcagacct ggttcccact gaggcccttt gcaggatgga actacggggc 1740
ttacaggagc ttttgtgtgc ctggtagaaa ctatttctgt tccagtcaca ttgccatcac 1800
tcttgtactg cctgccaccg cggaggaggc tggtgacagg ccaaaggcca gtggaagaaa 1860 cacccttca tctcagagtc cactgtggca ctggccaccc ctccccagta caggggtgct 1920
gcaggtggca gagtgaatgt cccccatcat gtggcccaac tctcctggcc tggccatctc 1980
cctccccaga aacagtgtgc atgggttatt ttggagtgta ggtgacttgt ttactcattg 2040
aagcagattt ctgcttcctt ttatttttat aggaatagag gaagaaatgt cagatgcgtg 2100
cccagctctt caccccccaa tctcttggtg gggaggggtg tacctaaata tttatcatat 2160
ccttgccctt gagtgcttgt tagagagaaa gagaactact aaggaaaata atattattta 2220
aactcgctcc tagtgtttct ttgtggtctg tgtcaccgta tctcaggaag tccagccact 2280
tgactggcac acacccctcc ggacatccag cgtgacggag cccacactgc caccttgtgg 2340
ccgcctgaga ccctcgcgcc ccccgcgccc ctctttttcc ccttgatgga aattgaccat 2400
acaatttcat cctccttcag ggatcaaaa ggacggagtg gggggacaga gactcagatg 2460
aggacagagt ggtttccaat gtgttcaata gatttaggag cagaaatgca aggggctgca 2520
tgacctacca ggacagaact ttccccaatt acagggtgac tcacagccgc attggtgact 2580
cacttcaatg tgtcatttcc ggctgctgtg tgtgagcagt ggacacgtga ggggggggtg 2640
ggtgagagag acaggcagct cggattcaac taccttagat aatatttctg aaaacctacc 2700
agccagaggg tagggcacaa agatggatgt aatgcacttt gggaggccaa ggcgggagga 2760
ttgcttgagc ccaggagttc aagaccagcc tgggcaacat accaagaccc ccgtctcttt 2820
aaaaatatat atattttaaa tatacttaaa tatatatttc taatatcttt aaatatatat 2880
atatatttta aagaccaatt tatgggagaa ttgcacacag atgtgaaatg aatgtaatct 2940
aatagaagcc taatcagccc accatgttct ccactgaaaa atcctctttc tttggggttt 3000
ttctttcttt ctttttgat tttgcactgg acggtgacgt cagccatgta caggatccac 3060
aggggtggtg tcaaatgcta ttgaaattgt gttgaattgt atgctttttc acttttgata 3120
aataaacatg taaaaatgtt tcaaaaaaat aataaaataa ataaatacga agaatatgtc 3180
aggacagtca aaaaaaaaaa aaaaaaa 3207

<210> SEQ ID NO 18
<211> LENGTH: 2398
<212> TYPE: DNA
<213> ORGANISM: Homo sapiens

<400> SEQUENCE: 18
ctgatataga gcaggcgccg cgggtcgcag cacagtgcgg agaccgcagc cccggagccc 60
gggccagggt ccacctgtcc ccgcagcgcc ggctcgcgcc ctcctgccgc agccaccgag 120
ccgccgtcta gcgccccgac ctcgccacca tgagagccct gctggcgcgc ctgcttctct 180
gcgtcctggt cgtgagcgac tccaaaggca gcaatgaact tcatcaagtt ccatcgaact 240

```
gtgactgtct aaatggagga acatgtgtgt ccaacaagta cttctccaac attcactggt    300
gcaactgccc aaagaaattc ggagggcagc actgtgaaat agataagtca aaaacctgct    360
atgaggggaa tggtcacttt taccgaggaa aggccagcac tgacaccatg ggccggccct    420
gcctgccctg gaactctgcc actgtccttc agcaaacgta ccatgcccac agatctgatg    480
ctcttcagct gggcctgggg aaacataatt actgcaggaa cccagacaac cggaggcgac    540
cctggtgcta tgtgcaggtg ggcctaaagc cgcttgtcca agagtgcatg gtgcatgact    600
gcgcagatgg aaaaaagccc tcctctcctc cagaagaatt aaaatttcag tgtggccaaa    660
agactctgag gccccgcttt aagattattg gggagaatt caccaccatc gagaaccagc     720
cctggtttgc ggccatctac aggaggcacc gggggggctc tgtcacctac gtgtgtggag    780
gcagcctcat cagcccttgc tgggtgatca gcgccacaca ctgcttcatt gattacccaa    840
agaaggagga ctacatcgtc tacctgggtc gctcaaggct taactccaac acgcaagggg    900
agatgaagtt tgaggtggaa aacctcatcc tacacaagga ctacagcgct gacacgcttg    960
ctcaccacaa cgacattgcc ttgctgaaga tccgttccaa ggagggcagg tgtgcgcagc   1020
catcccggac tatacagacc atctgcctgc cctcgatgta taacgatccc cagtttggca   1080
caagctgtga gatcactggc tttggaaaag agaattctac cgactatctc tatccggagc   1140
agctgaaaat gactgttgtg aagctgattt cccaccggga gtgtcagcag ccccactact   1200
acggctctga agtcaccacc aaaatgctgt gtgctgctga cccacagtgg aaaacagatt   1260
cctgccaggg agactcaggg ggacccctcg tctgttccct ccaaggccgc atgactttga   1320
ctggaattgt gagctggggc cgtggatgtg ccctgaagga caagccaggc gtctacacga   1380
gagtctcaca cttcttaccc tggatccgca gtcacaccaa ggaagagaat ggcctggccc   1440
tctgagggtc cccagggagg aaacgggcac cacccgcttt cttgctggtt gtcatttttg   1500
cagtagagtc atctccatca gctgtaagaa gagactggga agataggctc tgcacagatg   1560
gatttgcctg tgccacccac cagggcgaac gacaatagct ttaccctcag gcataggcct   1620
gggtgctggc tgcccagacc cctctggcca ggatggaggg gtggtcctga ctcaacatgt   1680
tactgaccag caacttgtct tttctggac tgaagcctgc aggagttaaa aagggcaggg    1740
catctcctgt gcatgggtga agggagagcc agctcccccg acggtgggca tttgtgaggc   1800
ccatggttga gaaatgaata atttcccaat taggaagtgt aacagctgag gtctcttgag   1860
ggagcttagc caatgtggga gcagcggttt ggggagcaga gacactaacg acttcagggc   1920
agggctctga tattccatga atgtatcagg aaatatatat gtgtgtgtat gtttgcacac   1980
ttgtgtgtgg gctgtgagtg taagtgtgag taagagctgg tgtctgattg ttaagtctaa   2040
atatttcctt aaactgtgtg gactgtgatg ccacacagag tggtctttct ggagaggtta   2100
taggtcactc ctggggcctc ttgggtcccc cacgtgacag tgcctgggaa tgtattattc   2160
tgcagcatga cctgtgacca gcactgtctc agtttcactt tcacatagat gtccctttct   2220
tggccagtta tcccttcctt ttagcctagt tcatccaatc ctcactgggt ggggtgagga   2280
ccactcctgt acactgaata tttatatttc actattttta tttatatttt tgtaatttta   2340
aataaaagtg atcaataaaa tgtgattttt ctgatgacaa aaaaaaaaaa aaaaaaaa     2398
```

<210> SEQ ID NO 19
<211> LENGTH: 1570
<212> TYPE: DNA
<213> ORGANISM: Homo sapiens

<400> SEQUENCE: 19

```
gccgagccag ccccttcacc accagccggc cgcgccccgg gaagggaagt ttgtggcgga     60
ggaggttcgt acgggaggag ggggaggcgc ccacgcatct ggggctgact cgctctttcg    120
caaaacgtct gggaggagtc cctggggcca caaaactgcc tccttcctga ggccagaagg    180
agagaagacg tgcagggacc ccgcgcacag gagctgccct cgcgacatgg gtcacccgcc    240
gctgctgccg ctgctgctgc tgctccacac ctgcgtccca gcctcttggg gcctgcggtg    300
catgcagtgt aagaccaacg gggattgccg tgtggaagag tgcgccctgg gacaggacct    360
ctgcaggacc acgatcgtgc gcttgtggga agaaggagaa gagctggagc tggtggagaa    420
aagctgtacc cactcagaga agaccaacag gaccctgagc tatcggactg gcttgaagat    480
caccagcctt accgaggttg tgtgtgggtt agacttgtgc aaccagggca actctggccg    540
ggctgtcacc tattcccgaa gccgttacct cgaatgcatt tcctgtggct catcagacat    600
gagctgtgag aggggccggc accagagcct gcagtgccgc agccctgaag aacagtgcct    660
ggatgtggtg acccactgga tccaggaagg tgaagaaggg cgtccaaagg atgaccgcca    720
cctccgtggc tgtggctacc ttcccggctg cccgggctcc aatggtttcc acaacaacga    780
caccttccac ttcctgaaat gctgcaacac caccaaatgc aacgagggcc caatcctgga    840
gcttgaaaat ctgccgcaga atggccgcca gtgttacagc tgcaagggga acagcaccca    900
tggatgctcc tctgaagaga ctttcctcat tgactgccga ggccccatga atcaatgtct    960
ggtagccacc ggcactcacg aaccgaaaaa ccaaagctat atggtaagag gctgtgcaac   1020
cgcctcaatg tgccaacatg cccacctggg tgacgccttc agcatgaacc acattgatgt   1080
ctcctgctgt actaaaagtg gctgtaacca cccagacctg gatgtccagt accgcagtgg   1140
ggctgctcct cagcctggcc ctgcccatct cagcctcacc atcaccctgc taatgactgc   1200
cagactgtgg ggaggcactc tcctctggac ctaaacctga aatcccccctc tctgccctgg   1260
ctggatccgg gggacccctt tgcccttccc tcggctccca gccctacaga cttgctgtgt   1320
gacctcaggc cagtgtgccg acctctctgg gcctcagttt tcccagctat gaaaacagct   1380
atctcacaaa gttgtgtgaa gcagaagaga aaagctggag gaaggccgtg ggccaatggg   1440
agagctcttg ttattattaa tattgttgcc gctgttgtgt tgttgttatt aattaatatt   1500
catattattt attttatact tacataaaga ttttgtacca gtggacaagg ccaaaaaaaa   1560
aaaaaaaaaa                                                          1570
```

<210> SEQ ID NO 20
<211> LENGTH: 4507
<212> TYPE: DNA
<213> ORGANISM: Homo sapiens

<400> SEQUENCE: 20

```
gaccaattgt catacgactt gcagtgagcg tcaggagcac gtccaggaac tcctcagcag     60
cgcctccttc agctccacag ccagacgccc tcagacagca aagcctaccc ccgcgccgcg    120
ccctgcccgc cgctgcgatg ctcgcccgcg ccctgctgct gtgcgcggtc ctggcgctca    180
gccatacagc aaatccttgc tgttcccacc catgtcaaaa ccgaggtgta tgtatgagtg    240
tgggatttga ccagtataag tgcgattgta cccggacagg attctatgga gaaaactgct    300
caacaccgga atttttgaca agaataaaat tatttctgaa acccactcca aacacagtgc    360
actacatact tacccacttc aagggatttt ggaacgttgt gaataacatt cccttccttc    420
gaaatgcaat tatgagttat gtgttgacat ccagatcaca tttgattgac agtccaccaa    480
```

```
cttacaatgc tgactatggc tacaaaagct gggaagcctt ctctaacctc tcctattata    540
ctagagccct tcctcctgtg cctgatgatt gcccgactcc cttgggtgtc aaaggtaaaa    600
agcagcttcc tgattcaaat gagattgtgg aaaaattgct tctaagaaga aagttcatcc    660
ctgatcccca gggctcaaac atgatgtttg cattctttgc ccagcacttc acgcatcagt    720
ttttcaagac agatcataag cgagggccag ctttcaccaa cgggctgggc catggggtgg    780
acttaaatca tatttacggt gaaactctgg ctagacagcg taaactgcgc cttttcaagg    840
atggaaaaat gaaatatcag ataattgatg gagagatgta tcctcccaca gtcaaagata    900
ctcaggcaga gatgatctac cctcctcaag tccctgagca tctacggttt gctgtggggc    960
aggaggtctt tggtctggtg cctggtctga tgatgtatgc cacaatctgg ctgcgggaac   1020
acaacagagt atgcgatgtg cttaaacagg agcatcctga atggggtgat gagcagttgt   1080
tccagacaag caggctaata ctgataggag agactattaa gattgtgatt gaagattatg   1140
tgcaacactt gagtggctat cacttcaaac tgaaatttga cccagaacta cttttcaaca   1200
aacaattcca gtaccaaaat cgtattgctg ctgaatttaa caccctctat cactggcatc   1260
cccttctgcc tgacaccttt caaattcatg accagaaata caactatcaa cagtttatct   1320
acaacaactc tatattgctg gaacatggaa ttacccagtt tgttgaatca ttcaccaggc   1380
aaattgctgg cagggttgct ggtggtagga atgttccacc cgcagtacag aaagtatcac   1440
aggcttccat tgaccagagc aggcagatga aataccagtc ttttaatgag taccgcaaac   1500
gctttatgct gaagccctat gaatcatttg aagaacttac aggagaaaag gaaatgtctg   1560
cagagttgga agcactctat ggtgacatcg atgctgtgga gctgtatcct gcccttctgg   1620
tagaaaagcc tcggccagat gccatctttg gtgaaaccat ggtagaagtt ggagcaccat   1680
tctccttgaa aggacttatg ggtaatgtta tatgttctcc tgcctactgg aagccaagca   1740
cttttggtgg agaagtgggt tttcaaatca tcaacactgc ctcaattcag tctctcatct   1800
gcaataacgt gaagggctgt ccctttactt cattcagtgt tccagatcca gagctcatta   1860
aaacagtcac catcaatgca agttcttccc gctccggact agatgatatc aatcccacag   1920
tactactaaa agaacgttcg actgaactgt agaagtctaa tgatcatatt tatttattta   1980
tatgaaccat gtctattaat ttaattattt aataatattt atattaaact ccttatgtta   2040
cttaacatct tctgtaacag aagtcagtac tcctgttgcg gagaaaggag tcatacttgt   2100
gaagactttt atgtcactac tctaaagatt ttgctgttgc tgttaagttt ggaaaacagt   2160
ttttattctg ttttataaac cagagagaaa tgagttttga cgtcttttta cttgaatttc   2220
aacttatatt ataagaacga aagtaaagat gtttgaatac ttaaacactg tcacaagatg   2280
gcaaaatgct gaaagttttt acactgtcga tgtttccaat gcatcttcca tgatgcatta   2340
gaagtaacta atgtttgaaa ttttaaagta cttttggtta tttttctgtc atcaaacaaa   2400
aacaggtatc agtgcattat taaatgaata tttaaattag acattaccag taatttcatg   2460
tctacttttt aaaatcagca atgaaacaat aatttgaaat ttctaaattc atagggtaga   2520
atcacctgta aaagcttgtt tgatttctta aagttattaa acttgtacat ataccaaaaa   2580
gaagctgtct tggatttaaa tctgtaaaat cagtagaaat tttactacaa ttgcttgtta   2640
aaatatttta taagtgatgt tcctttttca ccaagagtat aaaccttttt agtgtgactg   2700
ttaaaacttc cttttaaatc aaaatgccaa atttattaag gtggtggagc cactgcagtg   2760
ttatcttaaa ataagaatat tttgttgaga tattccagaa tttgtttata tggctggtaa   2820
```

```
catgtaaaat ctatatcagc aaaagggtct acctttaaaa taagcaataa caaagaagaa   2880

aaccaaatta ttgttcaaat ttaggtttaa acttttgaag caaacttttt tttatccttg   2940

tgcactgcag gcctggtact cagattttgc tatgaggtta atgaagtacc aagctgtgct   3000

tgaataatga tatgttttct cagattttct gttgtacagt ttaatttagc agtccatatc   3060

acattgcaaa agtagcaatg acctcataaa atacctcttc aaaatgctta aattcatttc   3120

acacattaat tttatctcag tcttgaagcc aattcagtag gtgcattgga atcaagcctg   3180

gctacctgca tgctgttcct tttcttttct tcttttagcc attttgctaa gagacacagt   3240

cttctcatca cttcgtttct cctattttgt tttactagtt ttaagatcag agttcacttt   3300

ctttggactc tgcctatatt ttcttacctg aacttttgca agttttcagg taaacctcag   3360

ctcaggactg ctatttagct cctcttaaga agattaaaag agaaaaaaaa aggccctttt   3420

aaaaatagta tacacttatt ttaagtgaaa agcagagaat tttatttata gctaatttta   3480

gctatctgta accaagatgg atgcaaagag gctagtgcct cagagagaac tgtacggggt   3540

ttgtgactgg aaaaagttac gttcccattc taattaatgc cctttcttat ttaaaaacaa   3600

aaccaaatga tatctaagta gttctcagca ataataataa tgacgataat acttcttttc   3660

cacatctcat tgtcactgac atttaatggt actgtatatt acttaattta ttgaagatta   3720

ttatttatgt cttattagga cactatggtt ataaactgtg tttaagccta caatcattga   3780

tttttttttg ttatgtcaca atcagtatat tttctttggg gttacctctc tgaatattat   3840

gtaaacaatc caaagaaatg attgtattaa gatttgtgaa taaattttta gaaatctgat   3900

tggcatattg agatatttaa ggttgaatgt ttgtccttag gataggccta tgtgctagcc   3960

cacaaagaat attgtctcat tagcctgaat gtgccataag actgaccttt taaaatgttt   4020

tgagggatct gtggatgctt cgttaatttg ttcagccaca atttattgag aaaatattct   4080

gtgtcaagca ctgtgggttt taatattttt aaatcaaacg ctgattacag ataatagtat   4140

ttatataaat aattgaaaaa aattttcttt tgggaagagg gagaaaatga aataaatatc   4200

attaaagata actcaggaga atcttcttta caattttacg tttagaatgt ttaaggttaa   4260

gaaagaaata gtcaatatgc ttgtataaaa cactgttcac tgtttttttt aaaaaaaaaa   4320

cttgatttgt tattaacatt gatctgctga caaaacctgg gaatttgggt tgtgtatgcg   4380

aatgtttcag tgcctcagac aaatgtgtat ttaacttatg taaaagataa gtctggaaat   4440

aaatgtctgt ttatttttgt actatttaaa aattgacaga tcttttctga agaaaaaaaa   4500

aaaaaaa                                                             4507
```

<210> SEQ ID NO 21
<211> LENGTH: 1002
<212> TYPE: DNA
<213> ORGANISM: Homo sapiens

<400> SEQUENCE: 21

```
gagccctgca ggcagggggc ttccaggctt gggacacctg ggcattcctg ggccaggaaa     60

gcacccaaca aacctgcaac tcagaagcca aatgagacct atcccaggca ggtccgctct    120

gcgatggtgg ctctcataca ccgcacagaa gtgaggcatc ggggacagcc gctgcggcag    180

cactcgagcc agctcaagcc cgcagctcgc agggagatcc agctccgtcc tgcctgcagc    240

agcacaaccc tgcacaccca ccatggatgt cttcaagaag ggcttctcca tcgccaagga    300

gggcgtggtg ggtgcggtgg aaaagaccaa gcagggggtg acggaagcag ctgagaagac    360

caaggagggg gtcatgtatg tgggagccaa gaccaaggag aatgttgtac agagcgtgac    420
```

```
ctcaggcctg ccttggggct ggggctgggg tggaggccag ccagtgtcct cccatagtgg    480

ccgagaagac caaggagcag gccaacgccg tgagcgaggc tgtggtgagc agcgtcaaca    540

ctgtggccac caagaccgtg gaggaggcgg agaacatcgc ggtcacctcc ggggtggtgc    600

gcaaggagga cttgaggcca tctgcccccc aacaggaggg tgaggcatcc aaagagaaag    660

aggaagtggc agaggaggcc cagagtgggg gagactagag ggctacaggc cagcgtggat    720

gacctgaaga gcgctcctct gccttggaca ccatcccctc ctagcacaag gagtgcccgc    780

cttgagtgac atgcggctgc ccacgctcct gccctcgtct ccctggccac ccttggcctg    840

tccacctgtg ctgctgcacc aacctcactg ccctccctcg gccccaccca ccctctggtc    900

cttctgaccc cacttatgct gctgtgaatt tttttttaa atgattccaa ataaaacttg    960

agcccactcc tgcaaaaaaa aaaaaaaaaa aaaaaaaaaa aa                      1002
```

<210> SEQ ID NO 22
<211> LENGTH: 931
<212> TYPE: DNA
<213> ORGANISM: Homo sapiens

<400> SEQUENCE: 22

```
tttcgtcggc ccgccccttg gcttctgcac tgatggtggg tggatgagta atgcatccag     60

gaagcctgga ggcctgtggt ttccgcaccc gctgccaccc ccgcccctag cgtggacatt    120

tatcctctag cgctcaggcc ctgccgccat cgccgcagat ccagcgccca gagagacacc    180

agagaaccca ccatggcccc ctttgagccc ctggcttctg gcatcctgtt gttgctgtgg    240

ctgatagccc ccagcagggc ctgcacctgt gtcccacccc acccacagac ggccttctgc    300

aattccgacc tcgtcatcag ggccaagttc gtggggacac cagaagtcaa ccagaccacc    360

ttataccagc gttatgagat caagatgacc aagatgtata aagggttcca agccttaggg    420

gatgccgctg acatccggtt cgtctacacc cccgccatgg agagtgtctg cggatacttc    480

cacaggtccc acaaccgcag cgaggagttt ctcattgctg gaaaactgca ggatggactc    540

ttgcacatca ctacctgcag ttttgtggct ccctggaaca gcctgagctt agctcagcgc    600

cggggcttca ccaagaccta cactgttggc tgtgaggaat gcacagtgtt tccctgttta    660

tccatcccct gcaaactgca gagtggcact cattgcttgt ggacggacca gctcctccaa    720

ggctctgaaa agggcttcca gtcccgtcac cttgcctgcc tgcctcggga gccagggctg    780

tgcacctggc agtccctgcg gtcccagata gcctgaatcc tgcccggagt ggaagctgaa    840

gcctgcacag tgtccaccct gttcccactc ccatctttct tccggacaat gaaataaaga    900

gttaccaccc agcagaaaaa aaaaaaaaaa a                                    931
```

<210> SEQ ID NO 23
<211> LENGTH: 2591
<212> TYPE: DNA
<213> ORGANISM: Homo sapiens

<400> SEQUENCE: 23

```
gatgggattg ggttttccc ctcccatgtg ctcaagactg gcgctaaaag ttttgagctt     60

ctcaaaagtc tagagccacc gtccagggag caggtagctg ctgggctccg gggacacttt    120

gcgttcgggc tgggagcgtg ctttccacga cggtgacacg cttccctgga ttggcagcca    180

gactgccttc cgggtcactg ccatggagga gccgcagtca gatcctagcg tcgagccccc    240

tctgagtcag gaaacatttt cagacctatg gaaactactt cctgaaaaca acgttctgtc    300
```

-continued

```
ccccttgccg tcccaagcaa tggatgattt gatgctgtcc ccggacgata ttgaacaatg    360
gttcactgaa gacccaggtc cagatgaagc tcccagaatg ccagaggctg ctccccccgt    420
ggcccctgca ccagcagctc ctacaccggc ggcccctgca ccagcccccct cctggcccct   480
gtcatcttct gtcccttccc agaaaaccta ccagggcagc tacggtttcc gtctgggctt    540
cttgcattct gggacagcca agtctgtgac ttgcacgtac tcccctgccc tcaacaagat    600
gttttgccaa ctggccaaga cctgccctgt gcagctgtgg gttgattcca caccccgcc     660
cggcacccgc gtccgcgcca tggccatcta caagcagtca cagcacatga cggaggttgt    720
gaggcgctgc ccccaccatg agcgctgctc agatagcgat ggtctggccc ctcctcagca    780
tcttatccga gtggaaggaa atttgcgtgt ggagtatttg gatgacagaa acacttttcg    840
acatagtgtg gtggtgccct atgagccgcc tgaggttggc tctgactgta ccaccatcca    900
ctacaactac atgtgtaaca gttcctgcat gggcggcatg aaccggaggc ccatcctcac    960
catcatcaca ctggaagact ccagtggtaa tctactggga cggaacagct ttgaggtgcg   1020
tgtttgtgcc tgtcctggga gagaccggcg cacagaggaa gagaatctcc gcaagaaagg   1080
ggagcctcac cacgagctgc ccccagggag cactaagcga gcactgccca acaacaccag   1140
ctcctctccc cagccaaaga agaaaccact ggatggagaa tatttcaccc ttcagatccg   1200
tgggcgtgag cgcttcgaga tgttccgaga gctgaatgag gccttggaac tcaaggatgc   1260
ccaggctggg aaggagccag gggggagcag ggctcactcc agccacctga agtccaaaaa   1320
gggtcagtct acctcccgcc ataaaaaact catgttcaag acagaagggc ctgactcaga   1380
ctgacattct ccacttcttg ttccccactg acagcctccc acccccatct ctccctcccc   1440
tgccattttg ggttttgggt ctttgaaccc ttgcttgcaa taggtgtgcg tcagaagcac   1500
ccaggacttc catttgcttt gtcccggggc tccactgaac aagttggcct gcactggtgt   1560
tttgttgtgg ggaggaggat ggggagtagg acataccagc ttagatttta aggtttttac   1620
tgtgagggat gtttgggaga tgtaagaaat gttcttgcag ttaagggtta gtttacaatc   1680
agccacattc taggtagggg cccacttcac cgtactaacc agggaagctg tccctcactg   1740
ttgaattttc tctaacttca aggcccatat ctgtgaaatg ctggcatttg cacctacctc   1800
acagagtgca ttgtgagggt taatgaaata atgtacatct ggccttgaaa ccacctttta   1860
ttacatgggg tctagaactt gacccccttg agggtgcttg ttccctctcc ctgttggtcg   1920
gtgggttggt agtttctaca gttgggcagc tggttaggta gagggagttg tcaagtctct   1980
gctggcccag ccaaaccctg tctgacaacc tcttggtgaa ccttagtacc taaaaggaaa   2040
tctcacccca tcccacaccc tggaggattt catctcttgt atatgatgat ctggatccac   2100
caagacttgt tttatgctca gggtcaattt ctttttttctt tttttttttt tttttttcttt  2160
ttctttgaga ctgggtctcg ctttgttgcc caggctggag tggagtggcg tgatcttggc   2220
ttactgcagc ctttgcctcc ccggctcgag cagtcctgcc tcagcctccg gagtagctgg   2280
gaccacaggt tcatgccacc atggccagcc aacttttgca tgttttgtag agatggggtc   2340
tcacagtgtt gcccaggctg gtctcaaact cctgggctca ggcgatccac ctgtctcagc   2400
ctcccagagt gctgggatta caattgtgag ccaccacgtc cagctggaag ggtcaacatc   2460
ttttacattc tgcaagcaca tctgcatttt caccccaccc ttcccctcct tctccctttt   2520
tatatcccat ttttatatcg atctcttatt ttacaataaa actttgctgc cacctgtgtg   2580
tctgaggggt g                                                          2591
```

<210> SEQ ID NO 24
<211> LENGTH: 2195
<212> TYPE: DNA
<213> ORGANISM: Homo sapiens

<400> SEQUENCE: 24

```
aagaaaaacc ttcccggtgc aatcgtgatc tgggaggccc acgtatggcg cctctccaaa      60

ggctgcagaa gtttcttgct aacaaaaagt ccgcacattc gagcaaagac aggctttagc     120

gagttattaa aaacttaggg gcgctcttgt cccccacagg gcccgaccgc acacagcaag     180

gcgatggccc agctgtaagt tggtagcact gagaactagc agcgcgcgcg gagcccgctg     240

agacttgaat caatctggtc taacggtttc ccctaaaccg ctaggagccc tcaatcggcg     300

ggacagcagg gcgcgtcctc tgccactctc gctccgaggt ccccgcgcca gagacgcagc     360

cgcgctccca ccacccacac ccaccgcgcc ctcgttcgcc tcttctccgg gagccagtcc     420

gcgccaccgc cgccgcccag gccatcgcca ccctccgcag ccatgtccac caggtccgtg     480

tcctcgtcct cctaccgcag gatgttcggc ggcccgggca ccgcgagccg gccgagctcc     540

agccggagct acgtgactac gtccacccgc acctacagcc tgggcagcgc gctgcgcccc     600

agcaccagcc gcagcctcta cgcctcgtcc ccgggcggcg tgtatgccac gcgctcctct     660

gccgtgcgcc tgcggagcag cgtgcccggg gtgcggctcc tgcaggactc ggtggacttc     720

tcgctggccg acgccatcaa caccgagttc aagaacaccc gcaccaacga gaaggtggag     780

ctgcaggagc tgaatgaccg cttcgccaac tacatcgaca aggtgcgctt cctggagcag     840

cagaataaga tcctgctggc cgagctcgag cagctcaagg gccaaggcaa gtcgcgcctg     900

ggggacctct acgaggagga gatgcgggag ctgcgccggc aggtggacca gctaaccaac     960

gacaaagccc gcgtcgaggt ggagcgcgac aacctggccg aggacatcat gcgcctccgg    1020

gagaaattgc aggaggagat gcttcagaga gaggaagccg aaaacaccct gcaatctttc    1080

agacaggatg ttgacaatgc gtctctggca cgtcttgacc ttgaacgcaa agtggaatct    1140

ttgcaagaag agattgcctt tttgaagaaa ctccacgaag aggaaatcca ggagctgcag    1200

gctcagattc aggaacagca tgtccaaatc gatgtggatg tttccaagcc tgacctcacg    1260

gctgccctgc gtgacgtacg tcagcaatat gaaagtgtgg ctgccaagaa cctgcaggag    1320

gcagaagaat ggtacaaatc caagtttgct gacctctctg aggctgccaa ccggaacaat    1380

gacgccctgc gccaggcaaa gcaggagtcc actgagtacc ggagacaggt gcagtccctc    1440

acctgtgaag tggatgccct taaaggaacc aatgagtccc tggaacgcca gatgcgtgaa    1500

atggaagaga actttgccgt tgaagctgct aactaccaag acactattgg ccgcctgcag    1560

gatgagattc agaatatgaa ggaggaaatg gctcgtcacc ttcgtgaata ccaagacctg    1620

ctcaatgtta agatggccct tgacattgag attgccacct acaggaagct gctggaaggc    1680

gaggagagca ggatttctct gcctcttcca aacttttcct ccctgaacct gagggaaact    1740

aatctggatt cactccctct ggttgatacc cactcaaaaa ggacacttct gattaagacg    1800

gttgaaacta gagatggaca ggttatcaac gaaacttctc agcatcacga tgaccttgaa    1860

taaaaattgc acacactcag tgcagcaata tattaccagc aagaataaaa aagaaatcca    1920

tatcttaaag aaacagcttt caagtgcctt tctgcagttt ttcaggagcg caagatagat    1980
```

-continued

```
ttggaatagg aataagctct agttcttaac aaccgacact cctacaagat ttagaaaaaa   2040

gtttacaaca taatctagtt tacagaaaaa tcttgtgcta gaatactttt taaaaggtat   2100

tttgaatacc attaaaactg cttttttttt tccagcaagt atccaaccaa cttggttctg   2160

cttcaataaa tctttggaaa aactctttta aaaaa                              2195
```

DETERMINATION OF MAPK-AP-1 PATHWAY ACTIVITY USING UNIQUE COMBINATION OF TARGET GENES

RELATED APPLICATIONS

This application claims the benefit of European Patent Application No. EP17209053.2, filed Dec. 20, 2017, the entirety of the specification and claims thereof is hereby incorporated by reference for all purposes.

INCORPORATION-BY-REFERENCE OF MATERIAL SUBMITTED ON AS A TEXT FILE VIA THE OFFICE ELECTRONIC FILING SYSTEM (EFS-WEB)

A Sequence Listing associated with this application is provided in text format in lieu of a paper copy, and is hereby incorporated by reference into the specification. The name of the text file containing the Sequence Listing is 2017PF02554_2018-09-25_sequencelisting_ST25.txt. The text file is 84 KB, was created on September 25, and is being submitted electronically via EFS-Web.

FIELD OF THE INVENTION

The present invention is in the field of systems biology, bioinformatics, genomic mathematical processing and proteomic mathematical processing. In particular, the invention includes a systems-based mathematical process for determining the activity level of a MAPK-AP-1 cellular signaling pathway in a subject based on expression levels of a unique set of selected target genes in a subject. The invention further provides an apparatus that includes a digital processor configured to perform such a method, a non-transitory storage medium storing instructions that are executable by a digital processing device to perform such a method, and a computer program comprising a program code means for causing a digital processing device to perform such a method. The present invention also includes kits for the determination of expression levels of the unique combinations of target genes.

BACKGROUND OF THE INVENTION

As knowledge of tumors including cancers evolve, it becomes more clear that they are extraordinarily heterogeneous and multifactorial. Tumors and cancers have a wide range of genotypes and phenotypes, they are influenced by their individualized cell receptors (or lack thereof), micro-environment, extracellular matrix, tumor vascularization, neighboring immune cells, and accumulations of mutations, with differing capacities for proliferation, migration, stem cell properties and invasion. This scope of heterogeneity exists even among same classes of tumors. See generally: *Nature* Insight: Tumor Heterogeneity (entire issue of articles), 19 Sep. 2013 (Vol. 501, Issue 7467); Zellmer and Zhang, "Evolving concepts of tumor heterogeneity", *Cell and Bioscience* 2014, 4:69.

Traditionally, physicians have treated tumors, including cancers, as the same within class type (including within receptor type) without taking into account the enormous fundamental individualized nature of the diseased tissue. Patients have been treated with available chemotherapeutic agents based on class and receptor type, and if they do not respond, they are treated with an alternative therapeutic, if it exists. This is an empirical approach to medicine.

There has been a growing trend toward taking into account the heterogeneity of tumors at a more fundamental level as a means to create individualized therapies, however, this trend is still in its formative stages. What is desperately needed are approaches to obtain more metadata about the tumor to inform therapeutic treatment in a manner that allows the prescription of approaches more closely tailored to the individual tumor, and perhaps more importantly, avoiding therapies destined to fail and waste valuable time, which can be life-determinative.

A number of companies and institutions are active in the area of classical, and some more advanced, genetic testing, diagnostics, and predictions for the development of human diseases, including, for example: Affymetrix, Inc.; Bio-Rad, Inc; Roche Diagnostics; Genomic Health, Inc.; Regents of the University of California; Illumina; Fluidigm Corporation; Sequenom, Inc.; High Throughput Genomics; NanoString Technologies; Thermo Fisher; Danaher; Becton, Dickinson and Company; bioMerieux; Johnson & Johnson, Myriad Genetics, and Hologic.

Several companies have developed technology or products directed to gene expression profiling and disease classification. For example, Genomic Health, Inc. is the assignee of numerous patents pertaining to gene expression profiling, for example: U.S. Pat. Nos. 7,081,340; 8,808,994; 8,034,565; 8,206,919; 7,858,304; 8,741,605; 8,765,383; 7,838,224; 8,071,286; 8,148,076; 8,008,003; 8,725,426; 7,888,019; 8,906,625; 8,703,736; 7,695,913; 7,569,345; 8,067,178; 7,056,674; 8,153,379; 8,153,380; 8,153,378; 8,026,060; 8,029,995; 8,198,024; 8,273,537; 8,632,980; 7,723,033; 8,367,345; 8,911,940; 7,939,261; 7,526,637; 8,868,352; 7,930,104; 7,816,084; 7,754,431 and 7,208,470, and their foreign counterparts.

U.S. Pat. No. 9,076,104 to the Regents of the University of California titled "Systems and Methods for Identifying Drug Targets using Biological Networks" claims a method with computer executable instructions by a processor for predicting gene expression profile changes on inhibition of proteins or genes of drug targets on treating a disease, that includes constructing a genetic network using a dynamic Bayesian network based at least in part on knowledge of drug inhibiting effects on a disease, associating a set of parameters with the constructed dynamic Bayesian network, determining the values of a joint probability distribution via an automatic procedure, deriving a mean dynamic Bayesian network with averaged parameters and calculating a quantitative prediction based at least in part on the mean dynamic Bayesian network, wherein the method searches for an optimal combination of drug targets whose perturbed gene expression profiles are most similar to healthy cells.

Affymetrix has developed a number of products related to gene expression profiling. Non-limiting examples of U.S. Patents to Affymetrix include: U.S. Pat. Nos. 6,884,578; 8,029,997; 6,308,170; 6,720,149; 5,874,219; 6,171,798; and 6,391,550.

Likewise, Bio-Rad has a number of products directed to gene expression profiling. Illustrative examples of U.S. Patents to Bio-Rad include: U.S. Pat. Nos. 8,021,894; 8,451,450; 8,518,639; 6,004,761; 6,146,897; 7,299,134; 7,160,734; 6,675,104; 6,844,165; 6,225,047; 7,754,861 and 6,004,761.

Koninklijke Philips N.V. (NL) has filed a number of patent applications in the general area of assessment of cellular signaling pathway activity using various mathematical models, including U.S. Ser. No. 14/233,546 (WO 2013/011479), titled "Assessment of Cellular Signaling Pathway Using Probabilistic Modeling of Target Gene Expression";

U.S. Ser. No. 14/652,805 (WO 2014/102668) titled "Assessment of Cellular Signaling Pathway Activity Using Linear Combinations of Target Gene Expressions"; WO 2014/174003 titled "Medical Prognosis and Prediction of Treatment Response Using Multiple Cellular Signaling Pathway Activities"; and WO 2015/101635 titled "Assessment of the PI3K Cellular Signaling Pathway Activity Using Mathematical Modeling of Target Gene Expression".

Despite this progress, more work is needed to definitively characterize tumor cellular behavior. In particular, there is a critical need to determine which pathways have become pathogenic to the cell. However, it is difficult to identify and separate abnormal cellular signaling from normal cellular pathway activity.

Abnormal MAPK pathway activity plays an important role in cancer and many other diseases. Activator protein 1 (AP-1) is an inducible transcription factor that is robustly activated after MAPK stimulation. AP-1 transcription factors are key targets of MAPK-signaling and regulate the expression of a variety of genes involved in proliferation, differentiation and apoptosis, i.e., biological processes that are crucial for cancer progression. AP-1 is primarily composed of Jun (e.g., c-Jun, JunB and JunD) and/or Fos (e.g., c-Fos, FosB, Fra-1 and Fra-2) and/or ATF and/or JDP family members. In the nucleus, AP-1 binds to the promoters of genes and induces a genetic program that promotes various cellular processes that are required for cancer progression (see also FIG. 1).

With respect to MAPK signaling in e.g. cancer, it is important to be able to detect abnormal MAPK-AP-1 signalling activity in order to enable the right choice of targeted drug treatment. Currently anti-MAPK therapies being used and new therapies are being developed (see Perego P. et al., "Modulation of cell sensitivity to antitumor agents by targeting survival pathways", Biochemical Pharmacology, Vol. 80, No. 10, pages 1459 to 1465). However, today there is no clinical assay available to assess the functional state resp. activity of the MAPK-AP-1 cellular signaling pathway, which in its active state indicates that it is, for instance, more likely to be tumor-promoting compared to its passive state. It is therefore desirable to be able to improve the possibilities of characterizing patients that have a disease, such as a cancer, e.g., a breast, lung, cervical, endometrial, ovarian, pancreatic or prostate cancer, or an immune disorder, which is at least partially driven by an abnormal activity of the MAPK-AP-1 cellular signaling pathway, and that are therefore likely to respond to inhibitors of the MAPK-AP-1 cellular signaling pathway.

It is therefore an object of the invention to provide a more accurate process to determine the tumorigenic propensity of the MAPK-AP-1 cellular signaling pathway in a cell, as well as associated methods of therapeutic treatment, kits, systems, etc.

SUMMARY OF THE INVENTION

The present invention includes methods and apparatuses for determining the activity level of a MAPK-AP-1 cellular signaling pathway in a subject, typically a human with diseased tissue such as a tumor or cancer, wherein the activity level of the MAPK-AP-1 cellular signaling pathway is determined by calculating an activity level of an AP-1 transcription factor element in a sample of the involved tissue isolated from the subject, wherein the activity level of the AP-1 transcription factor element in the sample is associated with MAPK-AP-1 cellular signaling, wherein the activity level of the AP-1 transcription factor element in the sample is determined by measuring the expression levels of a unique set of target genes controlled by the AP-1 transcription factor element using a calibrated pathway model that compares the expression levels of the target genes in the sample with expression levels of the target genes in the calibrated pathway model.

In particular, the unique set of target genes whose expression level is analyzed in the calibrated pathway model includes at least three target genes, at least four target genes, at least five target genes, at least six target genes, at least seven target genes, at least eight target genes, at least nine target genes, at least ten target genes or more selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM. In one embodiment, the unique set of target genes whose expression level is analyzed in the calibrated pathway model comprises at least three target genes, at least four target genes, at least five target genes, at least six target genes, at least seven target genes, at least eight target genes, at least nine target genes or more selected from CCND1, EGFR, EZR, GLRX, MMP1, MMP3, PLAU, PLAUR, SERPINE1, SNCG, and TIMP1.

Using this invention, health care providers will be able to more accurately assess the functional state of the MAPK-AP-1 cellular signaling pathway at specific points in disease progression. Without being bound by any particular theory, it is believed that the identified target genes of the present invention in combination with the analytical methods described herein reduces the noise associated with the use of large subsets of target genes as previously described in the literature. Furthermore, as described and exemplified below, the use of specific combinations of select target genes allows for the precise determination of cellular signaling activity, and allows for an increased accuracy in the determination of disease state and prognosis. Accordingly, such cellular signaling pathway status can be used to, for example but not limited to, identify the presence or absence of disease and/or particular disease state or advancement, identify the presence or absence of a disorder or disease state, identify a particular subtype within a disease or disorder based one the activity level of the MAPK-AP-1 cellular signaling pathway, derive a course of treatment based on the presence or absence of MAPK-AP-1 signaling activity for example by administering a MAPK-AP-1 inhibitor, and/or monitor disease progression in order to, for example, adjust therapeutic protocols based on a predicted drug efficacy in light of the determined activity level of the MAPK-AP-1 cellular signaling pathway in the sample.

The term "AP-1 transcription factor element" or "AP-1 TF element" or "TF element" refers to a protein complex containing at least a member of the Jun (e.g. c-Jun, JunB and JunB) family and/or a member of the Fos (e.g. c-Fos, FosB, Fra-1 and Fra-2) family and/or a member of the ATF family and/or a member of the JDP family, forming e.g. Jun~Jun or Jun~Fos dimers, capable of binding to specific DNA sequences, preferably the response elements 12-O-Tetradecanoylphorbol-13-acetate (TPA) response element (TRE) with binding motif 5'-TGA G/C TCA-3' or cyclic AMP response element (CRE) with binding motif 5'-TGACGTCA-3', thereby controlling transcription of target genes. Preferably, the term refers to either a protein or protein complex transcriptional factor triggered by the binding of AP-1 inducing ligands, such as growth factors (e.g., EGF) and cytokines, to its receptor or an intermediate downstream signaling agent, or triggered by the presence of an AP-1-activating mutation.

The present invention is based on the realization of the inventors that a suitable way of identifying effects occurring in the MAPK-AP-1 cellular signaling pathway can be based on a measurement of the signaling output of the MAPK-AP-1 cellular signaling pathway, which is—amongst others—the transcription of the unique target genes described herein by an AP-1 transcription factor (TF) element controlled by the MAPK-AP-1 cellular signaling pathway. This realization by the inventors assumes that the TF level is at a quasi-steady state in the sample which can be detected by means of—amongst others—the expression values of the target genes. The MAPK-AP-1 cellular signaling pathway targeted herein is known to control many functions in many cell types in humans, such as proliferation, differentiation and apoptosis. Regarding pathological disorders, such as cancer (e.g., breast, cervical, lung, endometrial, ovarian, pancreatic or prostate cancer), the abnormal MAPK-AP-1 cellular signaling activity plays an important role, which is detectable in the expression profiles of the target genes and thus exploited by means of a calibrated mathematical pathway model.

The present invention makes it possible to determine the activity level of the MAPK-AP-1 cellular signaling pathway in a subject by (i) determining an activity level of an AP-1 TF element in a sample isolated from the subject, wherein the determining is based at least in part on evaluating a calibrated pathway model relating expression levels of at least three target genes of the MAPK-AP-1 cellular signaling pathway, the transcription of which is controlled by the AP-1 TF element, to the activity level of the AP-1 TF element, and by (ii) calculating the activity level of the MAPK-AP-1 cellular signaling pathway in the sample based on the calculated activity level of the AP-1 TF element in the sample. This preferably allows improving the possibilities of characterizing patients that have a disease, such as cancer, e.g., a breast, cervical, endometrial, ovarian, pancreatic or prostate cancer, which is at least partially driven by an abnormal activity of the MAPK-AP-1 cellular signaling pathway, and that are therefore likely to respond to inhibitors of the MAPK-AP-1 cellular signaling pathway. In particular embodiments, treatment determination can be based on specific MAPK-AP-1 activity. In a particular embodiment the MAPK-AP-1 cellular signaling status can be set at a cutoff value of odds of the MAPK-AP-1 cellular signaling pathway being activate of, for example, 10:1, 5:1, 4:1, 2:1, 1:1, 1:2, 1:4, 1:5, or 1:10.

In one aspect of the invention, provided herein is a computer implemented method for determining the activity level of a MAPK-AP-1 cellular signaling pathway in a subject performed by computerized device having a processor comprising:

a. calculating an activity level of an AP-1 transcription factor element in a sample isolated from the subject, wherein the activity level of the AP-1 transcription factor element in the sample is associated with MAPK-AP-1 cellular signaling, and wherein the activity level of the AP-1 transcription factor element in the sample is calculated by:
    i. receiving data on the expression levels of at least three, for example, at least four, at least five, at least six, at least seven, at least eight, at least nine, at least ten or more target genes derived from the sample, wherein the AP-1 transcription factor element controls transcription of the at least three target genes, and wherein the at least three target genes are selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM;
    ii. calculating the activity level of the AP-1 transcription factor element in the sample using a calibrated pathway model, wherein the calibrated pathway model compares the expression levels of the at least three target genes in the sample with expression levels of the at least three target genes in the calibrated pathway model which define an activity level of the AP-1 transcription factor element; and,
b. calculating the activity level of the MAPK-AP-1 cellular signaling pathway in the sample based on the calculated activity level of the AP-1 transcription factor element in the sample.

In one embodiment, the at least three, for example, at least four, at least five, at least six, at least seven, at least eight, at least nine or more target genes are selected from CCND1, EGFR, EZR, GLRX, MMP1, MMP3, PLAU, PLAUR, SERPINE1, SNCG, and TIMP1. In one embodiment, the method further comprises assigning a MAPK-AP-1 cellular signaling pathway activity status to the calculated activity level of the MAPK-AP-1 cellular signaling pathway in the sample wherein the activity status is indicative of either an active MAPK-AP-1 cellular signaling pathway or a passive MAPK-AP-1 cellular signaling pathway. In one embodiment, the activity status of the MAPK-AP-1 cellular signaling pathway is established by establishing a specific threshold for activity as described further below. In one embodiment, the threshold is set as a probability that the cellular signaling pathway is active, for example, a 10:1, 5:1, 4:1, 3:1, 2:1, 1:1, 1:2, 1:4, 1:5, or 1:10. In one embodiment, the activity status is based, for example, on a minimum calculated activity. In one embodiment, the method further comprises assigning to the calculated MAPK-AP-1 cellular signaling in the sample a probability that the MAPK-AP-1 cellular signaling pathway is active.

As contemplated herein, the activity level of the AP-1 transcription factor element is determined using a calibrated pathway model executed by one or more computer processors, as further described below. The calibrated pathway model compares the expression levels of the at least three target genes in the sample with expression levels of the at least three target genes in the calibrated pathway model which define an activity level of the AP-1 transcription factor element. In one embodiment, the calibrated pathway model is a probabilistic model incorporating conditional probabilistic relationships that compare the expression levels of the at least three target genes in the sample with expression levels of the at least three target genes in the calibrated pathway model which define a level of an AP-1 transcription factor element to determine the activity level of the AP-1 transcription factor element in the sample. In one embodiment, the probabilistic model is a Bayesian network model. In an alternative embodiment, the calibrated pathway model can be a linear or pseudo-linear model. In an embodiment, the linear or pseudo-linear model is a linear or pseudo-linear combination model.

As contemplated herein, the expression levels of the unique set of target genes can be determined using standard methods known in the art. For example, the expression levels of the target genes can be determined by measuring the level of mRNA of the target genes, through quantitative reverse transcriptase-polymerase chain reaction techniques, using probes associated with a mRNA sequence of the target genes, using a DNA or RNA microarray, and/or by measuring the protein level of the protein encoded by the target genes. Once the expression level of the target genes is determined, the expression levels of the target genes within the sample can be utilized in the calibrated pathway model in a raw state or, alternatively, following normalization of the expression level data. For example, expression level data can be normalized by transforming it into continuous data, z-score data, discrete data, or fuzzy data.

As contemplated herein, the calculation of MAPK-AP-1 signaling in the sample is performed on a computerized device having a processor capable of executing a readable program code for calculating the MAPK-AP-1 signaling in the sample according to the methods described above. Accordingly, the computerized device can include means for receiving expression level data, wherein the data is expression levels of at least three target genes derived from the sample, a means for calculating the activity level of an AP-1 transcription factor element in the sample using a calibrated pathway model, wherein the calibrated pathway model compares the expression levels of the at least three target genes in the sample with expression levels of the at least three target genes in the calibrated pathway model which define an activity level of the AP-1 transcription factor element; a means for calculating the MAPK-AP-1 cellular signaling in the sample based on the calculated activity level of an AP-1 transcription factor element in the sample; and a means for assigning a MAPK-AP-1 cellular signaling pathway activity probability or status to the calculated MAPK-AP-1 cellular signaling in the sample, and, optionally, a means for displaying the MAPK-AP-1 signaling pathway activity probability or status.

In accordance with another disclosed aspect, further provided herein is a non-transitory storage medium capable of storing instructions that are executable by a digital processing device to perform the method according to the present invention as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

Further contemplated herein are methods of treating a subject having a disease or disorder associated with an activated MAPK-AP-1 cellular signaling pathway, or a disorder whose advancement or progression is exacerbated or caused by, whether partially or wholly, an activated MAPK-AP-1 cellular signaling pathway, wherein the determination of the MAPK-AP-1 cellular signaling pathway activity is based on the methods described above, and administering to the subject a MAPK-AP-1 inhibitor if the information regarding the activity level of MAPK-AP-1 cellular signaling pathway is indicative of an active MAPK-AP-1 cellular signaling pathway. In one embodiment, the subject is suffering from a cancer, for example, a breast cancer, a cervical cancer, an endometrial cancer, an ovarian cancer, a pancreatic cancer, or a prostate cancer, or an immune disorder.

Also contemplated herein is a kit for measuring the expression levels of at least six, for example, at least seven, at least eight, at least nine, at least ten or more MAPK-AP-1 cellular signaling pathway target genes, as described herein. In one embodiment, the kit includes one or more components, for example probes, for example labeled probes, and/or PCR primers, for measuring the expression levels of at least six, for example, at least seven, at least eight, at least nine, at least ten or more target genes selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM. In one embodiment, the kit includes one or more components for measuring the expression levels of at least six, for example, at least seven, at least eight, at least nine or more target genes selected from CCND1, EGFR, EZR, GLRX, MMP1, MMP3, PLAU, PLAUR, SERPINE1, SNCG, and TIMP1.

As contemplated herein, the one or more components or means for measuring the expression levels of the particular target genes can be selected from the group consisting of: an DNA array chip, an oligonucleotide array chip, a protein array chip, an antibody, a plurality of probes, for example, labeled probes, a set of RNA reverser-transcriptase sequencing components, and/or RNA or DNA, including cDNA, amplification primers. In one embodiment, the kit includes a set of labeled probes directed to a portion of an mRNA or cDNA sequence of the targeted genes as described herein. In one embodiment, the kit includes a set of primers and probes directed to a portion of an mRNA or cDNA sequence of the targeted genes as described herein. In one embodiment, the labeled probes are contained in a standardized 96-well plate. In one embodiment, the kit further includes primers or probes directed to a set of reference genes. Such reference genes can be, for example, constitutively expressed genes useful in normalizing or standardizing expression levels of the target gene expression levels described herein.

In one embodiment, the kit further includes a non-transitory storage medium containing instructions that are executable by a digital processing device to perform a method according to the present invention as described herein. In one embodiment, the kit includes an identification code that provides access to a server or computer network for analyzing the activity level of the MAPK-AP-1 cellular signaling pathway based on the expression levels of the target genes and the methods described herein.

DETAILED DESCRIPTION OF THE INVENTION

Figure 1:
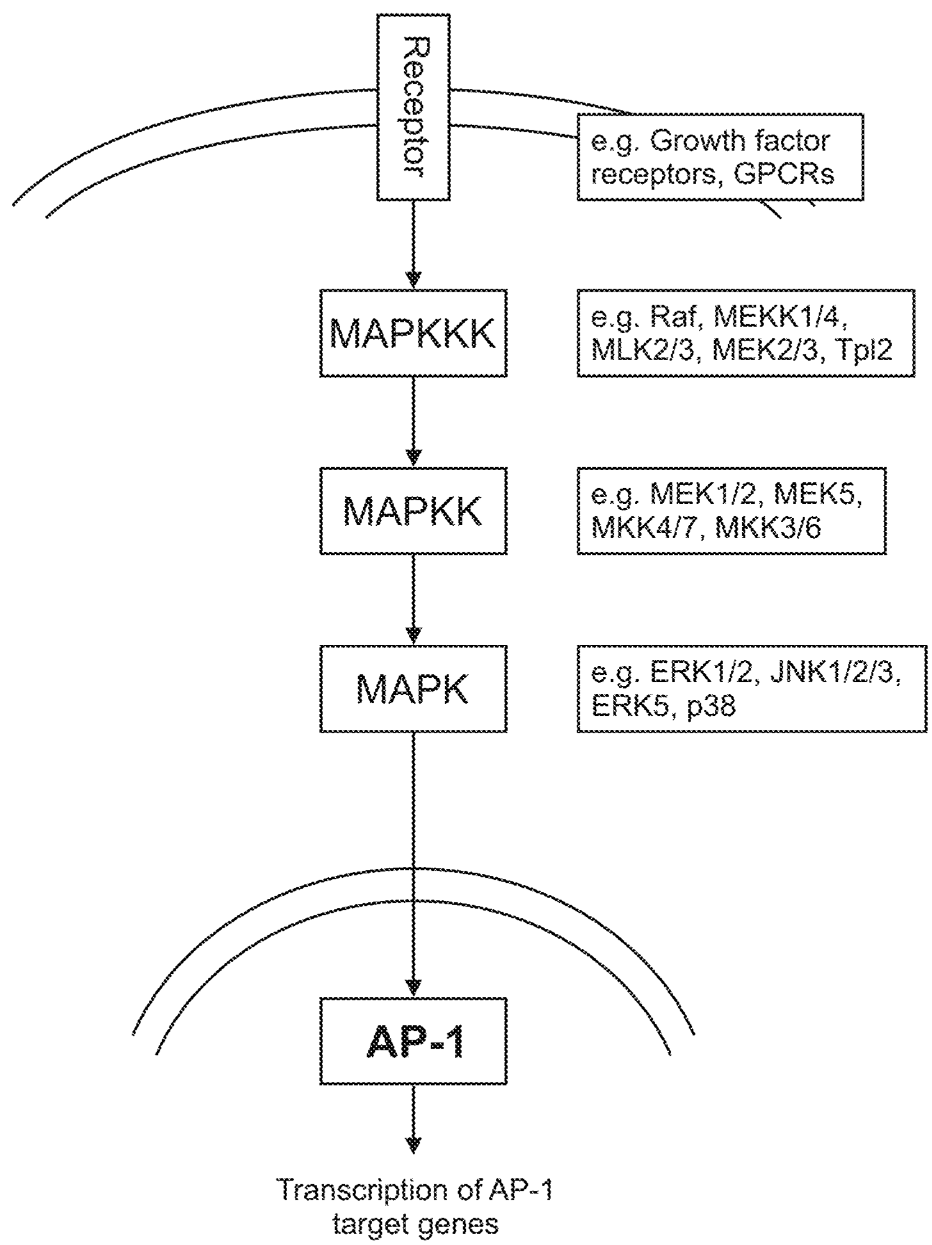
FIG. 1 shows schematically and exemplarily the MAPK-AP-1 cellular signaling pathway. Activator protein 1 (AP-1) is an inducible transcription factor that is robustly activated after MAPK stimulation. AP-1 transcription factors are key targets of MAPK-AP-1 signaling and regulate the expression of a variety of genes involved in proliferation, differentiation and apoptosis, i.e., biological processes that are crucial for cancer progression. AP-1 is primarily composed of Jun (e.g., c-Jun, JunB and JunD) and/or Fos (e.g., c-Fos, FosB, Fra-1 and Fra-2) and/or ATF and/or JDP family members. In the nucleus, AP-1 binds to the promoters of genes and induces a genetic program that promotes various cellular processes that are required for cancer progression.

Provided herein are methods and apparatuses, and in particular computer implemented methods and apparatuses, for determining the activity level of a MAPK-AP-1 cellular signaling pathway in a subject, wherein the activity level of the MAPK-AP-1 cellular signaling pathway is calculated by a) calculating an activity level of an AP-1 transcription factor element in a sample isolated from a subject, wherein the activity level of the AP-1 transcription factor element in the sample is associated with MAPK-AP-1 cellular signaling, and wherein the activity level of the AP-1 transcription factor element in the sample is calculated by measuring the expression levels of a unique set of target genes, wherein the AP-1 transcription factor element controls transcription of the target genes, calculating the activity level of the AP-1 transcription factor element in the sample using a calibrated pathway model, wherein the calibrated pathway model compares the expression levels of the target genes in the sample with expression levels of the target genes in the calibrated pathway model which define an activity level of the AP-1 transcription factor element; and calculating the activity level of the MAPK-AP-1 cellular signaling pathway in the sample based on the calculated activity level of the AP-1 transcription factor element in the sample.

In particular, the unique set of target genes whose expression levels is analyzed in the calibrated pathway model includes at least three, for example, at least four, at least five, at least six, at least seven, at least eight, at least nine, at least ten or more target genes selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM. It has been discovered that analyzing a specific set of target genes as described herein in the disclosed pathway model provides for an advantageously accurate MAPK-AP-1 cellular signaling pathway activity determination. Accordingly, such status can be used to, for example but not limited to, identify the presence or absence of disease and/or particular disease state or advancement, diagnose a specific disease or disease state, or diagnose the presence or absence of a particular disease, derive a course of treatment based on the presence or absence of MAPK-AP-1 signaling activity, monitor disease progression in order to, for example, adjust therapeutic protocols based on a predicted drug efficacy in light of the determined activity of the MAPK-AP-1 signaling pathway in the sample, or develop MAPK-AP-1 targeted therapeutics.

Definitions

All terms used herein are intended to have their plain and ordinary meaning as normally ascribed in the art unless otherwise specifically indicated herein.

Herein, the "level" of a TF element denotes the level of activity of the TF element regarding transcription of its target genes.

The term "subject" or "host", as used herein, refers to any living being. In some embodiments, the subject is an animal, for example a mammal, including a human. In a particular embodiment, the subject is a human. In one embodiment, the human is suspected of having a disorder mediated or exacerbated by an active MAPK-AP-1 cellular signaling pathway, for example, a cancer. In one embodiment, the human has or is suspected of having a breast cancer.

The term "sample", as used herein, means any biological specimen isolated from a subject. Accordingly, "sample" as used herein is contemplated to encompasses the case where e.g. a tissue and/or cells and/or a body fluid of the subject have been isolated from the subject. Performing the claimed method may include where a portion of this sample is extracted, e.g., by means of Laser Capture Microdissection (LCM), or by scraping off the cells of interest from the slide, or by fluorescence-activated cell sorting techniques. In addition, the term "sample", as used herein, also encompasses the case where e.g. a tissue and/or cells and/or a body fluid of the subject has been taken from the subject and has been put on a microscope slide, and the claimed method is performed on the slide. In addition, the term "samples," as used herein, may also encompass circulating tumor cells or CTCs.

The term "AP-1 transcription factor element" or "AP-1 TF element" or "TF element" refers to a protein complex containing at least a member of the Jun (e.g. c-Jun, JunB and JunB) family and/or a member of the Fos (e.g. c-Fos, FosB, Fra-1 and Fra-2) family and/or a member of the ATF family and/or a member of the JDP family, forming e.g. Jun~Jun or Jun~Fos dimers, capable of binding to specific DNA sequences, preferably the response elements 12-O-Tetradecanoylphorbol-13-acetate (TPA) response element (TRE) with binding motif 5'-TGA G/C TCA-3' or cyclic AMP response element (CRE) with binding motif 5'-TGACGTCA-3', thereby controlling transcription of target genes. Preferably, the term refers to either a protein or protein complex transcriptional factor triggered by the binding of AP-1 inducing ligands, such as growth factors (e.g., EGF) and cytokines, to its receptor or an intermediate downstream signaling agent, or triggered by the presence of an AP-1-activating mutation. The term "target gene" as used herein, means a gene whose transcription is directly or indirectly controlled by an AP-1 transcription factor element. The "target gene" may be a "direct target gene" and/or an "indirect target gene" (as described herein).

As contemplated herein, target genes include at least BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM.

As contemplated herein, the present invention includes:

A) A computer implemented method for determining the activity level of a MAPK-AP-1 cellular signaling pathway in a subject performed by a computerized device having a processor comprising:

- a. calculating an activity level of an AP-1 transcription factor element in a sample isolated from the subject, wherein the activity level of the AP-1 transcription factor element in the sample is associated with MAPK-AP-1 cellular signaling, and wherein the activity level of the AP-1 transcription factor element in the sample is calculated by:
  - i. receiving data on the expression levels of at least three, for example, at least five, at least six, at least seven, at least eight, at least nine, at least ten or more target genes derived from the sample, wherein the AP-1 transcription factor element controls transcription of the at least three target genes, and wherein the at least three target genes are selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM;
  - ii. calculating the activity level of the AP-1 transcription factor element in the sample using a calibrated pathway model, wherein the calibrated pathway model compares the expression levels of the at least three target genes in the sample with expression levels of the at least three target genes in the calibrated pathway model which define an activity level of the AP-1 transcription factor element; and,
- b. calculating the activity level of the MAPK-AP-1 cellular signaling pathway in the sample based on the calculated activity level of the AP-1 transcription factor element in the sample.

In one embodiment, the at least three, for example, at least four, at least five, at least six, at least seven, at least eight, at least nine or more target genes are selected from CCND1, EGFR, EZR, GLRX, MMP1, MMP3, PLAU, PLAUR, SERPINE1, SNCG, and TIMP1. In one embodiment, the method further comprises assigning a MAPK-AP-1 cellular signaling pathway activity status to the calculated activity level of the MAPK-AP-1 cellular signaling in the sample, wherein the activity status is indicative of either an active MAPK-AP-1 cellular signaling pathway or a passive MAPK-AP-1 cellular signaling pathway. In one embodiment, the method further comprises displaying the MAPK-AP-1 cellular signaling pathway activity status. In one embodiment, the calibrated pathway model is a probabilistic model incorporating conditional probabilistic relationships that compare the expression levels of the at least three target genes in the sample with expression levels of the at least three target genes in the calibrated pathway model which define a level of the AP-1 transcription factor element to determine the activity level of the AP-1 transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the calibrated pathway model which define a level of AP-1 transcription factor element to determine the activity level of the AP-1 transcription factor element in the sample.

B) A computer program product for determining the activity level of a MAPK-AP-1 cellular signaling pathway in a subject comprising:

- a. a non-transitory computer readable storage medium having computer readable program code embodied therewith, the computer readable program code executable by at least one processor to:
  - i. calculate an activity level of an AP-1 transcription factor element in a sample isolated from a subject, wherein the activity level of the AP-1 transcription factor element in the sample is associated with MAPK-AP-1 cellular signaling, and wherein the activity level of the AP-1 transcription factor element in the sample is calculated by:
    1. receiving data on the expression levels of at least three, for example, at least four, at least five, at least six, at least seven, at least eight, at least nine, at least ten or more target genes derived from the sample, wherein the at least three target genes are selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM;

2. calculating the activity level of the AP-1 transcription factor element in the sample using a calibrated pathway model, wherein the calibrated pathway model compares the expression levels of the at least three target genes in the sample with expression levels of the at least three target genes in the calibrated pathway model which define an activity level of AP-1 transcription factor element; and, b. calculate the activity level of the MAPK-AP-1 cellular signaling pathway in the sample based on the calculated activity level of the AP-1 transcription factor element in the sample.

In one embodiment, the at least three, for example, at least four, at least five, at least six, at least seven, at least eight, at least nine or more target genes are selected from CCND1, EGFR, EZR, GLRX, MMP1, MMP3, PLAU, PLAUR, SERPINE1, SNCG, and TIMP1. In one embodiment, the computer readable program code is executable by at least one processor to assign a MAPK-AP-1 cellular signaling pathway activity status to the calculated activity level of the MAPK-AP-1 cellular signaling in the sample, wherein the activity status is indicative of either an active MAPK-AP-1 cellular signaling pathway or a passive MAPK-AP-1 cellular signaling pathway. In one embodiment, the computer readable program code is executable by at least one processor to display the JAK-STAT signaling pathway activity status. In one embodiment, the calibrated pathway model is a probabilistic model incorporating conditional probabilistic relationships that compare the expression levels of the at least three target genes in the sample with expression levels of the at least three target genes in the calibrated pathway model which define a level of AP-1 transcription factor element to determine the activity level of AP-1 transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the calibrated pathway model which define a level of an AP-1 transcription factor element to determine the activity level of the AP-1 transcription factor element in the sample.

C) A method of treating a subject suffering from a disease associated with an activated MAPK-AP-1 cellular signaling pathway comprising:

a. receiving information regarding the activity level of a MAPK-AP-1 cellular signaling pathway derived from a sample isolated from the subject, wherein the activity level of the MAPK-AP-1 cellular signaling pathway is determined by:

i. calculating an activity level of an AP-1 transcription factor element in a sample isolated from the subject, wherein the activity level of the AP-1 transcription factor element in the sample is associated with MAPK-AP-1 cellular signaling, and wherein the level of the AP-1 transcription factor element in the sample is calculated by:

1. receiving data on the expression levels of at least three, for example, at least four, at least five, at least six, at least seven, at least eight, at least nine, at least ten or more target genes derived from the sample, wherein the AP-1 transcription factor element controls transcription of the at least three target genes, and wherein the at least three target genes are selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM;

2. calculating the activity level of the AP-1 transcription factor element in the sample using a calibrated pathway model, wherein the calibrated pathway model compares the expression levels of the at least three target genes in the sample with expression levels of the at least three target genes in the calibrated pathway model which define an activity level of the AP-1 transcription factor element; and, ii. calculating the activity level of the MAPK-AP-1 cellular signaling pathway in the sample based on the calculated activity level of the AP-1 transcription factor element in the sample; and, b. administering to the subject a MAPK-AP-1 inhibitor if the information regarding the activity level of the MAPK-AP-1 cellular signaling pathway is indicative of a pathogenically active MAPK-AP-1 cellular signaling pathway.

In one embodiment, the at least three, for example, at least four, at least five, at least six, at least seven, at least eight, at least nine or more target genes are selected from CCND1, EGFR, EZR, GLRX, MMP1, MMP3, PLAU, PLAUR, SERPINE1, SNCG, and TIMP1. In one embodiment, the calibrated pathway model is a probabilistic model incorporating conditional probabilistic relationships that compare the expression levels of the at least three target genes in the sample with expression levels of the at least three target genes in the calibrated pathway model which define a level of the AP-1 transcription factor element to determine the activity level of the AP-1 transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the calibrated pathway model which define a level of AP-1 transcription factor element to determine the activity level of the AP-1 transcription factor element in the sample. In an illustrative embodiment, the MAPK-AP-1 inhibitor is SP600125, PD98059, PD184352, U0126, Ro092210, or LLZ16402. In one embodiment, the cancer is a breast cancer, a cervical cancer, an endometrial cancer, an ovarian cancer, a pancreatic cancer, or a prostate cancer. In one embodiment, the cancer is a breast cancer.

D) A kit for measuring expression levels of MAPK-AP-1 cellular signaling pathway target genes comprising:

a. a set of polymerase chain reaction primers directed to at least six, for example, at least seven, at least eight, at least nine, at least ten or more MAPK-AP-1 cellular signaling pathway target genes derived from a sample isolated from a subject; and b. a set of probes directed to the at least six MAPK-AP-1 cellular signaling pathway target genes;

wherein the at least six target genes are selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM.

In one embodiment, the at least six, for example, at least seven, at least eight, at least nine or more target genes are selected from CCND1, EGFR, EZR, GLRX, MMP1, MMP3, PLAU, PLAUR, SERPINE1, SNCG, and TIMP1. In one embodiment, the kit further comprises a computer program product for determining the activity level of a MAPK-AP-1 cellular signaling pathway in the subject comprising: a. a non-transitory computer readable storage medium having computer readable program code embodied therewith, the computer readable program code executable by at least one processor to: i. calculate an activity level of an AP-1 transcription factor element in the sample, wherein the activity level of the AP-1 transcription factor element in the sample is associated with MAPK-AP-1 cellular signaling, and wherein the activity level of the AP-1 transcription factor element in the sample is calculated by: 1. receiving data on the expression levels of the at least six target genes derived from the sample; 2. calculating the activity level of the AP-1 transcription factor element in the sample using a calibrated pathway model, wherein the calibrated pathway model compares the expression levels of the at least six target genes in the sample with expression levels of the at least six target genes in the calibrated pathway model which define an activity level of the AP-1 transcription factor element; and, ii. calculate the activity level of the MAPK-AP-1 cellular signaling pathway in the sample based on the calculated activity level of the AP-1 transcription factor element in the sample.

E) A kit for determining the activity level of a MAPK-AP-1 cellular signaling pathway in a subject comprising:

- a. one or more components capable of identifying expression levels of at least three, for example, at least four, at least five, at least six, at least seven, at least eight, at least nine, at least ten or more MAPK-AP-1 cellular signaling pathway target genes derived from a sample of the subject, wherein the at least three target genes are selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM; and,
- b. optionally, a non-transitory computer readable storage medium having computer readable program code embodied therewith, the computer readable program code executable by at least one processor to:
  - i. calculate an activity level of an AP-1 transcription factor element in the sample, wherein the activity level of the AP-1 transcription factor element in the sample is associated with MAPK-AP-1 cellular signaling, and wherein the activity level of the AP-1 transcription factor element in the sample is calculated by:
    - 1. receiving data on the expression levels of the at least three target genes derived from the sample;
    - 2. calculating the activity level of the AP-1 transcription factor element in the sample using a calibrated pathway model, wherein the calibrated pathway model compares the expression levels of the at least three target genes in the sample with expression levels of the at least three target genes in the calibrated pathway model which define an activity level of the AP-1 transcription factor element; and,
  - ii. calculate the activity level of the MAPK-AP-1 cellular signaling pathway in the sample based on the calculated activity level of the AP-1 transcription factor element in the sample.

Determining the Activity Level of the MAPK-AP-1 Cellular Signaling Pathway

The present invention provides new and improved methods and apparatuses, and in particular computer implemented methods and apparatuses, as disclosed herein, to assess the functional state or activity of the MAPK-AP-1 cellular signaling pathway.

In one aspect of the invention, provided herein is a method of determining MAPK-AP-1 cellular signaling in a subject comprising the steps of:

- a. calculating an activity level of an AP-1 transcription factor element in a sample isolated from a subject, wherein the activity level of the AP-1 transcription factor element in the sample is associated with MAPK-AP-1 cellular signaling, and wherein the activity level of the AP-1 transcription factor element in the sample is calculated by:
  - i. receiving data on the expression levels of at least three, for example, at least four, at least five, at least six, at least seven, at least eight, at least nine, at least ten or more target genes derived from the sample, wherein the AP-1 transcription factor element controls transcription of the at least three target genes, and wherein the at least three target genes are selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM,
  - ii. calculating the activity level of the AP-1 transcription factor element in the sample using a calibrated pathway model, wherein the calibrated pathway model compares the expression levels of the at least three target genes in the sample with expression levels of the at least three more target genes in the calibrated pathway model which define an activity level of the AP-1 transcription factor element; and,
- b. calculating the activity level of the MAPK-AP-1 cellular signaling pathway in the sample based on the calculated activity level of the AP-1 transcription factor element in the sample.

As contemplated herein, the method of calculating the activity level of the MAPK-AP-1 cellular signaling pathway is performed by a computer processor.

Figure 2:
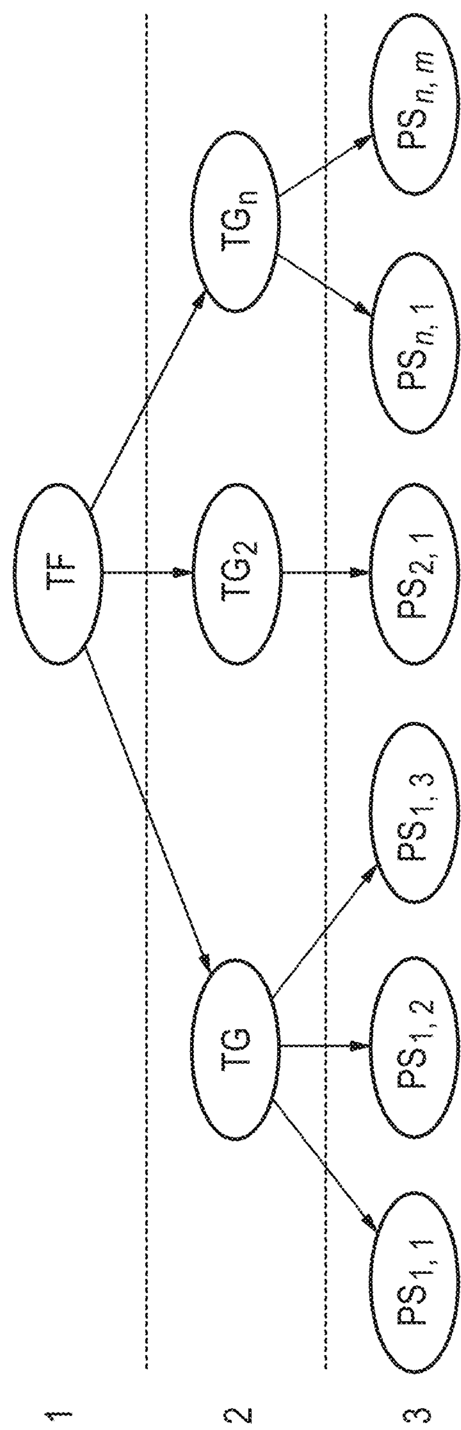
FIG. 2 shows schematically and exemplarily a mathematical model, herein, a Bayesian network model, useful in modelling the transcriptional program of the MAPK-AP-1 cellular signaling pathway.

As a non-limiting generalized example, FIG. 2 provides an exemplary flow diagram used to determine the activity level of the MAPK-AP-1 cellular signaling pathway based on a computer implemented mathematical model constructed of three nodes: (a) a transcription factor (TF) element (for example, but not limited to being, discretized into the states "absent" and "present" or as a continuous observable) in a first layer 1; (b) target genes $TG_1$, $TG_2$, $TG_n$ (for example, but not limited to being, discretized into the states "down" and "up" or as a continuous observable) in a second layer 2, and; (c) measurement nodes linked to the expression levels of the target genes in a third layer 3. The expression levels of the target genes can be determined by, for example, but not limited to, microarray probesets $PS_{1,1}$, $PS_{1,2}$, $PS_{1,3}$, $PS_{2,1}$, $PS_{n,1}$, $PS_{n,m}$ (for example, but limited to being, discretized into the states "low" and "high" or as a continuous observable), but could also be any other gene expression measurements such as, for example, RNAseq or RT-qPCR. The expression of the target genes depends on the activation of the respective transcription factor element, and the measured intensities of the selected probesets depend in turn on the expression of the respective target genes. The model is used to calculate MAPK-AP-1 pathway activity by first determining probeset intensities, i.e., the expression level of the target genes, and calculating backwards in the calibrated pathway model what the probability is that the transcription factor element must be present.

The present invention makes it possible to determine the activity level of the MAPK-AP-1 cellular signaling pathway in a subject by (i) determining an activity level of an AP-1 TF element in a sample of the subject, wherein the determining is based at least in part on evaluating a mathematical model relating expression levels of at least three, for example, at least four, at least five, at least six, at least seven, at least eight, at least nine, at least ten or more target genes of the MAPK-AP-1 cellular signaling pathway, the transcription of which is controlled by the AP-1 TF element, to the activity level of the AP-1 TF element, and by (ii) calculating the activity level of the MAPK-AP-1 cellular signaling pathway in the samplebased on the determined activity level of the AP-1 TF element in the sample. This preferably allows improving the possibilities of characterizing patients that have a disease, such as cancer, e.g., a breast, cervical, endometrial, ovarian, pancreatic or prostate cancer, which is at least partially driven by an abnormal activity of the MAPK-AP-1 cellular signaling pathway, and that are therefore likely to respond to inhibitors of the MAPK-AP-1 cellular signaling pathway. An important advantage of the present invention is that it makes it possible to determine the activity of the MAPK-AP-1 cellular signaling pathway using a single sample, rather than requiring a plurality of samples extracted at different points in time.

Figure 3:
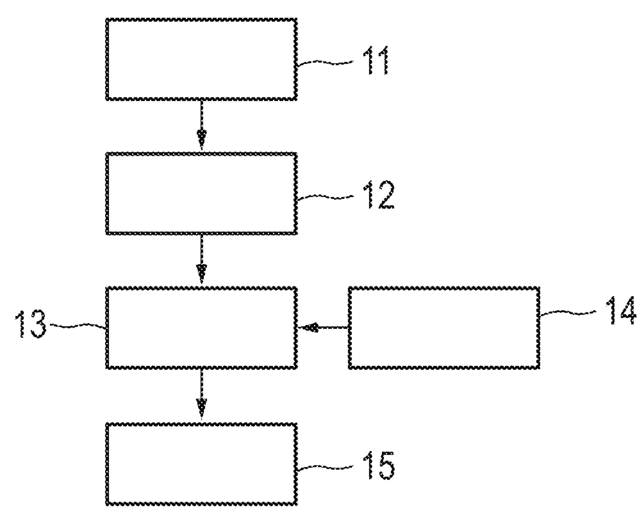
FIG. 3 shows an exemplary flow chart for calculating the activity level of the MAPK-AP-1 cellular signaling pathway based on expression levels of target genes derived from a sample.

Generalized Workflow for Determining the Activity Level of MAPK-AP-1 Cellular Signaling An example flow chart illustrating an exemplary calculation of the activity level of MAPK-AP-1 cellular signaling from a sample isolated from a subject is provided in FIG. 3. First, the mRNA from a sample is isolated (11). Second, the mRNA expression levels of a unique set of at least three or more AP-1 target genes, as described herein, are measured (12) using methods for measuring gene expression that are known in the art. Next, the calculation of transcription factor element (13) is calculated using a calibrated pathway model (14), wherein the calibrated pathway model compares the expression levels of the at least three target genes in the sample with expression levels of the at least three target genes in the calibrated pathway model which have been correlated with a level of an AP-1 transcription factor element. Finally, the activity level of the MAPK-AP-1 cellular signaling pathway is calculated in the sample based on the calculated levels of AP-1 transcription factor element in the sample (15). For example, the MAPK-AP-1 signaling pathway is determined to be active if the activity is above a certain threshold, and can be categorized as passive if the activity falls below a certain threshold.

Target Genes

The present invention utilizes the analyses of the expression levels of unique sets of target genes. Particularly suitable target genes are described in the following text passages as well as the examples below (see, e.g., Tables 1 and 2 below).

Thus, according to an embodiment the target genes are selected from the group consisting of the target genes listed in Table 1 or Table 2 below.

In particular, the unique set of target genes whose expression is analyzed in the calibrated pathway model includes at least three or more target genes, for example, three, four, five, six, seven, eight, nine, ten or more, selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM.

In one embodiment, the at least three or more target genes, for example, three, four, five, six, seven, eight, nine or more, are selected from CCND1, EGFR, EZR, GLRX, MMP1, MMP3, PLAU, PLAUR, SERPINE1, SNCG, and TIMP1.

It has been found by the present inventors that the target genes in the shorter list is more probative for determining the activity of the MAPK-AP-1 cellular signaling pathway.

Measuring Levels of Gene Expression

Data derived from the unique set of target genes described herein is further utilized to determine the activity level of the MAPK-AP-1 cellular signaling pathway using the methods described herein.

Methods for analyzing gene expression levels in isolated samples are generally known. For example, methods such as Northern blotting, the use of PCR, nested PCR, quantitative real-time PCR (qPCR), RNA-seq, or microarrays can all be used to derive gene expression level data. All methods known in the art for analyzing gene expression of the target genes are contemplated herein.

Methods of determining the expression product of a gene using PCR based methods may be of particular use. In order to quantify the level of gene expression using PCR, the amount of each PCR product of interest is typically estimated using conventional quantitative real-time PCR (qPCR) to measure the accumulation of PCR products in real time after each cycle of amplification. This typically utilizes a detectible reporter such as an intercalating dye, minor groove binding dye, or fluorogenic probe whereby the application of light excites the reporter to fluoresce and the resulting fluorescence is typically detected using a CCD camera or photomultiplier detection system, such as that disclosed in U.S. Pat. No. 6,713,297 which is hereby incorporated by reference.

In some embodiments, the probes used in the detection of PCR products in the quantitative real-time PCR (qPCR) assay can include a fluorescent marker. Numerous fluorescent markers are commercially available. For example, Molecular Probes, Inc. (Eugene, Oreg.) sells a wide variety of fluorescent dyes. Non-limiting examples include Cy5, Cy3, TAMRA, R6G, R110, ROX, JOE, FAM, Texas Red™, and Oregon Green™. Additional fluorescent markers can include IDT ZEN Double-Quenched Probes with traditional 5' hydrolysis probes in qPCR assays. These probes can contain, for example, a 5' FAM dye with either a 3' TAMRA Quencher, a 3' Black Hole Quencher (BHQ, Biosearch Technologies), or an internal ZEN Quencher and 3' Iowa Black Fluorescent Quencher (IBFQ).

Fluorescent dyes useful according to the invention can be attached to oligonucleotide primers using methods well known in the art. For example, one common way to add a fluorescent label to an oligonucleotide is to react an N-Hydroxysuccinimide (NHS) ester of the dye with a reactive amino group on the target. Nucleotides can be modified to carry a reactive amino group by, for example, inclusion of an allyl amine group on the nucleobase. Labeling via allyl amine is described, for example, in U.S. Pat. Nos. 5,476,928 and 5,958,691, which are incorporated herein by reference. Other means of fluorescently labeling nucleotides, oligonucleotides and polynucleotides are well known to those of skill in the art.

Other fluorogenic approaches include the use of generic detection systems such as SYBR-green dye, which fluoresces when intercalated with the amplified DNA from any gene expression product as disclosed in U.S. Pat. Nos. 5,436,134 and 5,658,751 which are hereby incorporated by reference.

Another useful method for determining target gene expression levels includes RNA-seq, a powerful analytical tool used for transcriptome analyses, including gene expression level difference between different physiological conditions, or changes that occur during development or over the course of disease progression.

Another approach to determine gene expression levels includes the use of microarrays for example RNA and DNA microarray, which are well known in the art. Microarrays can be used to quantify the expression of a large number of genes simultaneously.

Calibrated Pathway Model

As contemplated herein, the expression levels of the unique set of target genes described herein are used to calculate the activity level of the AP-1 transcription factor element using a calibrated pathway model as further described below. The calibrated pathway model compares the expression levels of the at least three target genes in the sample with expression levels of the at least three target genes in the calibrated pathway model which define an activity level of the AP-1 transcription factor element.

As contemplated herein, the calibrated pathway model is based on the application of a mathematical model. For example, the calibrated model can be based on a probabilistic model, for example a Bayesian network, or a linear or pseudo-linear model.

In one embodiment, the calibrated pathway model is a probabilistic model incorporating conditional probabilistic relationships that compare the expression levels of the at least three target genes in the sample with expression levels of the at least three target genes in the calibrated pathway model which define a level of an AP-1 transcription factor element to determine the activity level of the AP-1 transcription factor element in the sample. In one embodiment, the probabilistic model is a Bayesian network model.

In an alternative embodiment, the calibrated pathway model can be a linear or pseudo-linear model. In an embodiment, the linear or pseudo-linear model is a linear or pseudo-linear combination model.

Figure 4:
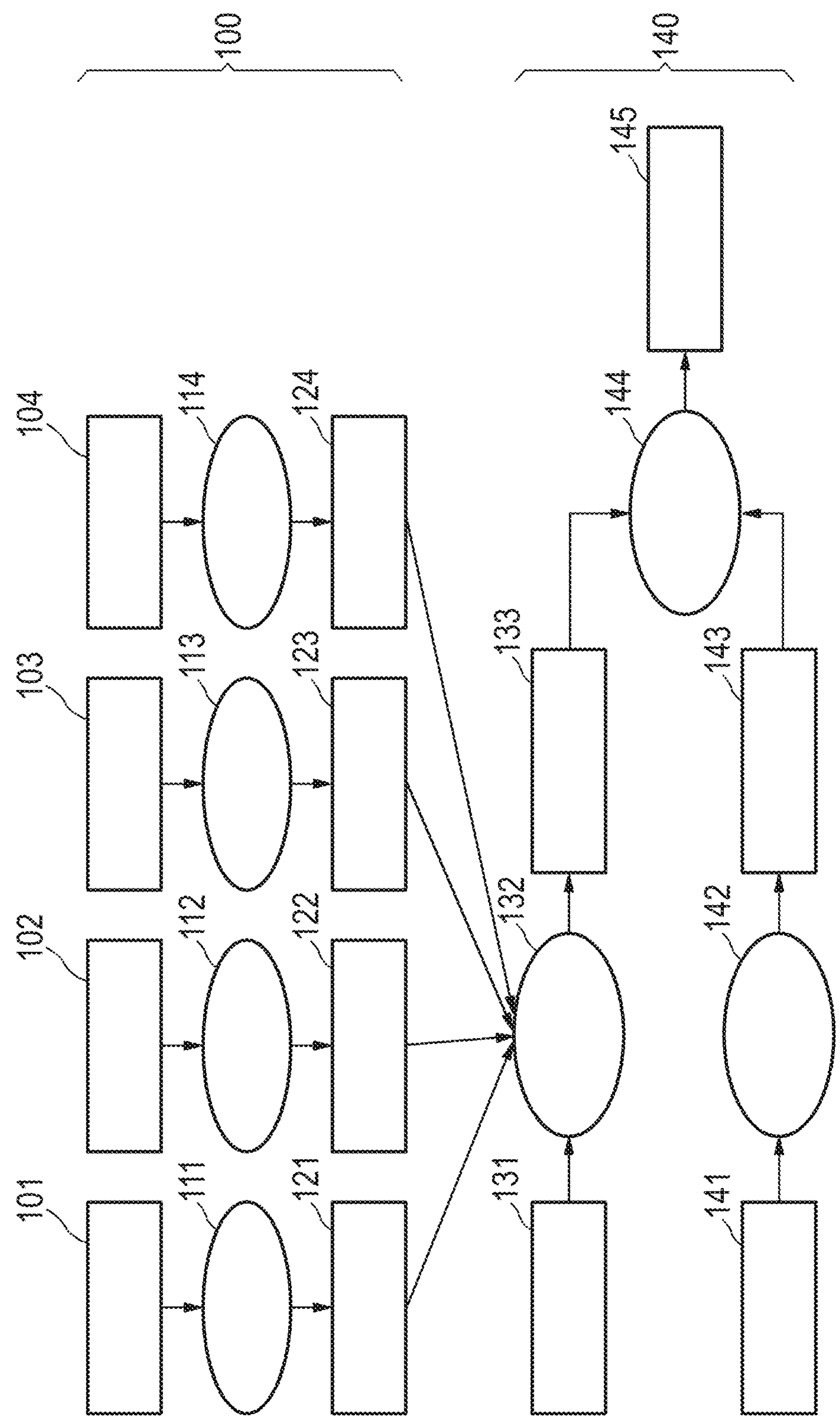
FIG. 4 shows an exemplary flow chart for obtaining a calibrated pathway model as described herein.

A non-limiting exemplary flow chart for a calibrated pathway model is shown in FIG. 4. As an initial step, the training data for the mRNA expression levels is collected and normalized. The data can be collected using, for example microarray probeset intensities (101), real-time PCR Cq values (102), raw RNAseq reads (103), or alternative measurement modalities (104) known in the art. The raw expression level data can then be normalized for each method, respectively, by normalization using a normalization algorithm, for example, frozen robust military analysis (fRMA) or MAS5.0 (111), normalization to average Cq of reference genes (112), normalization of reads into reads/fragments per kilobase of transcript per million mapped reads (RPKM/FPKM) (113), or normalization to w.r.t. reference genes/proteins (114). This normalization procedure leads to a normalized probeset intensity (121), normalized Cq values (122), normalized RPKM/FPKM (123), or normalized measurement (124) for each method, respectively, which indicate target gene expression levels within the training samples.

Once the training data has been normalized, a training sample ID or IDs (131) is obtained and the training data of these specific samples is obtained from one of the methods for determining gene expression (132). The final gene expression results from the training sample are output as training data (133). All of the data from various training samples are incorporated to calibrate the model (including for example, thresholds, CPTs, for example in the case of the probabilistic or Bayesian network, weights, for example, in the case of the linear or pseudo-linear model, etc) (144). In addition, the pathway's target genes and measurement nodes (141) are used to generate the model structure for example, as described in FIG. 2 (142). The resulting model structure (143) of the pathway is then incorporated with the training data (133) to calibrate the model (144), wherein the gene expression levels of the target genes is indicative of the transcription factor element activity. As a result of the transcription factor element calculations in the training samples, a calibrated pathway model (145) is calculated which assigns the MAPK-AP-1 cellular signaling pathway activity level for a subsequently examined sample of interest, for example from a subject with a cancer, based on the target gene expression levels in the training samples.

Transcription Factor Element Calculation

Figure 5:
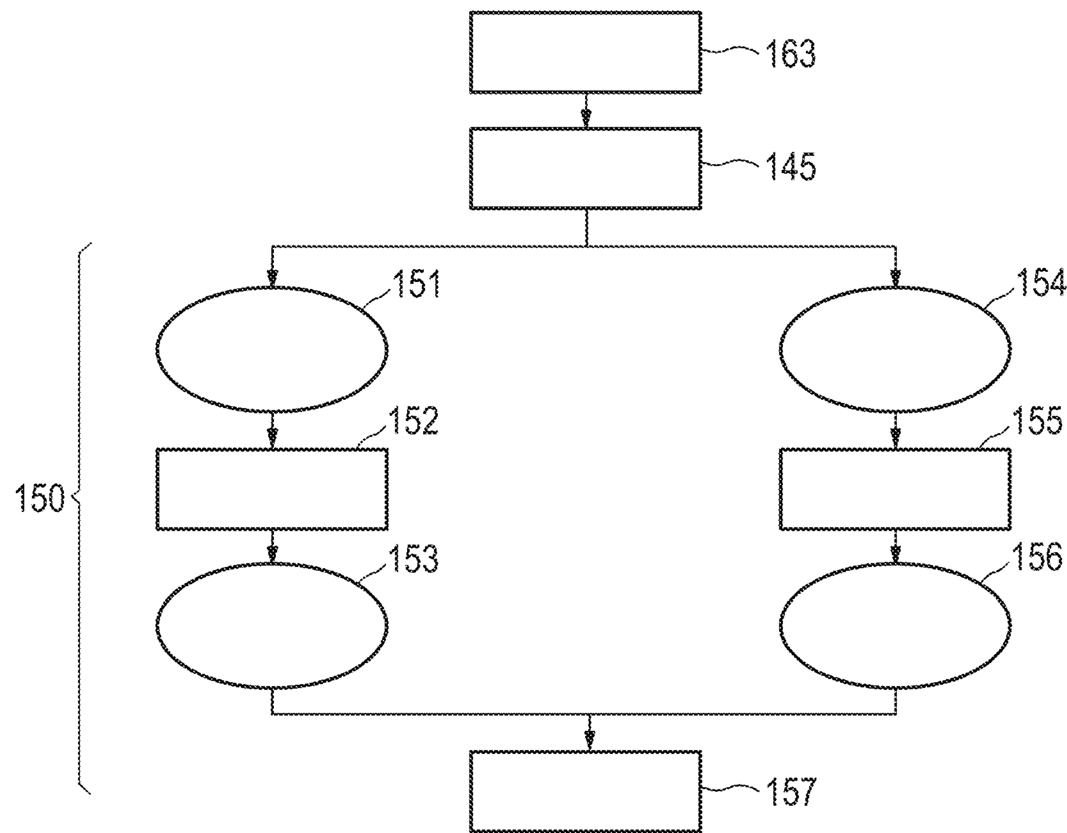
FIG. 5 shows an exemplary flow chart for calculating the Transcription Factor (TF) Element as described herein.

A non-limiting exemplary flow chart for calculating the Transcription Factor Element activity level is provided in FIG. 5. The expression level data (test data) (163) from a sample isolated from a subject is input into the calibrated pathway model (145). The mathematical model may be a probabilistic model, for example a Bayesian network model, a linear model, or pseudo-linear model.

The mathematical model may be a probabilistic model, for example a Bayesian network model, based at least in part on conditional probabilities relating the AP-1 TF element and expression levels of the at least three target genes of the MAPK-AP-1 cellular signaling pathway measured in the sample of the subject, or the mathematical model may be based at least in part on one or more linear combination(s) of expression levels of the at least three target genes of the MAPK-AP-1 cellular signaling pathway measured in the sample of the subject. In particular, the determining of the activity of the MAPK-AP-1 cellular signaling pathway may be performed as disclosed in the published international patent application WO 2013/011479 A2 ("Assessment of cellular signaling pathway activity using probabilistic modeling of target gene expression"), and incorporated herein by reference. Briefly, the data is entered into a Bayesian network (BN) inference engine call (for example, a BNT toolbox) (154). This leads to a set of values for the calculated marginal BN probabilities of all the nodes in the BN (155). From these probabilities, the transcription factor (TF) node's probability (156) is determined and establishes the TF's element activity level (157).

Alternatively, the mathematical model may be a linear model. For example, a linear model can be used as described in the published international patent application WO 2014/102668 A2 ("Assessment of cellular signaling pathway activity using linear combination(s) of target gene expressions"), the contents of which are herewith incorporated in their entirety. Further details regarding the calculating/determining of cellular signaling pathway activity using mathematical modeling of target gene expression can also be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945. Briefly, the data is entered into a calculated weighted linear combination score (w/c) (151). This leads to a set of values for the calculated weighted linear combination score (152). From these weighted linear combination scores, the transcription factor (TF) node's weighted linear combination score (153) is determined and establishes the TF's element activity level (157).

Procedure for Discretized Observables

Figure 6:
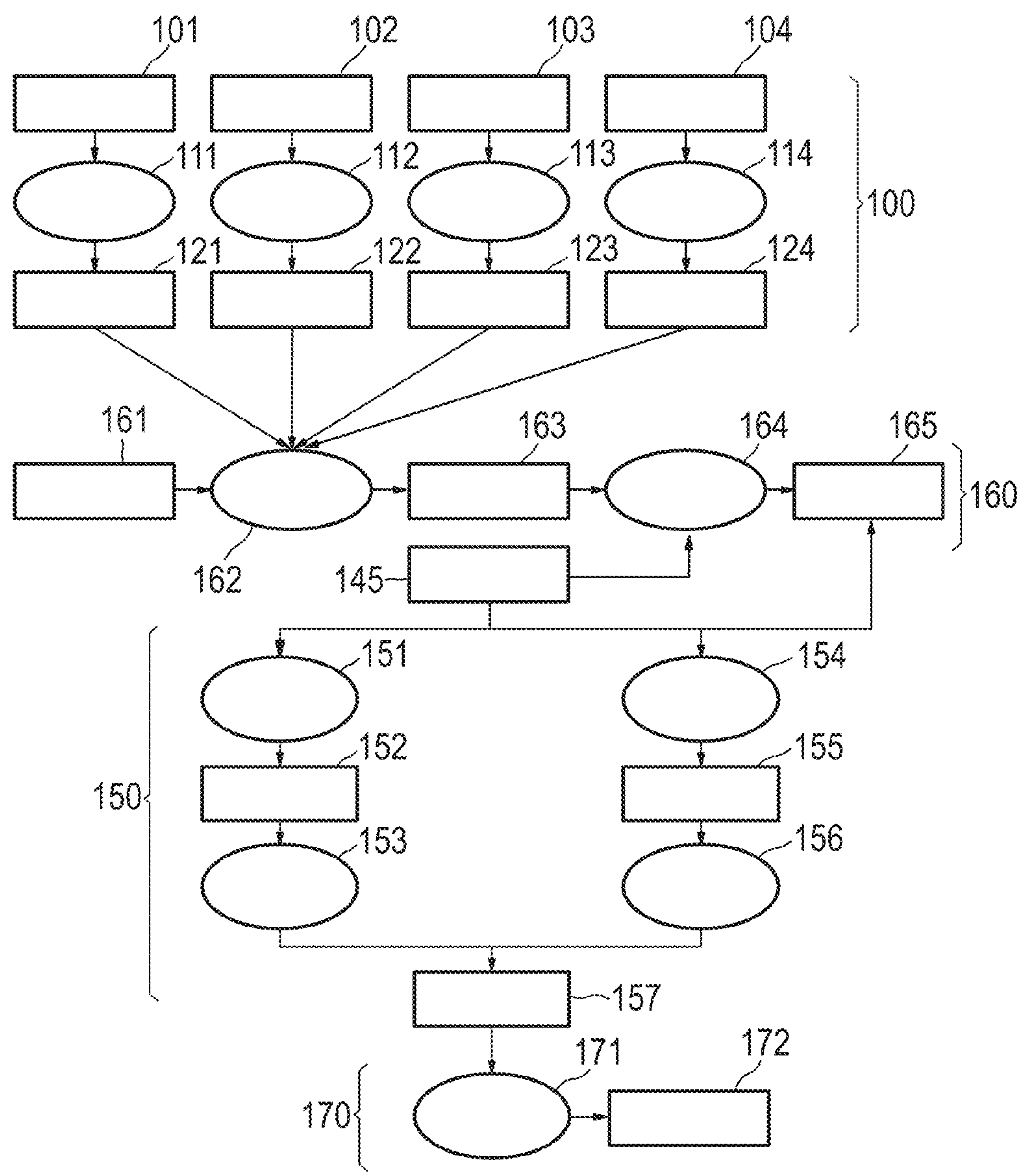
FIG. 6 shows an exemplary flow chart for calculating the MAPK-AP-1 cellular signaling pathway activity level using discretized observables.

A non-limiting exemplary flow chart for calculating the activity level of a MAPK-AP-1 cellular signaling pathway as a discretized observable is shown in FIG. 6. First, the test sample is isolated and given a test sample ID (161). Next, the test data for the mRNA expression levels is collected and normalized (162). The test data can be collected using the same methods as discussed for the training samples in FIG. 5, using microarray probeset intensities (101), real-time PCR Cq values (102), raw RNAseq reads (103), or an alternative measurement modalities (104). The raw expression level data can then be normalized for each method, respectively, by normalization using an algorithm, for example IRMA or MAS5.0 (111), normalization to average Cq of reference genes (112), normalization of reads into RPKM/FPKM (113), and normalization to w.r.t. reference genes/proteins (114). This normalization procedure leads to a normalized probeset intensity (121), normalized Cq values (122), normalized RPKM/FPKM (123), or normalized measurement (124) for each method, respectively.

Once the test data has been normalized, the resulting test data (163) is analyzed in a thresholding step (164) based on the calibrated pathway model (145), resulting in the thresholded test data (165). In using discrete observables, in one non-limiting example, every expression above a certain threshold is, for example, given a value of 1 and values below the threshold are given a value of 0, or in an alternative embodiment, the probability mass above the threshold as described herein is used as a thresholded value. Based on the calibrated pathway model, this value represents the TF's element activity level (157), which is then used to calculate the pathway's activity level (171). The final output gives the pathway's activity level (172) in the test sample being examined from the subject.

Procedure for Continuous Observables

Figure 7:
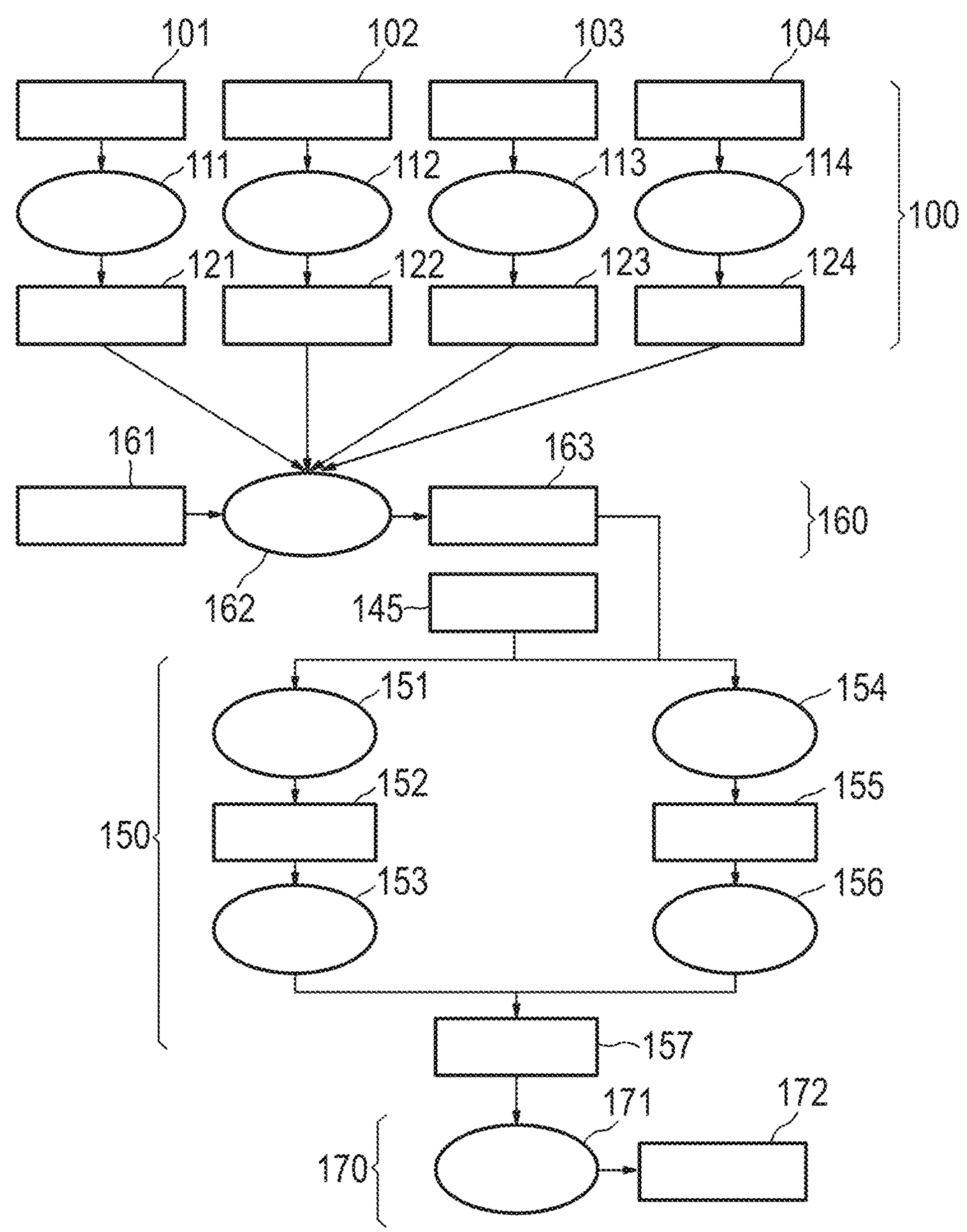
FIG. 7 shows an exemplary flow chart for calculating the MAPK-AP-1 cellular signaling pathway activity level using continuous observables.

A non-limiting exemplary flow chart for calculating the activity level of a MAPK-AP-1 cellular signaling pathway as a continuous observable is shown in FIG. 7. First, the test sample is isolated and given a test sample ID (161). Next, the test data for the mRNA expression levels is collected and normalized (162). The test data can be collected using the same methods as discussed for the training samples in FIG. 5, using microarray probeset intensities (101), real-time PCR Cq values (102), raw RNAseq reads (103), or an alternative measurement modalities (104). The raw expression level data can then be normalized for each method, respectively, by normalization using an algorithm, for example fRMA (111), normalization to average Cq of reference genes (112), normalization of reads into RPKM/FPKM (113), and normalization to w.r.t. reference genes/proteins (114). This normalization procedure leads to a normalized probeset intensity (121), normalized Cq values (122), normalized RPKM/FPKM (123), or normalized measurement (124) for each method, respectively.

Once the test data has been normalized, the resulting test data (163) is analyzed in the calibrated pathway model (145). In using continuous observables, as one non-limiting example, the expression levels are converted to values between 0 and 1 using a sigmoid function as described in further detail below. The transcription factor element calculation as described herein is used to interpret the test data in combination with the calibrated pathway model, the resulting value represents the TF's element activity level (157), which is then used to calculate the pathway's activity level (171). The final output then gives the pathway's activity level (172) in the test sample.

Target Gene Expression Level Determination Procedure

Figure 8:
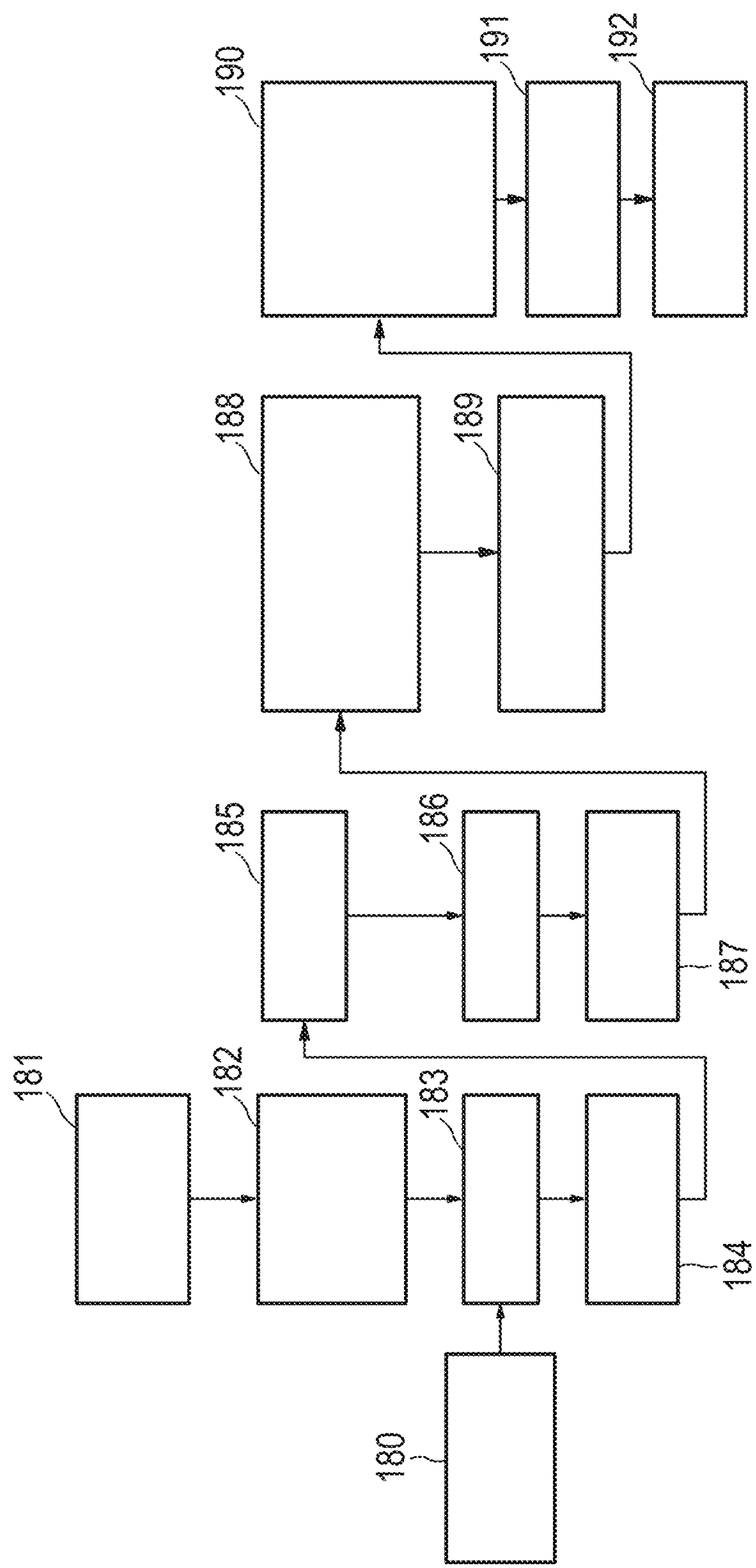
FIG. 8 shows an exemplary flow chart for determining Cq values from RT-qPCR analysis of the target genes of the MAPK-AP-1 cellular signaling pathway.

A non-limiting exemplary flow chart for deriving target gene expression levels from a sample isolated from a subject is shown in FIG. 8. In one exemplary embodiment, samples are received and registered in a laboratory. Samples can include, for example, Formalin-Fixed, Paraffin-Embedded (FFPE) samples (181) or fresh frozen (FF) samples (180). FF samples can be directly lysed (183). For FFPE samples, the paraffin can be removed with a heated incubation step upon addition of Proteinase K (182). Cells are then lysed (183), which destroys the cell and nuclear membranes which makes the nucleic acid (NA) available for further processing. The nucleic acid is bound to a solid phase (184) which could for example, be beads or a filter. The nucleic acid is then washed with washing buffers to remove all the cell debris which is present after lysis (185). The clean nucleic acid is then detached from the solid phase with an elution buffer (186). The DNA is removed by DNAse treatment to ensure that only RNA is present in the sample (187). The nucleic acid sample can then be directly used in the RT-qPCR sample mix (188). The RT-qPCR sample mixes contains the RNA sample, the RT enzyme to prepare cDNA from the RNA sample and a PCR enzyme to amplify the cDNA, a buffer solution to ensure functioning of the enzymes and can potentially contain molecular grade water to set a fixed volume of concentration. The sample mix can then be added to a multiwell plate (i.e., 96 well or 384 well plate) which contains dried RT-qPCR assays (189). The RT-qPCR can then be run in a PCR machine according to a specified protocol (190). An example PCR protocol includes i) 30 minutes at 50° C.; ii) 5 minutes at 95° C.; iii) 15 seconds at 95° C.; iv) 45 seconds at 60° C.; v) 50 cycles repeating steps iii and iv. The Cq values are then determined with the raw data by using the second derivative method (191). The Cq values are exported for analysis (192).

Computer Programs and Computer Implemented Methods

As contemplated herein, the calculation of MAPK-AP-1 signaling in the sample is performed on a computerized device having a processor capable of executing a readable program code for calculating the MAPK-AP-1 cellular signaling pathway activity in the sample according to the methods described above. Accordingly, the computerized device can include means for receiving expression level data, wherein the data is expression levels of at least three, for example, at least four, at least five, at least six, at least seven, at least eight, at least nine, at least ten or more target genes derived from the sample, a means for calculating the activity level of an AP-1 transcription factor element in the sample using a calibrated pathway model, wherein the calibrated pathway model compares the expression levels of the at least three target genes in the sample with expression levels of the at least three target genes in the calibrated pathway model which have been correlated with a level of the AP-1 transcription factor element; a means for calculating the activity level of the MAPK-AP-1 cellular signaling pathway in the sample based on the calculated activity level of AP-1 transcription factor element in the sample; and a means for assigning a MAPK-AP-1 cellular signaling pathway activity probability or status to the calculated activity level of the MAPK-AP-1 cellular signaling pathway in the sample, and a means for displaying the MAPK-AP-1 signaling pathway activity probability or status.

In accordance with another disclosed aspect, a non-transitory storage medium stores instructions that are executable by a digital processing device to perform a method according to the present invention as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

In accordance with another disclosed aspect, an apparatus comprises a digital processor configured to perform a method according to the present invention as described herein.

In accordance with another disclosed aspect, a computer program comprises program code means for causing a digital processing device to perform a method according to the present invention as described herein. The digital processing device may be a handheld device (e.g., a personal data assistant or smartphone), a notebook computer, a desktop computer, a tablet computer or device, a remote network server, or so forth.

In one embodiment, a computer program or system is provided for predicting the activity status of an AP-1 transcription factor element in a human cancer sample that includes a means for receiving data corresponding to the expression level of at least three AP-1 target genes in a sample from a host. In some embodiments, a means for receiving data can include, for example, a processor, a central processing unit, a circuit, a computer, or the data can be received through a web site.

In one embodiment, a computer program or system is provided for predicting the activity status of an AP-1 transcription factor element in a human cancer sample that includes a means for displaying the MAPK-AP-1 pathway signaling status in a sample from a host. In some embodiments, a means for displaying can include a computer monitor, a visual display, a paper print out, a liquid crystal display (LCD), a cathode ray tube (CRT), a graphical keyboard, a character recognizer, a plasma display, an organic light-emitting diode (OLED) display, or a light emitting diode (LED) display, or a physical print out.

In accordance with another disclosed aspect, a signal represents a determined activity of a MAPK-AP-1 cellular signaling pathway in a subject, wherein the determined activity results from performing a method according to the present invention as described herein. The signal can be a digital signal or it can be an analog signal.

In one aspect of the present invention, a computer implemented method is provided for predicting the activity status of a MAPK-AP-1 signaling pathway in a human cancer sample performed by a computerized device having a processor comprising: a) calculating an activity level of an AP-1 transcription factor element in a human cancer sample, wherein the activity level of the AP-1 transcription factor element in the human cancer sample is associated with MAPK-AP-1 cellular signaling, and wherein the activity level of the AP-1 transcription factor element in the human cancer sample is calculated by i) receiving data on the expression levels of at least three, for example, at least four, at least five, at least six, at least seven, at least eight, at least nine, at least ten or more target genes derived from the human cancer sample, wherein the AP-1 transcription factor controls transcription of the at least three target genes, and wherein the at least three target genes are selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM; ii) calculating the activity level of the AP-1 transcription factor element in the human cancer sample using a calibrated pathway model, wherein the calibrated pathway model compares the expression levels of the at least three target genes in the human cancer sample with expression levels of the at least three target genes in the calibrated pathway model which have been correlated with an activity level of the AP-1 transcription factor element; b) calculating the activity level of the MAPK-AP-1 cellular signaling pathway in the human cancer sample based on the calculated activity level of the AP-1 transcription factor element in the human cancer sample; c) assigning a MAPK-AP-1 cellular signaling pathway activity status to the calculated activity level of the MAPK-AP-1 cellular signaling pathway in the human cancer sample, wherein the activity status is indicative of either an active MAPK-AP-1 cellular signaling pathway or a passive MAPK-AP-1 cellular signaling pathway; and d) displaying the MAPK-AP-1 signaling pathway activity status.

In one aspect of the invention, a system is provided for determining the activity level of a MAPK-AP-1 cellular signaling pathway in a subject comprising a) a processor capable of calculating an activity level of an AP-1 transcription factor element in a sample derived from the subject; b) a means for receiving data, wherein the data is an expression level of at least three, for example, at least four, at least five, at least six, at least seven, at least eight, at least nine, at least 10 or more target genes derived from the sample; c) a means for calculating the activity level of the AP-1 transcription factor element in the sample using a calibrated pathway model, wherein the calibrated pathway model compares the expression levels of the at least three target genes in the sample with expression levels of the at least three target genes in the calibrated pathway model which define an activity level of the AP-1 transcription factor element; d) a means for calculating the activity level of the MAPK-AP-1 cellular signaling pathway in the sample based on the calculated activity level of AP-1 transcription factor element in the sample; a means for assigning a MAPK-AP-1 cellular signaling pathway activity status to the calculated activity level of the MAPK-AP-1 cellular signaling pathway in the sample, wherein the activity status is indicative of either an active MAPK-AP-1 cellular signaling pathway or a passive MAPK-AP-1 cellular signaling pathway; and f) a means for displaying the MAPK-AP-1 signaling pathway activity status.

MAPK-AP-1 Mediated Diseases and Disorders and Methods of Treatment

As contemplated herein, the methods and apparatuses of the present invention can be utilized to assess MAPK-AP-1 cellular signaling pathway activity in a subject, for example a subject suspected of having, or having, a disease or disorder wherein the status of the MAPK-AP-1 signaling pathway is probative, either wholly or partially, of disease presence or progression. In one embodiment, provided herein is a method of treating a subject comprising receiving information regarding the activity status of a MAPK-AP-1 cellular signaling pathway derived from a sample isolated from the subject using the methods described herein and administering to the subject a MAPK-AP-1 inhibitor if the information regarding the level of MAPK-AP-1 cellular signaling pathway is indicative of an active MAPK-AP-1 signaling pathway. In a particular embodiment, the MAPK-AP-1 cellular signaling pathway activity indication is set at a cutoff value of odds of the MAPK-AP-1 cellular signaling pathway being active of 10:1, 5:1, 4:1, 2:1, 1:1, 1:2, 1:4, 1:5, 1:10. MAPK-AP-1 inhibitors are known and include, but are not limited to, SP600125, PD98059, PD184352, U0126, Ro092210, or LLZ16402.

The sample(s) to be used in accordance with the present invention can be an extracted sample, that is, a sample that has been extracted from the subject. Examples of the sample include, but are not limited to, a tissue, cells, blood and/or a body fluid of a subject. It can be, e.g., a sample obtained from a cancer lesion, or from a lesion suspected for cancer, or from a metastatic tumor, or from a body cavity in which fluid is present which is contaminated with cancer cells (e.g., pleural or abdominal cavity or bladder cavity), or from other body fluids containing cancer cells, and so forth, for example, via a biopsy procedure or other sample extraction procedure. The cells of which a sample is extracted may also be tumorous cells from hematologic malignancies (such as leukemia or lymphoma). In some cases, the cell sample may also be circulating tumor cells, that is, tumor cells that have entered the bloodstream and may be extracted using suitable isolation techniques, e.g., apheresis or conventional venous blood withdrawal. Aside from blood, a body fluid of which a sample is extracted may be urine, gastrointestinal contents, or anextravasate.

In one aspect of the present invention, the methods and apparatuses described herein are used to identify an active MAPK-AP-1 cellular signaling pathway in a subject suffering from a cancer, and administering to the subject an anti-cancer agent, for example a MAPK-AP-1 inhibitor, selected from, but not limited to, SP600125, PD98059, PD184352, U0126, Ro092210, or LLZ16402.

Another aspect of the present invention relates to a method (as described herein), further comprising:

determining whether the MAPK-AP-1 cellular signaling pathway is operating abnormally in the subject based on the calculated activity of the MAPK-AP-1 cellular signaling pathway in the subject.

Here, the term "abnormally" denotes disease-promoting activity of the MAPK-AP-1 cellular signaling pathway, for example, a tumor-promoting activity.

The present invention also relates to a method (as described herein) further comprising:

recommending prescribing a drug, for example, a MAPK-AP-1 inhibitor, for the subject that corrects for abnormal operation of the MAPK-AP-1 cellular signaling pathway, wherein the recommending is performed if the MAPK-AP-1 cellular signaling pathway is determined to be operating abnormally in the subject based on the calculated/determined activity of the MAPK-AP-1 cellular signaling pathway.

The present invention also relates to a method (as described herein), wherein the calculating/determining comprises:

calculating the activity of the MAPK-AP-1 cellular signaling pathway in the subject based at least on expression levels of two, three or more target genes of a set of target genes of the MAPK-AP-1 cellular signaling pathway measured in the sample of the subject.

The present invention as described herein can, e.g., also advantageously be used in connection with:

diagnosis based on the determined activity of the MAPK-AP-1 cellular signaling pathway in the subject;

prognosis based on the determined activity of the MAPK-AP-1 cellular signaling pathway in the subject;

drug prescription based on the determined activity of the MAPK-AP-1 cellular signaling pathway in the subject;

prediction of drug efficacy based on the determined activity of the MAPK-AP-1 cellular signaling pathway in the subject;

prediction of adverse effects based on the determined activity of the MAPK-AP-1 cellular signaling pathway in the subject;

monitoring of drug efficacy;

drug development;

assay development;

pathway research;

cancer staging;

enrollment of the subject in a clinical trial based on the determined activity of the MAPK-AP-1 cellular signaling pathway in the subject;

selection of subsequent test to be performed; and selection of companion diagnostics tests.

Further advantages will be apparent to those of ordinary skill in the art upon reading and understanding the attached figures, the following description and, in particular, upon reading the detailed examples provided herein below.

It shall be understood that an embodiment of the present invention can also be any combination of the dependent claims or above embodiments with the respective independent claim.

These and other aspects of the invention will be apparent from and elucidated with reference to the embodiments described hereinafter.

EXAMPLES

The following examples merely illustrate exemplary methods and selected aspects in connection therewith. The teaching provided therein may be used for constructing several tests and/or kits, e.g., to detect, predict and/or diagnose the abnormal activity of the MAPK-AP-1 cellular signaling pathway. Furthermore, upon using methods as described herein drug prescription can advantageously be guided, drug response prediction and monitoring of drug efficacy (and/or adverse effects) can be made, drug resistance can be predicted and monitored, e.g., to select subsequent test(s) to be performed (like a companion diagnostic test). The following examples are not to be construed as limiting the scope of the present invention.

Example 1: Mathematical Model Construction

As described in detail in the published international patent application WO 2013/011479 A2 ("Assessment of cellular signaling pathway activity using probabilistic modeling of target gene expression"), by constructing a probabilistic model, e.g., a Bayesian network model, and incorporating conditional probabilistic relationships between expression levels of at least three, for example, at least four, at least five, at least six, at least seven, at least nine, at least ten or more target genes of a cellular signaling pathway, herein, the MAPK-AP-1 cellular signaling pathway, and the level of a transcription factor (TF) element, herein, the AP-1 TF element, the TF element controlling transcription of the at least three target genes of the cellular signaling pathway, such a model may be used to determine the activity of the cellular signaling pathway with a high degree of accuracy. Moreover, the probabilistic model can be readily updated to incorporate additional knowledge obtained by later clinical studies, by adjusting the conditional probabilities and/or adding new nodes to the model to represent additional information sources. In this way, the probabilistic model can be updated as appropriate to embody the most recent medical knowledge.

In another easy to comprehend and interpret approach described in detail in the published international patent application WO 2014/102668 A2 ("Assessment of cellular signaling pathway activity using linear combination(s) of target gene expressions"), the activity of a cellular signaling pathway, herein, the MAPK-AP-1 cellular signaling pathway, may be determined by constructing and evaluating a linear or (pseudo-)linear model incorporating relationships between expression levels of at least three, for example, at least four, at least five, at least six, at least seven, at least nine, at least ten or more target genes of the cellular signaling pathway and the level of a transcription factor (TF) element, herein, the AP-1 TF element, the TF element controlling transcription of the at least three target genes of the cellular signaling pathway, the model being based at least in part on one or more linear combination(s) of expression levels of the at least three target genes.

In both approaches, the expression levels of the at least three target genes may, for example, be measurements of the level of mRNA, which can be the result of, e.g., (RT)-PCR and microarray techniques using probes associated with the target genes mRNA sequences, and of RNA-sequencing. In another embodiment, the expression levels of the at least three target genes can be measured by protein levels, e.g., the concentrations and/or activity of the protein(s) encoded by the target genes.

The aforementioned expression levels may optionally be converted in many ways that might or might not suit the application better. For example, four different transformations of the expression levels, e.g., microarray-based mRNA levels, may be:

- "continuous data", i.e., expression levels as obtained after preprocessing of microarrays using well known algorithms such as MAS5.0 and fRMA,
- "z-score", i.e., continuous expression levels scaled such that the average across all samples is 0 and the standard deviation is 1,
- "discrete", i.e., every expression above a certain threshold is set to 1 and below it to 0 (e.g., the threshold for a probeset may be chosen as the (weighted) median of its value in a set of a number of positive and the same number of negative clinical samples),
- "fuzzy", i.e., the continuous expression levels are converted to values between 0 and 1 using a sigmoid function of the following format: 1/(1+exp((thr−expr)/se)), with expr being the continuous expression levels, thr being the threshold as mentioned before and se being a softening parameter influencing the difference between 0 and 1.

One of the simplest linear models that can be constructed is a model having a node representing the transcription factor (TF) element, herein, the AP-1 TF element, in a first layer and weighted nodes representing direct measurements of the target genes expression levels, e.g., by one probeset that is particularly highly correlated with the particular target gene, e.g., in microarray or (q)PCR experiments, in a second layer. The weights can be based either on calculations from a training data set or based on expert knowledge. This approach of using, in the case where possibly multiple expression levels are measured per target gene (e.g., in the case of microarray experiments, where one target gene can be measured with multiple probesets), only one expression level per target gene is particularly simple. A specific way of selecting the one expression level that is used for a particular target gene is to use the expression level from the probeset that is able to separate active and passive samples of a training data set the best. One method to determine this probeset is to perform a statistical test, e.g., the t-test, and select the probeset with the lowest p-value. The training data set's expression levels of the probeset with the lowest p-value is by definition the probeset with the least likely probability that the expression levels of the (known) active and passive samples overlap. Another selection method is based on odds-ratios. In such a model, one or more expression level(s) are provided for each of the at least three target genes and the one or more linear combination(s) comprise a linear combination including for each of the at least three target genes a weighted term, each weighted term being based on only one expression level of the one or more expression level(s) provided for the respective target gene. If the only one expression level is chosen per target gene as described above, the model may be called a "most discriminant probesets" model.

In an alternative to the "most discriminant probesets" model, it is possible, in the case where possibly multiple expression levels are measured per target gene, to make use of all the expression levels that are provided per target gene. In such a model, one or more expression level(s) are provided for each of the at least three target genes and the one or more linear combination(s) comprise a linear combination of all expression levels of the one or more expression level(s) provided for the at least three target genes. In other words, for each of the at least three target genes, each of the one or more expression level(s) provided for the respective target gene may be weighted in the linear combination by its own (individual) weight. This variant may be called an "all probesets" model. It has an advantage of being relatively simple while making use of all the provided expression levels.

Both models as described above have in common that they are what may be regarded as "single-layer" models, in which the level of the TF element is calculated based on a linear combination of expression levels of the one or more probeset of the one or more target genes.

After the level of the TF element, herein, the AP-1 TF element, has been determined by evaluating the respective model, the determined TF element level can be thresholded in order to infer the activity of the cellular signaling pathway, herein, the MAPK-AP-1 cellular signaling pathway. An exemplary method to calculate such an appropriate threshold is by comparing the determined TF element levels w/c of training samples known to have a passive cellular signaling pathway and training samples with an active cellular signaling pathway. A method that does so and also takes into account the variance in these groups is given by using a threshold $$thr = \frac{\sigma_{wlc_{pas}}\mu_{wlc_{act}} + \sigma_{wlc_{act}}\mu_{wlc_{pas}}}{\sigma_{wlc_{pas}} + \sigma_{wlc_{act}}} \quad (1)$$

where σ and μ are the standard deviation and the mean of the determined TF element levels wlc for the training samples. In case only a small number of samples are available in the active and/or passive training samples, a pseudocount may be added to the calculated variances based on the average of the variances of the two groups:

$$\tilde{v} = \frac{v_{wlc_{act}} + v_{wlc_{pas}}}{2} \quad (2)$$

-continued $$\tilde{v}_{wlc_{act}} = \frac{x\tilde{v} + (n_{act} - 1)v_{wlc_{act}}}{x + n_{act} - 1}$$

$$\tilde{v}_{wlc_{pas}} = \frac{x\tilde{v} + (n_{pas} - 1)v_{wlc_{pas}}}{x + n_{pas} - 1}$$

where v is the variance of the determined TF element levels wlc of the groups, x is a positive pseudocount, e.g., 1 or 10, and $n_{act}$ and $n_{pas}$ are the number of active and passive samples, respectively. The standard deviation σ can next be obtained by taking the square root of the variance v.

The threshold can be subtracted from the determined TF element levels wlc for ease of interpretation, resulting in a cellular signaling pathway's activity score in which negative values correspond to a passive cellular signaling pathway and positive values correspond to an active cellular signaling pathway.

As an alternative to the above-described "single-layer" models, a "two-layer" may also be used in an example. In such a model, a summary value is calculated for every target gene using a linear combination based on the measured intensities of its associated probesets ("first (bottom) layer"). The calculated summary value is subsequently combined with the summary values of the other target genes of the cellular signaling pathway using a further linear combination ("second (upper) layer"). Again, the weights can be either learned from a training data set or based on expert knowledge or a combination thereof. Phrased differently, in the "two-layer" model, one or more expression level(s) are provided for each of the at least three target genes and the one or more linear combination(s) comprise for each of the at least three target genes a first linear combination of all expression levels of the one or more expression level(s) provided for the respective target gene ("first (bottom) layer"). The model is further based at least in part on a further linear combination including for each of the at least three target genes a weighted term, each weighted term being based on the first linear combination for the respective target gene ("second (upper) layer").

The calculation of the summary values can, in an exemplary version of the "two-layer" model, include defining a threshold for each target gene using the training data and subtracting the threshold from the calculated linear combination, yielding the target gene summary. Here the threshold may be chosen such that a negative target gene summary value corresponds to a down-regulated target gene and that a positive target gene summary value corresponds to an up-regulated target gene. Also, it is possible that the target gene summary values are transformed using, e.g., one of the above-described transformations (fuzzy, discrete, etc.), before they are combined in the "second (upper) layer".

After the level of the TF element has been determined by evaluating the "two-layer" model, the determined TF element level can be thresholded in order to infer the activity of the cellular signaling pathway, as described above.

In the following, the models described above are collectively denoted as "(pseudo-) linear" models. A more detailed description of the training and use of probabilistic models, e.g., a Bayesian network model, is provided in Example 3 below.

Example 2: Selection of Target Genes

A transcription factor (TF) is a protein complex (i.e., a combination of proteins bound together in a specific structure) or a protein that is able to regulate transcription from target genes by binding to specific DNA sequences, thereby controlling the transcription of genetic information from DNA to mRNA. The mRNA directly produced due to this action of the TF complex is herein referred to as a "direct target gene" (of the transcription factor). Cellular signaling pathway activation may also result in more secondary gene transcription, referred to as "indirect target genes". In the following, (pseudo-)linear models or Bayesian network models (as exemplary mathematical models) comprising or consisting of direct target genes as direct links between cellular signaling pathway activity and mRNA level, are exemplified, however the distinction between direct and indirect target genes is not always evident. Herein, a method to select direct target genes using a scoring function based on available scientific literature data is presented. Nonetheless, an accidental selection of indirect target genes cannot be ruled out due to limited information as well as biological variations and uncertainties. In order to select the target genes, the MEDLINE database of the National Institute of Health herein further referred to as "Pubmed" was employed to generate a lists of target genes. Furthermore, one additional list of target genes was selected based on the probative nature of their expression.

Publications containing putative AP-1 target genes were searched for by using queries such as ("AP-1" AND "target gene") in the period of the first and second quarter of 2017. Care was taken to search for target genes for the different possible AP-1 dimers, e.g., different combinations of members of the Jun and Fos family. The resulting publications were further analyzed manually following the methodology described in more detail below.

Specific cellular signaling pathway mRNA target genes were selected from the scientific literature, by using a ranking system in which scientific evidence for a specific target gene was given a rating, depending on the type of scientific experiments in which the evidence was accumulated. While some experimental evidence is merely suggestive of a gene being a direct target gene, like for example an mRNA increasing as detected by means of an increasing intensity of a probeset on a microarray of a cell line in which it is known that the MAPK-AP-1 cellular signaling pathway is active, other evidence can be very strong, like the combination of an identified AP-1 cellular signaling pathway TF binding site and retrieval of this site in a chromatin immunoprecipitation (ChIP) assay after stimulation of the specific cellular signaling pathway in the cell and increase in mRNA after specific stimulation of the cellular signaling pathway in a cell line.

Several types of experiments to find specific cellular signaling pathway target genes can be identified in the scientific literature:

1. ChIP experiments in which direct binding of a TF of the cellular signaling pathway of interest to its binding site on the genome is shown. Example: By using chromatin immunoprecipitation (ChIP) technology subsequently putative functional AP-1 TF binding sites in the DNA of cell lines with and without active induction of the MAPK-AP-1 cellular signaling pathway, e.g., by stimulation with TPA, were identified, as a subset of the binding sites recognized purely based on nucleotide sequence. Putative functionality was identified as ChIP-derived evidence that the TF was found to bind to the DNA binding site.
2. Electrophoretic Mobility Shift (EMSA) assays which show in vitro binding of a TF to a fragment of DNA containing the binding sequence. Compared to ChIP-based evidence EMSA-based evidence is less strong, since it cannot be translated to the in vivo situation.

3. Stimulation of the cellular signaling pathway and measuring mRNA expression using a microarray, RNA sequencing, quantitative PCR or other techniques, using MAPK-AP-1 cellular signaling pathway-inducible cell lines and measuring mRNA profiles measured at least one, but preferably several time points after induction—in the presence of cycloheximide, which inhibits translation to protein, thus the induced mRNAs are assumed to be direct target genes.
4. Similar to 3, but alternatively measure the mRNAs expression further downstream with protein abundance measurements, such as western blot.
5. Identification of TF binding sites in the genome using a bioinformatics approach. Example for the AP-1 TF element: Using the binding motif TGA G/C TCA (TRE), the potential binding sites were identified in gene promoter regions.
6. Similar as 3, only in the absence of cycloheximide.
7. Similar to 4, only in the absence of cycloheximide.

In the simplest form one can give every potential gene 1 point for each of these experimental approaches in which the gene was identified as being a target gene of the AP-1 family of transcription factors. Using this relative ranking strategy, one can make a list of most reliable target genes.

Alternatively, ranking in another way can be used to identify the target genes that are most likely to be direct target genes, by giving a higher number of points to the technology that provides most evidence for an in vivo direct target gene. In the list above, this would mean 7 points for experimental approach 1), 6 for 2), and going down to 1 point for experimental approach 7). Such a list may be called a "general list of target genes".

Furthermore, a distinction between evidence from experiments on human tissue/cell lines and animal tissue/cell lines can be made, by giving "human" evidence more weight, compared to "animal" evidence.

Despite the biological variations and uncertainties, the inventors assumed that the direct target genes are the most likely to be induced in a tissue-independent manner. A list of these target genes may be called an "evidence curated list of target genes". Such an evidence curated list of target genes has been used to construct computational models of the MAPK-AP-1 cellular signaling pathway that can be applied to samples coming from different tissue sources.

The following will illustrate exemplary how the selection of an evidence curated target gene list specifically was constructed for the MAPK-AP-1 cellular signaling pathway.

A scoring function was introduced that gave a point for each type of experimental evidence, such as ChIP, EMSA, differential expression, knock down/out, luciferase gene reporter assay, sequence analysis, that was reported in a publication. Further analysis was performed to allow only for genes that had diverse types of experimental evidence and not only one type of experimental evidence, e.g., differential expression. Those genes that had more than one type of experimental evidence available and for which a TF binding site was identified were selected (as shown in Table 1).

A further selection of the evidence curated list of target genes (listed in Table 2) was made by the inventors. The target genes of the evidence curated list that were proven to be more probative in determining the activity of the MAPK-AP-1 cellular signaling pathway from the training samples were selected. Herein, available expression data sets of TPA treated cell lines, i.e., a subset of samples from data sets GSE8742, GSE28878, GSE40117, GSE45417, GSE58235, GSE66853, and EMTAB2091 were used. The cells that were treated with TPA were MAPK-AP-1 active and cells that were treated with a control were MAPK-AP-1 inactive. The gene expression values for the "evidence curated list of target genes" (24 target genes list) from Table 1 were compared between AP-1 active and inactive samples from the GSE8742, GSE28878, GSE40117, GSE45417, GSE58235, GSE66853, and EMTAB2091 data sets. If the expression level of a target gene was obviously differentiated between the pathway active and inactive groups, which signifies that the target gene can be used to distinguish between the pathway active and inactive groups, then the target gene was selected. This resulted in the "11 target genes shortlist" for the MAPK-AP-1 model" shown in Table 2.

TABLE 1

"Evidence curated list of target genes" (24 target genes list) of the MAPK-AP-1 cellular signaling pathway used in the MAPK-AP-1 cellular signaling pathway models and associated probesets used to measure the mRNA expression level of the target genes.

| Target gene | Probeset | Score | Target gene | Probeset | Score |
|---|---|---|---|---|---|
| BCL2L11 | 1553096_s_at | 4 | FASLG | 210865_at | 4 |
| | 208536_s_at | | | 211333_s_at | |
| | 1553088_a_at | | FIGF | 206742_at | 3 |
| | 1561844_at | | GLRX | 206662_at | 3 |
| | 1555372_at | | | 209276_s_at | |
| | 222343_at | | IL2 | 207849_at | 4.5 |
| | 1558143_a_at | | IVL | 214599_at | 4 |
| | 225606_at | | LOR | 207720_at | 3 |
| CCND1 | 214019_at | 4 | MMP1 | 204475_at | 6 |
| | 208711_s_at | | MMP3 | 205828_at | 4 |
| | 208712_at | | MMP9 | 203936_s_at | 5 |
| DDIT3 | 209383_at | 3 | SERPINE1 | 202627_s_at | 5.5 |
| DNMT1 | 201697_s_at | 3.5 | | 202628_s_at | |
| EGFR | 210984_x_at | 5.5 | PLAU | 211668_s_at | 3.5 |
| | 201983_s_at | | | 205479_s_at | |
| | 211550_at | | PLAUR | 214866_at | 4.5 |
| | 211607_x_at | | | 210845_s_at | |
| | 201984_s_at | | | 211924_s_at | |
| | 211551_at | | PTGS2 | 204748_at | 3 |
| | 1565483_at | | | 1554997_a_at | |
| | 1565484_x_at | | SNCG | 209877_at | 6 |
| ENPP2 | 209392_at | 5 | TIMP1 | 201666_at | 5 |
| | 210839_s_at | | TP53 | 201746_at | 3 |
| EZR | 208621_s_at | 3.5 | | 211300_s_at | |
| | 208622_s_at | | VIM | 201426_s_at | 4.5 |
| | 208623_s_at | | | | |
| | 217234_s_at | | | | |

TABLE 2

"11 target genes shortlist" of AP-1 target genes based on the evidence curated list of AP-1 target genes. (The associated probesets are the same as in Table 1.)

| Target gene | Probeset | Score | Target gene | Probeset | Score |
|---|---|---|---|---|---|
| CCND1 | 214019_at | 4 | GLRX | 206662_at | 3 |
| | 208711_s_at | | | 209276_s_at | |
| | 208712_at | | MMP1 | 204475_at | 6 |
| EGFR | 210984_x_at | 5.5 | MMP3 | 205828_at | 4 |
| | 201983_s_at | | PLAU | 211668_s_at | 3.5 |
| | 211550_at | | | 205479_s_at | |
| | 211607_x_at | | PLAUR | 214866_at | 4.5 |
| | 201984_s_at | | | 210845_s_at | |
| | 211551_at | | | 211924_s_at | |
| | 1565483_at | | SERPINE1 | 202627_s_at | 5.5 |
| | 1565484_x_at | | | 202628_s_at | |

TABLE 2-continued

"11 target genes shortlist" of AP-1 target genes based on the evidence curated list of AP-1 target genes. (The associated probesets are the same as in Table 1.)

| Target gene | Probeset | Score | Target gene | Probeset | Score |
|---|---|---|---|---|---|
| EZR | 208621_s_at | 3.5 | SNCG | 209877_at | 6 |
| | 208622_s_at | | TIMP1 | 201666_at | 5 |
| | 208623_s_at | | | | |
| | 217234_s_at | | | | |

Example 3: Training and Using the Mathematical Model

Before the mathematical model can be used to infer the activity of the cellular signaling pathway, herein, the MAPK-AP-1 cellular signaling pathway, in a subject, the model must be appropriately trained.

If the mathematical model is a probabilistic model, e.g., a Bayesian network model, based at least in part on conditional probabilities relating the AP-1 TF element and expression levels of the at least three target genes of the MAPK-AP-1 cellular signaling pathway measured in a sample, the training may preferably be performed as described in detail in the published international patent application WO 2013/011479 A2 ("Assessment of cellular signaling pathway activity using probabilistic modeling of target gene expression").

If the mathematical model is based at least in part on one or more linear combination(s) of expression levels of the at least three target genes of the MAPK-AP-1 cellular signaling pathway measured in the sample, the training may preferably be performed as described in detail in the published international patent application WO 2014/102668 A2 ("Assessment of cellular signaling pathway activity using linear combination(s) of target gene expressions").

Herein, an exemplary Bayesian network model as shown in FIG. 2 was used to model the transcriptional program of the MAPK-AP-1 cellular signaling pathway in a simple manner. The model consists of three types of nodes: (a) a transcription factor (TF) element (with states "absent" and "present") in a first layer 1; (b) target genes TG1, TG2, TGn (with states "down" and "up") in a second layer 2, and; (c) measurement nodes linked to the expression levels of the target genes in a third layer 3. These can be microarray probesets $PS_{1,1}$, $PS_{1,2}$, $PS_{1,3}$, $PS_{2,1}$, $PS_{n,1}$, $PS_{n,m}$ (with states "low" and "high"), as preferably used herein, but could also be other gene expression measurements such as RNAseq or RT-qPCR.

A suitable implementation of the mathematical model, herein, the exemplary Bayesian network model, is based on microarray data. The model describes (i) how the expression levels of the target genes depend on activation of the TF element, and (ii) how probeset intensities, in turn, depend on the expression levels of the respective target genes. For the latter, probeset intensities may be taken from fRMA pre-processed Affymetrix HG-U133Plus2.0 microarrays, which are widely available from the Gene Expression Omnibus (GEO) and ArrayExpress.

As the exemplary Bayesian network model is a simplification of the biology of a cellular signaling pathway, herein, the MAPK-AP-1 cellular signaling pathway, and as biological measurements are typically noisy, a probabilistic approach was opted for, i.e., the relationships between (i) the TF element and the target genes, and (ii) the target genes and their respective probesets, are described in probabilistic terms. Furthermore, it was assumed that the activity of the oncogenic cellular signaling pathway which drives tumor growth is not transiently and dynamically altered, but long term or even irreversibly altered. Therefore the exemplary Bayesian network model was developed for interpretation of a static cellular condition. For this reason complex dynamic cellular signaling pathway features were not incorporated into the model.

Once the exemplary Bayesian network model is built and calibrated (see below), the model can be used on microarray data of a new sample by entering the probeset measurements as observations in the third layer 3, and inferring backwards in the calibrated pathway model what the probability must have been for the TF element to be "present". Here, "present" is considered to be the phenomenon that the TF element is bound to the DNA and is controlling transcription of the cellular signaling pathway's target genes, and "absent" the case that the TF element is not controlling transcription. This probability is hence the primary read-out that may be used to indicate activity of the cellular signaling pathway, herein, the MAPK-AP-1 cellular signaling pathway, which can next be translated into the odds of the cellular signaling pathway being active by taking the ratio of the probability of it being active vs. it being passive (i.e., the odds are given by $p/(1-p)$, where p is the predicted probability of the cellular signaling pathway being active).

In the exemplary Bayesian network model, the probabilistic relations have been made quantitative to allow for a quantitative probabilistic reasoning. In order to improve the generalization behavior across tissue types, the parameters describing the probabilistic relationships between (i) the TF element and the target genes have been carefully hand-picked. If the TF element is "absent", it is most likely that the target gene is "down", hence a probability of 0.95 is chosen for this, and a probability of 0.05 is chosen for the target gene being "up". The latter (non-zero) probability is to account for the (rare) possibility that the target gene is regulated by other factors or that it is accidentally observed as being "up" (e.g. because of measurement noise). If the TF element is "present", then with a probability of 0.70 the target gene is considered "up", and with a probability of 0.30 the target gene is considered "down". The latter values are chosen this way, because there can be several causes why a target gene is not highly expressed even though the TF element is present, e.g., because the gene's promoter region is methylated. In the case that a target gene is not up-regulated by the TF element, but down-regulated, the probabilities are chosen in a similar way, but reflecting the down-regulation upon presence of the TF element. The parameters describing the relationships between (ii) the target genes and their respective probesets have been calibrated on experimental data. For the latter, in this example, microarray data was used from patients samples which are known to have an active MAPK-AP-1 cellular signaling pathway whereas normal, healthy samples from the same dataset were used as passive MAPK-AP-1 cellular signaling pathway samples, but this could also be performed using cell line experiments or other patient samples with known cellular signaling pathway activity status. The resulting conditional probability tables are given by:

A: For Upregulated Target Genes

| | PSi,j = low | PSi,j = high |
|---|---|---|
| TGi = down | $\frac{AL_{i,j}+1}{AL_{i,j}+AH_{i,j}+2}$ | $\frac{AH_{i,j}+1}{AL_{i,j}+AH_{i,j}+2}$ |

-continued

| | PSi,j = low | PSi,j = high |
|---|---|---|
| TGi = up | $\frac{PL_{i,j}+1}{PL_{i,j}+PH_{i,j}+2}$ | $\frac{PH_{i,j}+1}{PL_{i,j}+PH_{i,j}+2}$ |

B: For Downregulated Target Genes

| | PSi,j = low | PSi,j = high |
|---|---|---|
| TGi = down | $\frac{PL_{i,j}+1}{PL_{i,j}+PH_{i,j}+2}$ | $\frac{PH_{i,j}+1}{PL_{i,j}+PH_{i,j}+2}$ |
| TGi = up | $\frac{AL_{i,j}+1}{AL_{i,j}+AH_{i,j}+2}$ | $\frac{AH_{i,j}+1}{AL_{i,j}+AH_{i,j}+2}$ |

In these tables, the variables $AL_{i,j}$, $AH_{i,j}$, $PL_{i,j}$, and $PH_{i,j}$ indicate the number of calibration samples with an "absent" (A) or "present" (P) transcription complex that have a "low" (L) or "high" (H) probeset intensity, respectively. Dummy counts have been added to avoid extreme probabilities of 0 and 1.

To discretize the observed probeset intensities, for each probeset $PS_{i,j}$ a threshold $t_{i,j}$ was used, below which the observation is called "low", and above which it is called "high". This threshold has been chosen to be the (weighted) median intensity of the probeset in the used calibration dataset. Due to the noisiness of microarray data, a fuzzy method was used when comparing an observed probeset intensity to its threshold, by assuming a normal distribution with a standard deviation of 0.25 (on a log 2 scale) around the reported intensity, and determining the probability mass below and above the threshold.

If instead of the exemplary Bayesian network described above, a (pseudo-)linear model as described in Example 1 above is employed, the weights indicating the sign and magnitude of the correlation between the nodes and a threshold to call whether a node is either "absent" or "present" would need to be determined before the model could be used to infer cellular signaling pathway activity in a test sample. One could use expert knowledge to fill in the weights and the threshold a priori, but typically the model would be trained using a representative set of training samples, of which preferably the ground truth is known, e.g., expression data of probesets in samples with a known "present" transcription factor complex (=active cellular signaling pathway) or "absent" transcription factor complex (=passive cellular signaling pathway).

Known in the field are a multitude of training algorithms (e.g., regression) that take into account the model topology and changes the model parameters, here, the weights and the threshold, such that the model output, here, a weighted linear score, is optimized. Alternatively, it is also possible to calculate the weights directly from the expression observed levels without the need of an optimization algorithm.

A first method, named "black and white"-method herein, boils down to a ternary system, in which each weight is an element of the set $\{-1, 0, 1\}$. If this is put in a biological context, the −1 and 1 correspond to target genes or probesets that are down- and up-regulated in case of cellular signaling pathway activity, respectively. In case a probeset or target gene cannot be statistically proven to be either up- or down-regulated, it receives a weight of 0. In one example, a left-sided and right-sided, two sample t-test of the expression levels of the active cellular signaling pathway samples versus the expression levels of the samples with a passive cellular signaling pathway can be used to determine whether a probe or gene is up- or down-regulated given the used training data. In cases where the average of the active samples is statistically larger than the passive samples, i.e., the p-value is below a certain threshold, e.g., 0.3, the target gene or probeset is determined to be up-regulated. Conversely, in cases where the average of the active samples is statistically lower than the passive samples, the target gene or probeset is determined to be down-regulated upon activation of the cellular signaling pathway. In case the lowest p-value (left- or right-sided) exceeds the aforementioned threshold, the weight of the target gene or probeset can be defined to be 0.

A second method, named "log odds"-weights herein, is based on the logarithm (e.g., base e) of the odds ratio. The odds ratio for each target gene or probeset is calculated based on the number of positive and negative training samples for which the probeset/target gene level is above and below a corresponding threshold, e.g., the (weighted) median of all training samples. A pseudo-count can be added to circumvent divisions by zero. A further refinement is to count the samples above/below the threshold in a somewhat more probabilistic manner, by assuming that the probeset/target gene levels are e.g. normally distributed around its observed value with a certain specified standard deviation (e.g., 0.25 on a 2-log scale), and counting the probability mass above and below the threshold. Herein, an odds ratio calculated in combination with a pseudo-count and using probability masses instead of deterministic measurement values is called a "soft" odds ratio.

Further details regarding the determining of cellular signaling pathway activity using mathematical modeling of target gene expression can be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945.

Herein, we have used publically available data containing cell lines which have been treated with a PKC-activator, e.g., 12-O-Tetradecanoylphorbol-13-acetate (TPA, also called PMA, see, for example, Mudduluru G. et al, "PMA up-regulates the transcription of Ax1 by AP-1 transcription factor binding to TRE sequences via the MAPK cascade in leukaemia cells", Biology of the Cell, Vol. 103, pages 21 to 33, 2010), which increases AP-1 activity. In those data sets samples with TPA-treated cell lines were considered as AP-1 active, while samples containing cell lines which are not treated with TPA, were considered to be AP-1 inactive. The following data sets have been used in the search for calibration samples: From ArrayExpress: EMTAB2091, EMEXP2573, EMEXP2213, EMEXP3107; from the Gene Expression Omnibus: GSE45417, GSE58235, GSE66853, GSE8742, GSE13710, GSE28878, GSE40117. Before selecting calibration samples a quality control was performed on the data sets to ensure that samples were reliable.

To select calibration samples from these data sets the following procedure was followed:

Different subselections of data sets were performed:

- Based on treatment, e.g., only samples on which no other treatment was performed than TPA (AP-1 active) and only samples which were not treated at all (AP-1 inactive).
- Based on tissue type, e.g., by removing all samples that are based on a specific tissue, e.g., liver or blood. Or by selecting only samples that are based on a specific tissue, e.g., liver or blood.

Based on data set: Only samples from a specific data set were included (e.g., GSE28878).

Combinations of the above.

Samples were ranked based on:

The sum of all probeset levels corresponding to the AP-1 target genes from Table 1.

The weighted sum of all probeset levels corresponding to the AP-1 target genes from Table 1.

The top 20 active and top 20 inactive samples were selected as calibration samples. A smaller number of samples was selected if the total number of samples was significantly reduced because of the selection criteria.

For each of the subselections and rankings a model was built.

Each model was run on all the data sets mentioned above.

Samples were classified as active and inactive depending on whether they were treated with TPA or not (ground truth).

For each model the inferred AP-1 activity (log 2odds>0→AP-1=active; log 2odds<0→AP-1=inactive) was compared to the ground truth.

The inferred MAPK-AP-1 cellular signaling pathway activity was assessed using the following criteria:

Balanced accuracy.

Minimum of the differences between the averaged inferred AP-1 activity of active samples and the averaged inferred AP-1 activity of inactive samples (ground truth) from individual data sets. (The rationale behind this is that the difference in inferred AP-1 activity for active and inactive samples within a data set should not be too small.)

Maximum of the differences between the averaged inferred AP-1 activity of active samples and the averaged inferred AP-1 activity of inactive samples (ground truth) from individual data sets. (The rationale behind this is that the difference in inferred AP-1 activity for active and inactive samples within a data set should not be too big.)

Average of the differences between the averaged inferred AP-1 activity of active samples and the averaged inferred AP-1 activity of inactive samples (ground truth) from individual data sets. (The rationale behind this is that a higher average difference in inferred AP-1 activity for active and inactive samples within a data set is preferred.)

Standard deviation of the differences between the averaged inferred AP-1 activity of active samples and the averaged inferred AP-1 activity of inactive samples (ground truth) from individual data sets. (The rationale behind this is that average difference in inferred AP-1 activity for active and inactive samples within a data set is preferably similar.)

The models were ranked based on each of these 5 criteria (1=best model, n=worst model)

All rankings were summed and the model with the lowest total ranking was selected as the final AP-1 model.

The final calibration samples are contained in the following data sets: GSE40117, GSE58235, GSE28878, GSE8742, GSE45417, GSE66853, E-MTAB-2091.

The calibrated model was valided on a number of public datasets from the GEO database which contained a ground truth with respect to AP-1 activity, that is, cell lines in which AP-1 activity was either induced or inhibited (e.g., treated with TPA, or knockdown of one of the AP-1 subunits). As an application example, the model was run on a data set of breast cancer samples and a data set of lung cancer samples.

In the following, validation results of the trained exemplary Bayesian network model using the evidence curated list of target genes (24 target genes list) from Table 1 are shown in FIGS. 9 to 13.

Figure 9:
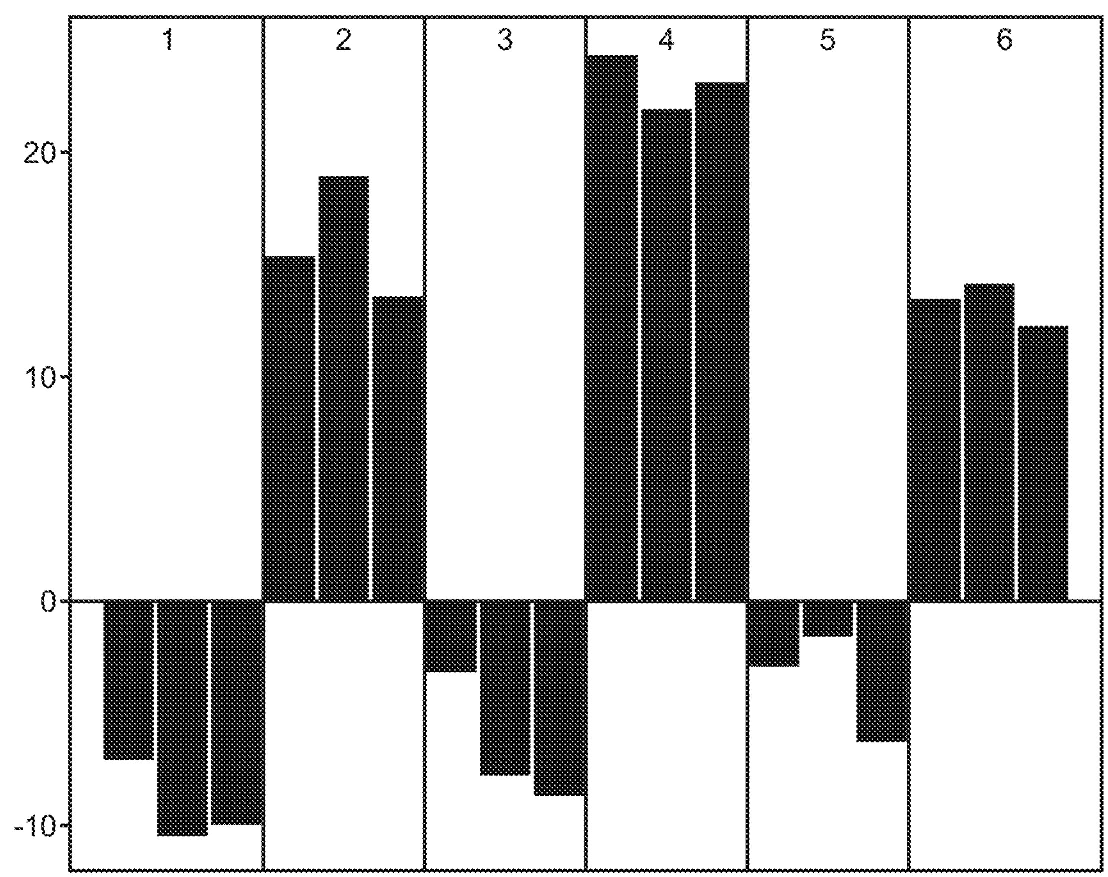
FIG. 9 shows MAPK-AP-1 cellular signaling pathway activity predictions of the trained exemplary Bayesian network model using the evidence curated list of target genes (24 target genes list) from Table 1 on 18 samples taken from GSE28878.

FIG. 9 shows MAPK-AP-1 cellular signaling pathway activity predictions of the trained exemplary Bayesian network model using the evidence curated list of target genes (24 target genes list) from Table 1 on 18 samples taken from GSE28878 (see Magkoufopoulou C. et al., "A transcriptomics-based in vitro assay for predicting chemical genotoxicity in vivo", Carcinogenesis, Vol. 33, No. 7, pages 1421 to 1429, 2012).

A HepG2 cell line was treated with DMSO as control vehicle (group 1: 12 h, all 3 samples are part of the calibration data set; group 3: 24 h, 2 samples are part of the calibration data set; group 5: 48 h, 1 sample is part of the calibration data set) or 500 nM TPA (group 2: 12 h, 1 sample is part of the calibration data set; group 4: 24 h, all 3 samples are part of the calibration data set; group 6: 48 h). In the diagram, the vertical axis indicates the odds (on a log 2 scale) that the TF element is "present" resp. "absent", which corresponds to the MAPK-AP-1 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The MAPK-AP-1 model correctly detects a large increase in AP-1 activity after exposure to TPA.

Figure 10:
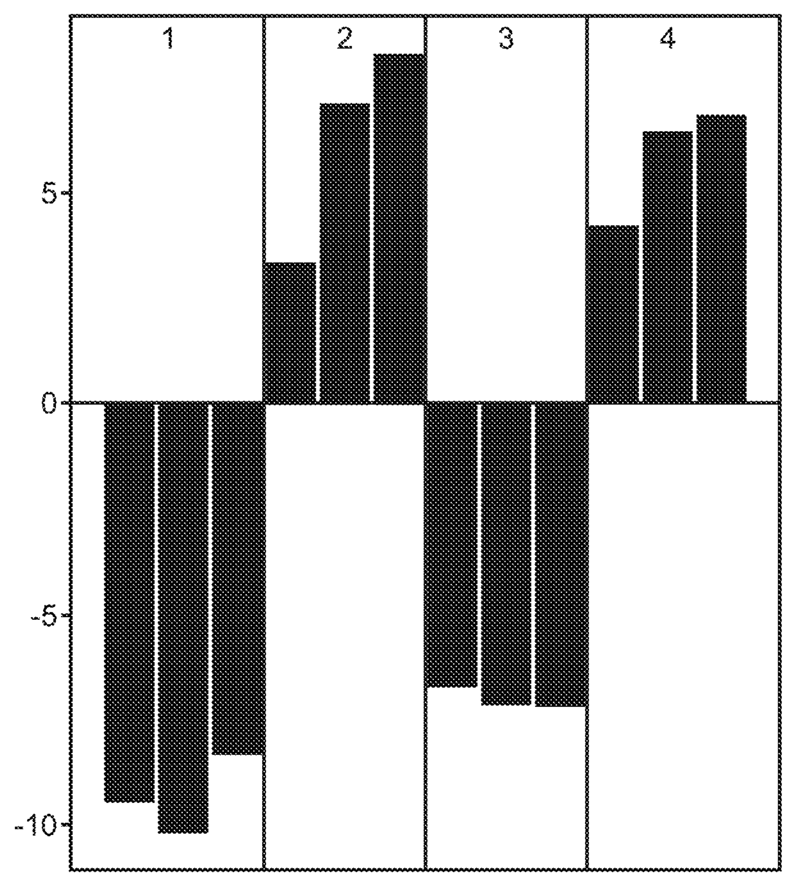
FIG. 10 shows MAPK-AP-1 cellular signaling pathway activity predictions of the trained exemplary Bayesian network model using the evidence curated list of target genes (24 target genes list) from Table 1 on 12 samples taken from GSE45417.

FIG. 10 shows MAPK-AP-1 cellular signaling pathway activity predictions of the trained exemplary Bayesian network model using the evidence curated list of target genes (24 target genes list) from Table 1 on 12 samples taken from GSE45417 (Ramsey J. E. and Fontes J. D., "The Zinc Finger Transcription Factor ZXDC Activates CCL2 Gene Expression by Opposing BCL6-mediated Repression", Molecular Immunology, Vo. 56, No. 4, pages 768 to 780, 2013). The U937 (histiocytic lymphoma) cell line was treated with 0.1% DMSO as control vehicle (group 1: all 3 samples are part of the calibration data set; and group 3), or 100 nM TPA (group 2: all 3 samples are part of the calibration data set; and group 4). Additionally, ZXDC1 knockdown was induced using doxycycline (groups 3 and 4). In the diagram, the vertical axis indicates the odds (on a log 2 scale) that the TF element is "present" resp. "absent", which corresponds to the MAPK-AP-1 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. In both cases, the MAPK-AP-1 model correctly detects a large increase in AP-1 activity after exposure to TPA, independent of ZXDC1 knockdown.

Figure 11:
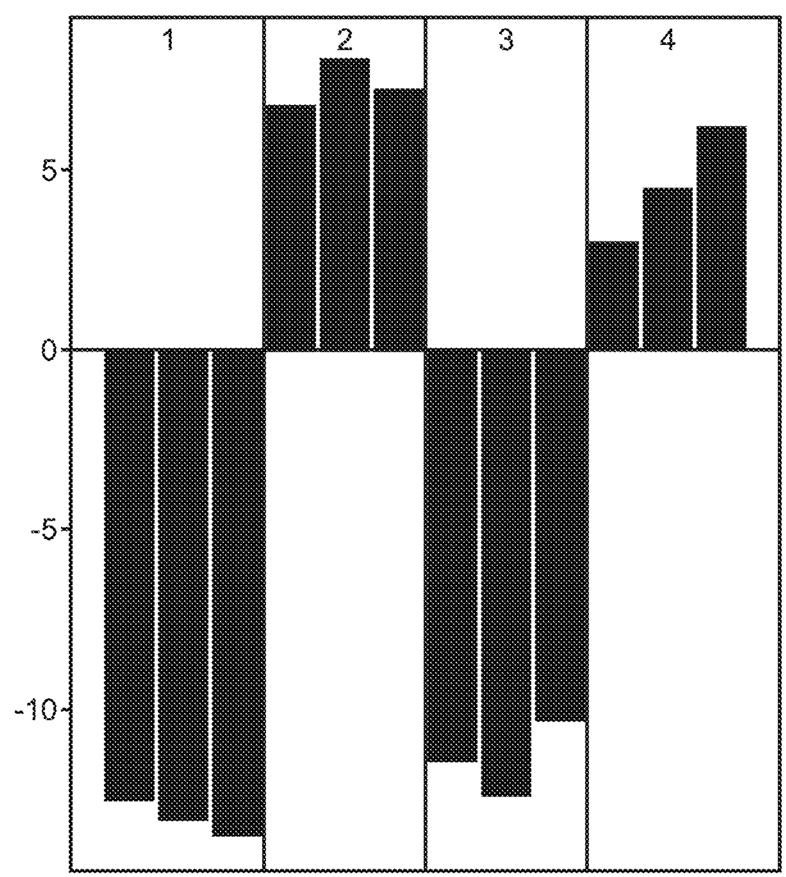
FIG. 11 shows MAPK-AP-1 cellular signaling pathway activity predictions of the trained exemplary Bayesian network model using the evidence curated list of target genes (24 target genes list) from Table 1 on 18 samples taken from GSE66853.

FIG. 11 shows MAPK-AP-1 cellular signaling pathway activity predictions of the trained exemplary Bayesian network model using the evidence curated list of target genes (24 target genes list) from Table 1 on 18 samples taken from GSE66853 (see Steinmetz B. et al., "The oncogene EVI1 enhances transcriptional and biological responses of human myeloid cells to all-trans retinoic acid", Cell Cycle, Vol. 13, No. 18, pages 2931 to 2943, 2014). U937 cells were treated with Ethanol as control vehicle (group 1: all 3 samples are part of the calibration data set; and group 3) or 50 ng/ml TPA (group 2: 1 sample is part of the calibration data set; and group 4) for 24 h. U937 cells were either transduced with an empty vector (groups 1 and 2) or with an EVI1 expression vector (groups 3 and 4). In the diagram, the vertical axis indicates the odds (on a log 2 scale) that the TF element is "present" resp. "absent", which corresponds to the MAPK-AP-1 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. In both cases, the MAPK-AP-1 model correctly detects a large increase in AP-1 activity after exposure to TPA, compared to Ethanol. Although it is known that the FOS and JUN promoter region contains EVI1 binding sites it seems that this effect on AP-1 activity is very small compared to the addition of 50 ng/ml TPA.

Figure 12:
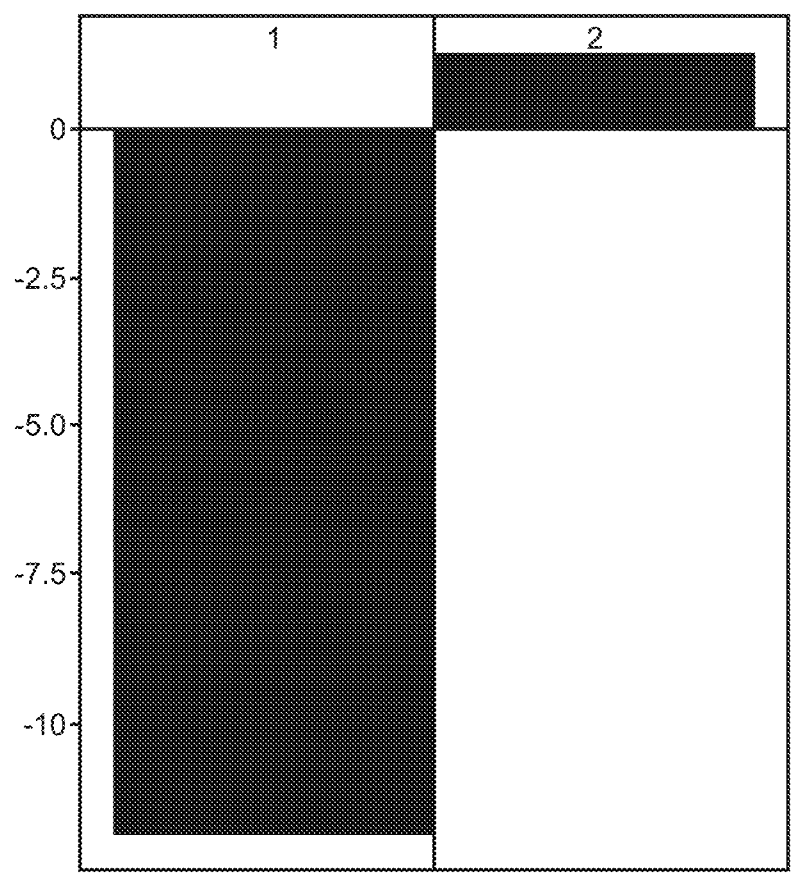
FIG. 12 shows MAPK-AP-1 cellular signaling pathway activity predictions of the trained exemplary Bayesian network model using the evidence curated list of target genes (24 target genes list) from Table 1 on 2 samples taken from E-MEXP-2213

FIG. 12 shows MAPK-AP-1 cellular signaling pathway activity predictions of the trained exemplary Bayesian network model using the evidence curated list of target genes (24 target genes list) from Table 1 on 2 samples taken from E-MEXP-2213 (see Navarro F. et al., "miR-34a contributes to megakaryocytic differentiation of K562 cells independently of p53", Blood, Vol. 114, No. 10, pages 2181 to 2192, 2009). K562 (erythroleukemia) cells were either not treated (group 1) or treated with 10 nM TPA (group 2). In the diagram, the vertical axis indicates the odds (on a log 2 scale) that the TF element is "present" resp. "absent", which corresponds to the MAPK-AP-1 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The MAPK-AP-1 model correctly detects a large increase in AP-1 activity after exposure to TPA.

Figure 13:
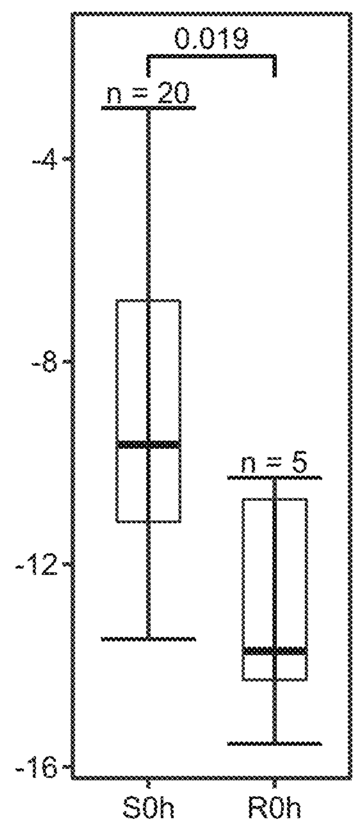
FIG. 13 shows MAPK-AP-1 cellular signaling pathway activity predictions of the trained exemplary Bayesian network model using the evidence curated list of target genes (24 target genes list) from Table 1 on 25 samples taken from GSE2677, GSE2842, and GSE39338.

FIG. 13 shows MAPK-AP-1 cellular signaling pathway activity predictions of the trained exemplary Bayesian network model using the evidence curated list of target genes (24 target genes list) from Table 1 on 25 samples taken from GSE2677, GSE2842 (see Schmidt S. et al., "Identification of glucocorticoid-response genes in children with acute lymphoblastic leukemia", Blood Vol. 107, No. 5, pages 2061 to 2069, 2006), and GSE39338 (see Chen D. W. et al., "Erg and AP-1 as determinants of glucocorticoid response in acute lymphoblastic leukemia", Oncogene, Vol. 32, No. 25, pages 3039 to 3048, 2013). Acute lymphoblastic leukemia (ALL) cells were either glucocorticoid-sensitive (S0h; left) or glucocorticoid-resistant (R0h; right). In the diagram, the vertical axis indicates the odds (on a log 2 scale) that the TF element is "present" resp. "absent", which corresponds to the MAPK-AP-1 cellular signaling pathway being active resp. passive. Chen D. W. et al. found that in glucocorticoid-sensitive cells, c-Jun was significantly induced. The MAPK-AP-1 model correctly detects higher AP-1 activity in glucocorticoid-sensitive cells compared to glucocorticoid-resistant cells.

In the following, validation results of the trained exemplary Bayesian network model using the 11 target gene shortlist from Table 2 are shown in FIGS. 14 to 17.

Figure 14:
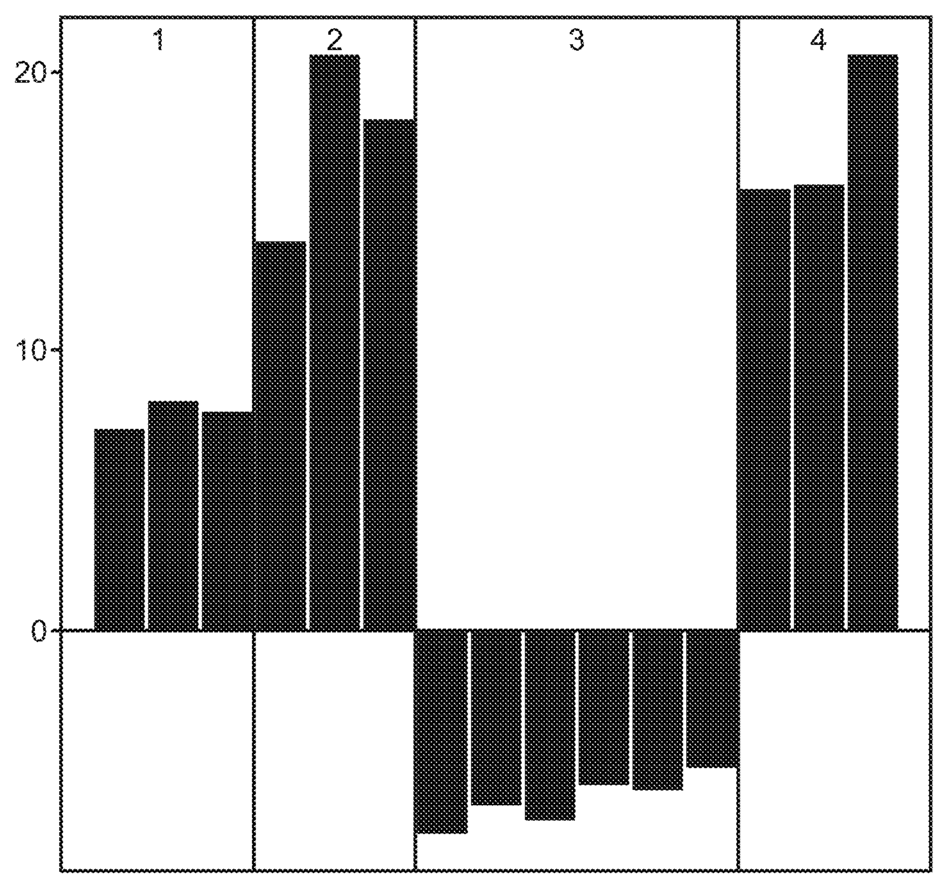
FIG. 14 shows MAPK-AP-1 cellular signaling pathway activity predictions of the trained exemplary Bayesian network model using the 11 target gene shortlist from Table 2 on 15 samples taken from GSE40117.

FIG. 14 shows MAPK-AP-1 cellular signaling pathway activity predictions of the trained exemplary Bayesian network model using the 11 target gene shortlist from Table 2 on 15 samples taken from GSE40117 (see Doktorova T. Y. et al., "Transcriptomic responses generated by hepatocarcinogens in a battery of liver-based in vitro models", Carcinogenesis, Vol. 34, No. 6, pages 1393 to 1402, 2013). Human embryonic stem cell derived hepatocyte like cells (hES-Hep) were treated with 0.11 μM TPA (group 2: all 3 samples are part of the calibration data set) and compared to control conditions (group 1). HepG2 (a human liver cancer cell line) were treated with 0.0001 μM TPA (group 4: 3 samples are part of the calibration data set) and compared to control conditions (group 3: 1 sample is part of the calibration data set). In the diagram, the vertical axis indicates the odds (on a log 2 scale) that the TF element is "present" resp. "absent", which corresponds to the MAPK-AP-1 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. In both cases, the MAPK-AP-1 model correctly detects a large increase in AP-1 activity after exposure to TPA.

Figure 15:
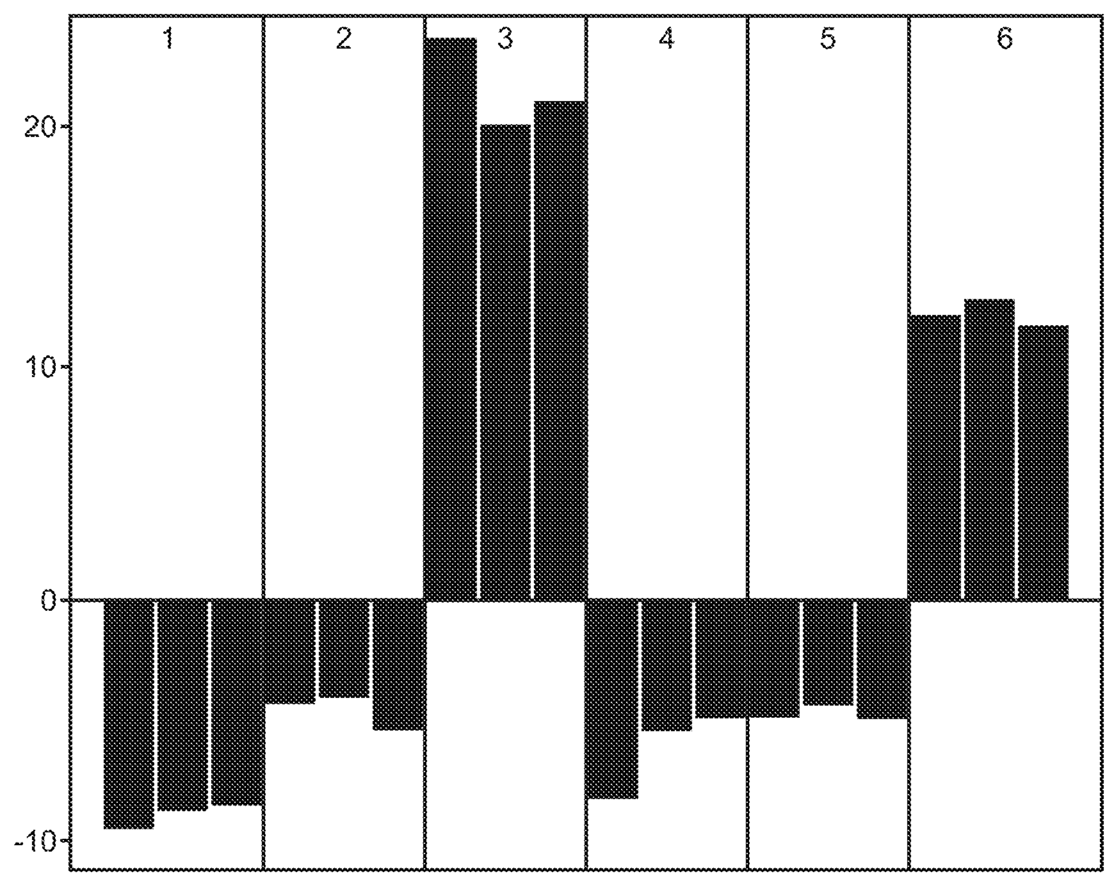
FIG. 15 shows MAPK-AP-1 cellular signaling pathway activity predictions of the trained exemplary Bayesian network model using the 11 target gene shortlist from Table 2 on 18 samples taken from GSE58235.

FIG. 15 shows MAPK-AP-1 cellular signaling pathway activity predictions of the trained exemplary Bayesian network model using the 11 target gene shortlist from Table 2 on 18 samples taken from GSE58235 (see Deferme L. et al., "Oxidative stress mechanisms do not discriminate between genotoxic and nongenotoxic liver carcinogens", Chemical Research in Toxicology, Vol. 28, No. 8, pages 1636 to 1646, 2015). The HepG2 (Human Hepatoma) cell line was treated with 0.5% DMSO (group 1: all 3 samples are part of the calibration data set; group 4: 1 sample is part of the calibration data set), 0.5% Ethanol (groups 2 and 5) or 500 nM TPA (group 3: all 3 samples are part of the calibration data set; and group 6) for 24 hours (groups 1 to 3) or 48 hours (groups 4 to 6). In the diagram, the vertical axis indicates the odds (on a log 2 scale) that the TF element is "present" resp. "absent", which corresponds to the MAPK-AP-1 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. In both cases, the MAPK-AP-1 model correctly detects a large increase in AP-1 activity after exposure to TPA compared to DMSO and Ethanol.

Figure 16:
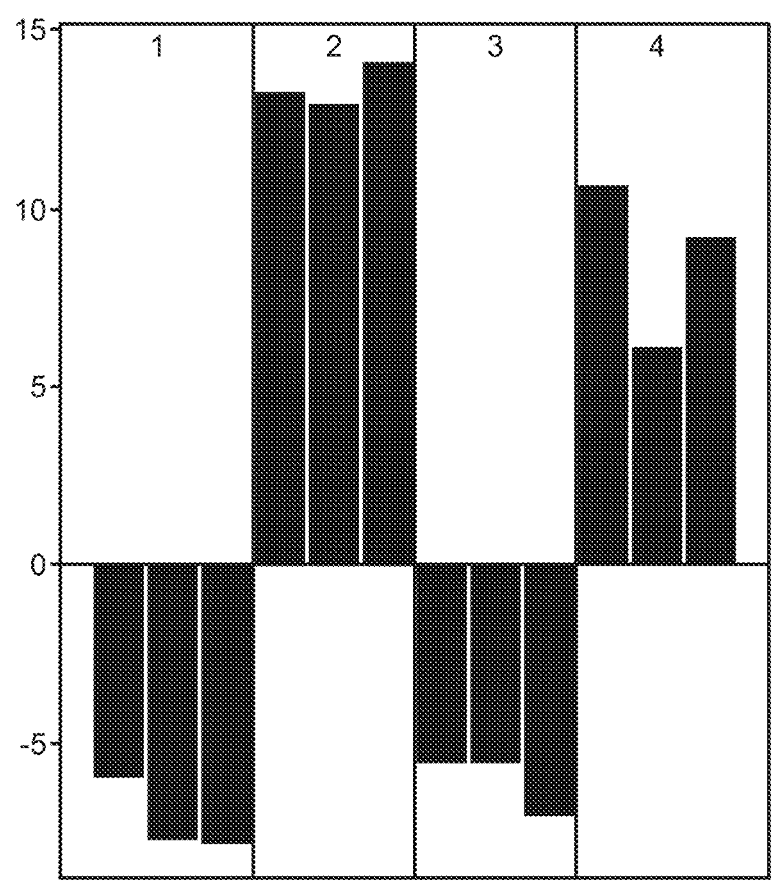
FIG. 16 shows MAPK-AP-1 cellular signaling pathway activity predictions of the trained exemplary Bayesian network model using the 11 target gene shortlist from Table 2 on 12 samples taken from E-MEXP-2573.

FIG. 16 shows MAPK-AP-1 cellular signaling pathway activity predictions of the trained exemplary Bayesian network model using the 11 target gene shortlist from Table 2 on 12 samples taken from E-MEXP-2573 (see Goodfellow S. J. et al., "WT1 and its transcriptional cofactor BASP1 redirect the differentiation pathway of an established blood cell line", Biochemical Journal, Vol. 435, pages 113 to 125, 2011). RNA was extracted from K562 (erythroleukemia) cells after 24 h (groups 1 and 3) or cells were treated with 100 nM TPA for a further 48 h (groups 2 and 4). K562 were either transfected with a control empty vector (groups 1 and 2) or a BASP1-containing vector (groups 3 and 4). In the diagram, the vertical axis indicates the odds (on a log 2 scale) that the TF element is "present" resp. "absent", which corresponds to the MAPK-AP-1 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. In both cases, the MAPK-AP-1 model correctly detects a large increase in AP-1 activity after exposure to TPA.

Figure 17:
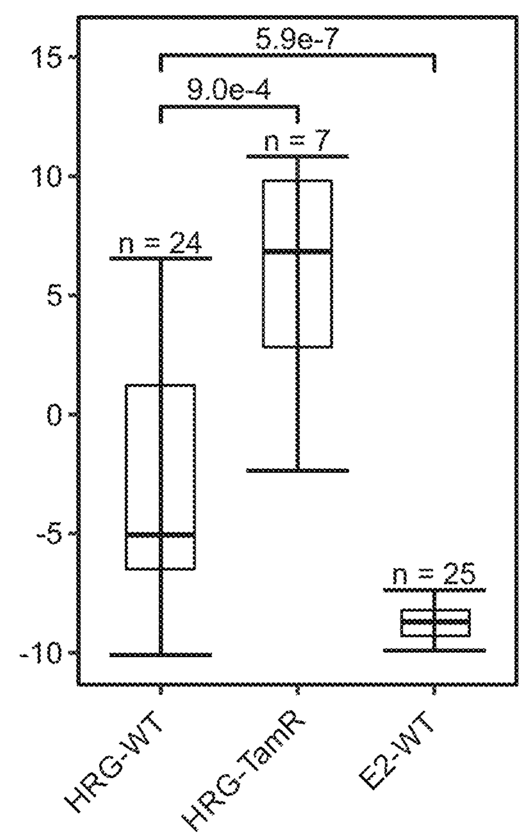
FIG. 17 shows MAPK-AP-1 cellular signaling pathway activity predictions of the trained exemplary Bayesian network model using the 11 target gene shortlist from Table 2 on 56 samples taken from GSE21618.

FIG. 17 shows MAPK-AP-1 cellular signaling pathway activity predictions of the trained exemplary Bayesian network model using the 11 target gene shortlist from Table 2 on 56 samples taken from GSE21618 (Oyama M. et al., "Integrated quantitative analysis of the phosphoproteome and transcriptome in taximofen-resistant breast cancer", The Journal Of Biological Chemistry, Vol. 286, No. 1, pages 818 to 829, 2011). MCF-7 human breast cancer cell line was either kept as wild type (HRG-WT; left) or made tamoxifen-resistant and stimulated with heregulin (HRG-TamR; middle) or stimulated with 17β-estradiol (E2-WT; right). In the diagram, the vertical axis indicates the odds (on a log 2 scale) that the TF element is "present" resp. "absent", which corresponds to the MAPK-AP-1 cellular signaling pathway being active resp. passive. Oyama M. et al. found that JUN family (c-JUN, JUNB, and JUNB) motifs had a higher score in HRG-stimulated TamR cells than in WT cells, but that their regulation was opposite in the E2-stimulated cells. Indeed, the MAPK-AP-1 model finds a higher AP-1 activity in HRG-stimulated TamR cells compared to WT cells, and the opposite results for E2-stimulated cells.

Figure 18:
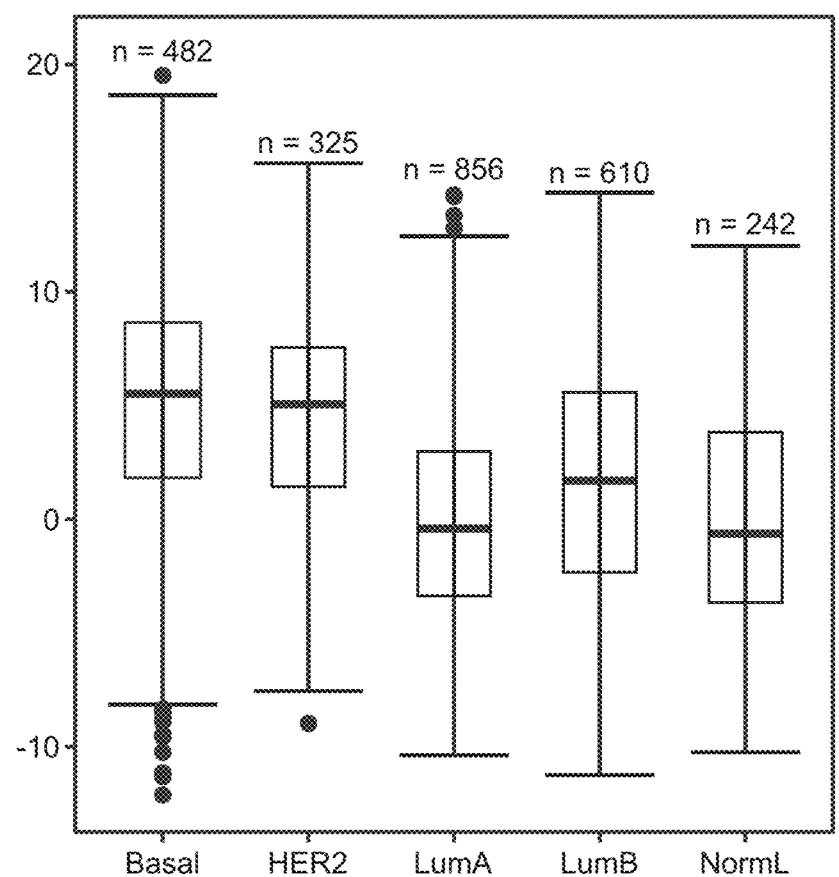
FIG. 18 shows further validation results of the trained exemplary Bayesian network model using the model using the 11 target gene shortlist from Table 2 on breast cancer subgroups in samples from GSE6532, GSE9195, GSE12276, GSE20685, GSE21653, GSE58812, GSE66986, GSE102484, and E-MTAB-365.

Further validation results of the trained exemplary Bayesian network model using the model using the 11 target gene shortlist from Table 2 on breast cancer subgroups in samples from GSE6532, GSE9195, GSE12276, GSE20685, GSE21653, GSE58812, GSE66986, GSE102484, and E-MTAB-365 are shown in FIG. 18 (subgroups (from left to right): Basal; HER2; Luminal A (LumA); Luminal B (LumB); and Normal-like (NormL)). In the diagram, the vertical axis indicates the odds (on a log 2 scale) that the TF element is "present" resp. "absent", which corresponds to the MAPK-AP-1 cellular signaling pathway being active resp. passive. Both high and low AP-1 activity is observed in breast cancer samples in those data sets, while Basal and HER2 subtypes have high AP-1 activity on average. Results of doing a one-way ANOVA followed by a Games-Howell post-hoc test show that almost all groups have significant differences except for HER2 vs. Basal and NormL vs. LumA, see Table 3.

TABLE 3

Results of Games-Howell post-hoc test comparing different subgroups of breast cancer samples as shown in FIG. 18. p-values < 0.05 are considered to be significant.

| Comparison | p adj |
|---|---|
| HER2-Basal | 1 |
| LumA-Basal | 0 |
| LumB -Basal | 0 |
| NormL-Basal | 2.87e−09 |
| LumA-HER2 | 2.87e−09 |
| LumB-HER2 | 0 |
| NormL-HER2 | 2.45e−09 |
| LumB-LumA | 5.34e−06 |
| NormL-LumA | 1 |
| NormL-LumB | 5.40e−05 |

Figure 19:
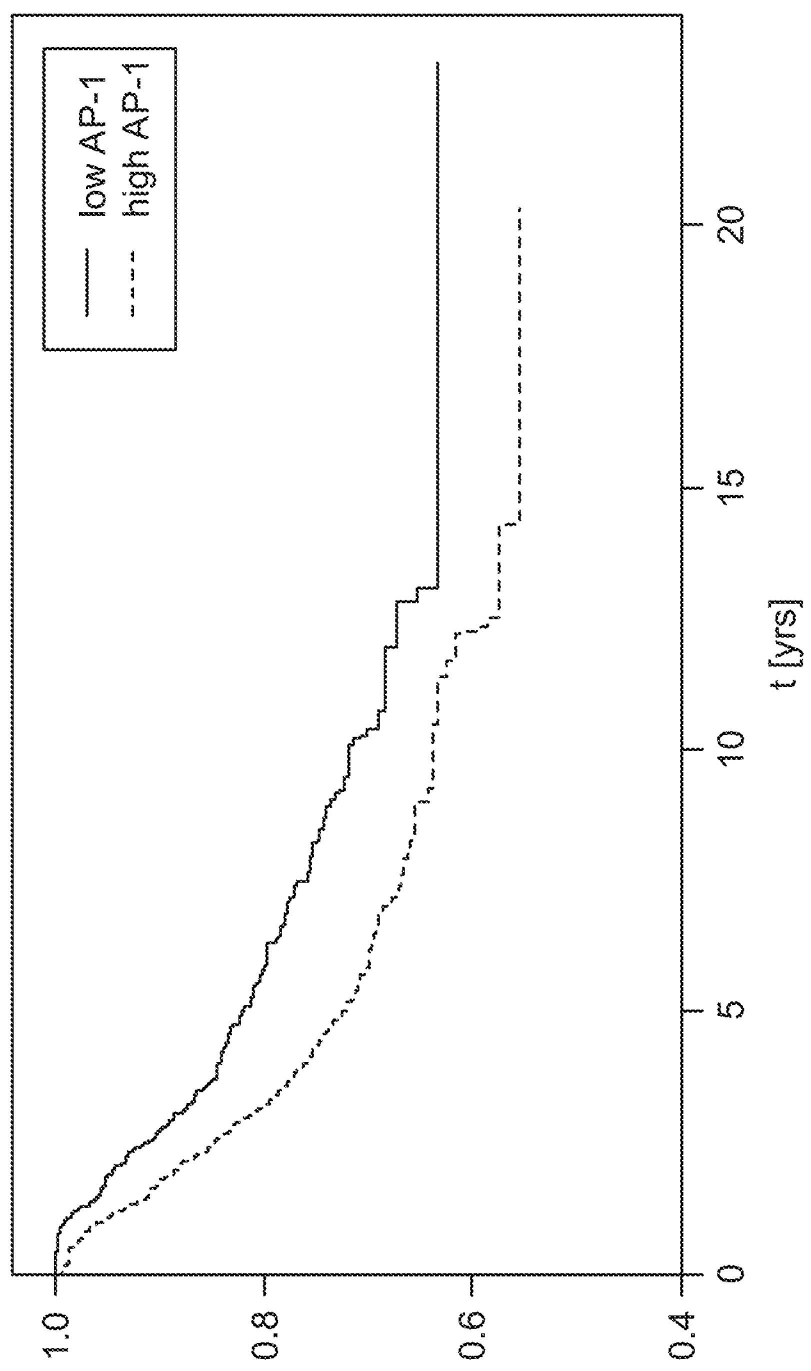
FIG. 19 shows Kaplan-Meier curves of breast cancer patients with high AP-1 activity (as detected with the trained exemplary Bayesian network model using the evidence curated list of target genes (24 target genes list) from Table 1).

FIG. 19 shows Kaplan-Meier curves showing that breast cancer patients with high AP-1 activity (as detected with the trained exemplary Bayesian network model using the evidence curated list of target genes (24 target genes list) from Table 1) have a significantly worse prognosis compared to patients with low AP-1 activity (p=0.000569, log-rank test). Data was taken from GSE6532, GSE9195, GSE20685, GSE21653 and E-MTAB-365.

Figure 20:
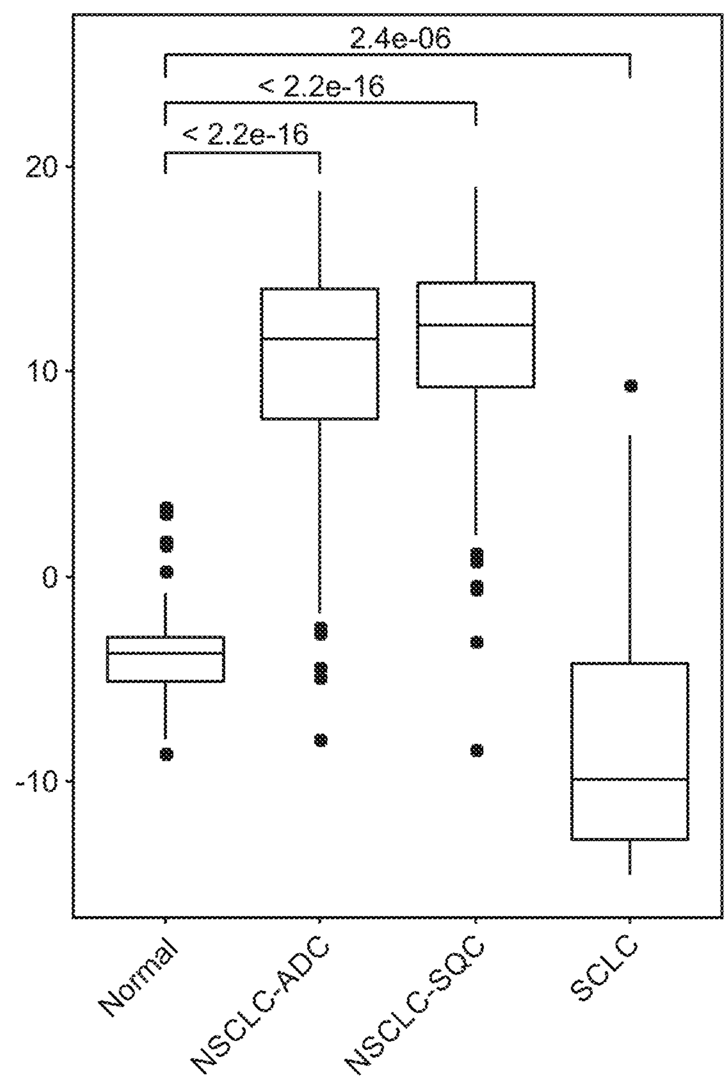
FIG. 20 shows further validation results of the trained exemplary Bayesian network model using the model using the evidence curated list of target genes (24 target genes list) from Table 1 on breast cancer subgroups in samples from GSE5060, GSE10006, GSE10245, GSE13933, GSE19667, GSE28582, GSE30219, GSE33532, GSE43346, and GSE50081.

Further validation results of the trained exemplary Bayesian network model using the model using the evidence curated list of target genes (24 target genes list) from Table 1 on lung cancer subgroups in samples from GSE5060, GSE10006, GSE10245, GSE13933, GSE19667, GSE28582, GSE30219, GSE33532, GSE43346, and GSE50081 are shown in FIG. 20 (subgroups (from left to right): Normal; Non-small cell lung cancer-Adenocarcinoma (NSCLC-ADC); Non-small cell lung cancer-Squamous Cell Carcinoma (NSCLC-SQC); Small-cell lung cancer (SCLC)). In the diagram, the vertical axis indicates the odds (on a log 2 scale) that the TF element is "present" resp. "absent", which corresponds to the MAPK-AP-1 cellular signaling pathway being active resp. passive. High AP-1 activity is observed in NSCLC samples in those data sets, when compared to Normal samples. From scientific literature it is known that AP-1 plays a role in lung cancer (see, for example, Eferl R. and Wagner E. F., "AP-1: a double-edged sword in tumorigenesis", Nature Reviews Cancer, Vol. 3, No. 11, pages 859 to 868, 2003). Lower AP-1 activity is observed in SCLC samples, when compared to Normal samples.

Figure 21:
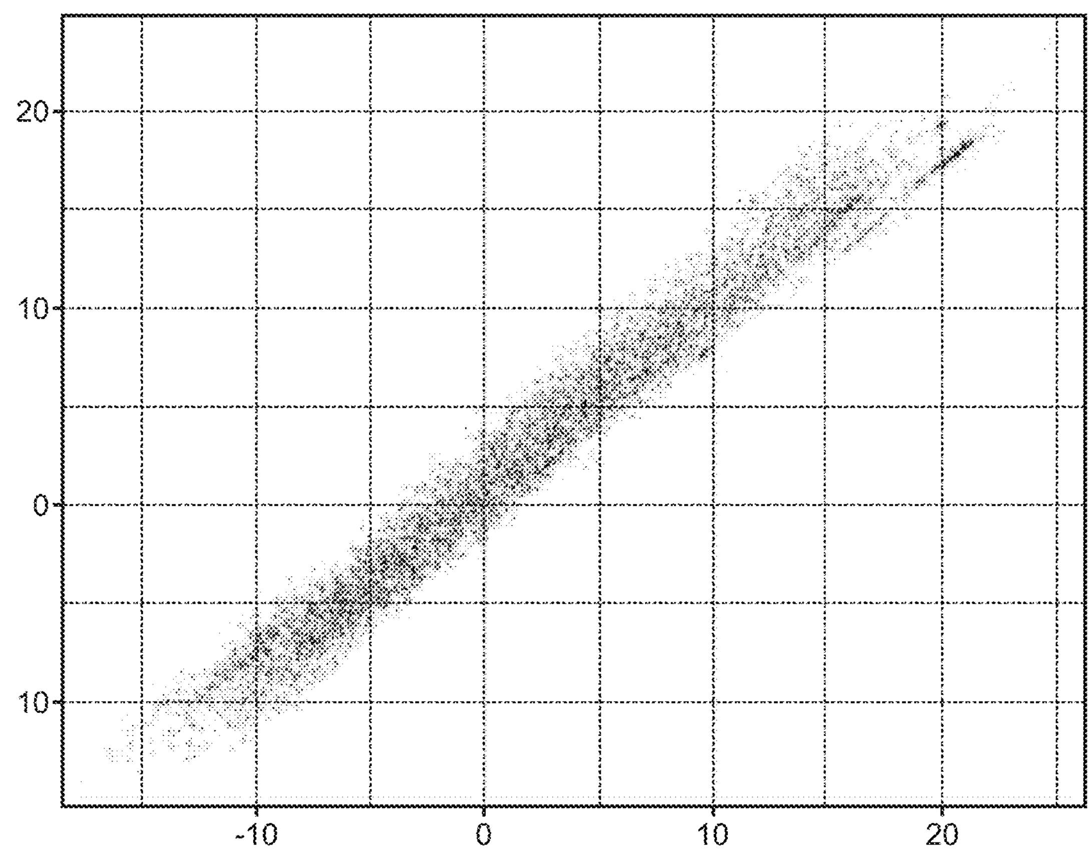
FIG. 21 shows the correlation between the trained exemplary Bayesian network model on 5307 samples from public data sets using the evidence curated list of target genes (24 target genes list) from Table 1 and the 11 target genes shortlist from Table 2, respectively.

FIG. 21 shows the correlation between the trained exemplary Bayesian network model on 5307 samples from public data sets using the evidence curated list of target genes (24 target genes list) from Table 1 and the 11 target genes shortlist from Table 2, respectively. In the diagram, the horizontal axis indicates the odds (on a log 2 scale) that the TF element is "present" resp. "absent", which corresponds to the MAPK-AP-1 cellular signaling pathway being active resp. passive, as predicted by the trained exemplary Bayesian network model using the evidence curated list of target genes (24 target genes list) from Table 1. The vertical axis indicates the same information, as predicted by the trained exemplary Bayesian network model using the 11 target gene shortlist from Table 1 (data sets GSE2677, GSE2842, GSE6532, GSE8742, GSE9195, GSE10245, GSE12276, GSE13710, GSE19804, GSE20685, GSE21618, GSE21653, GSE23630, GSE24290, GSE27914, GSE28878, GSE31912, GSE33532, GSE39338, GSE40117, GSE43346, GSE45417, GSE50081, GSE58235, GSE58812, GSE59230, GSE63074, GSE66082, GSE66853, GSE69986, GSE77803, GSE102287, GSE102484, E-MEXP-2213, E-MEXP-2573, E-MEXP-3040, E-MEXP-3107, E-MTAB-365, E-MTAB-2091, E-TABM-782). The two models are significantly correlated with a p-value of 2.2e-16 and a correlation coefficient of 0.9853.

Instead of applying the mathematical model, e.g., the exemplary Bayesian network model, on mRNA input data coming from microarrays or RNA sequencing, it may be beneficial in clinical applications to develop dedicated assays to perform the sample measurements, for instance on an integrated platform using qPCR to determine mRNA levels of target genes. The RNA/DNA sequences of the disclosed target genes can then be used to determine which primers and probes to select on such a platform.

Validation of such a dedicated assay can be done by using the microarray-based mathematical model as a reference model, and verifying whether the developed assay gives similar results on a set of validation samples. Next to a dedicated assay, this can also be done to build and calibrate similar mathematical models using RNA sequencing data as input measurements.

The set of target genes which are found to best indicate specific cellular signaling pathway activity, e.g., Tables 1 and 2, based on microarray/RNA sequencing based investigation using the calibrated mathematical model, e.g., the exemplary Bayesian network model, can be translated into a multiplex quantitative PCR assay to be performed on a sample of the subject and/or a computer to interpret the expression measurements and/or to infer the activity of the MAPK-AP-1 cellular signaling pathway. To develop such a test (e.g., FDA-approved or a CLIA waived test in a central service lab or a laboratory developed test for research use only) for cellular signaling pathway activity, development of a standardized test kit is required, which needs to be clinically validated in clinical trials to obtain regulatory approval.

The present invention relates to a method comprising determining an activity level of a MAPK-AP-1 cellular signaling pathway in a subject based at least on expression levels of at least three, for example, at least four, at least five, at least six, at least seven, at least eight, at least nine, at least ten or more target genes of the MAPK-AP-1 cellular signaling pathway measured in a sample. The present invention further relates to an apparatus comprising a digital processor configured to perform such a method, a non-transitory storage medium storing instructions that are executable by a digital processing device to perform such a method, and a computer program comprising program code means for causing a digital processing device to perform such a method.

The method may be used, for instance, in diagnosing an (abnormal) activity of the MAPK-AP-1 cellular signaling pathway, in prognosis based on the determined activity level of the MAPK-AP-1 cellular signaling pathway, in the enrollment in a clinical trial based on the determined activity level of the MAPK-AP-1 cellular signaling pathway, in the selection of subsequent test(s) to be performed, in the selection of companion diagnostics tests, in clinical decision support systems, or the like. In this regard, reference is made to the published international patent application WO 2013/011479 A2 ("Assessment of cellular signaling pathway activity using probabilistic modeling of target gene expression"), to the published international patent application WO 2014/102668 A2 ("Assessment of cellular signaling pathway activity using linear combination(s) of target gene expressions"), and to Verhaegh W. et al., "Selection of personalized patient therapy through the use of knowledge-based computational models that identify tumor-driving signal transduction pathways", Cancer Research, Vol. 74, No. 11, 2014, pages 2936-2945, which describe these applications in more detail.

This specification has been described with reference to embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the disclosure.

Sequence Listing:

| Seq. No. | Gene: |
|---|---|
| Seq. 1 | BCL2L11 |
| Seq. 2 | CCND1 |
| Seq. 3 | DDIT3 |
| Seq. 4 | DNMT1 |
| Seq. 5 | EGFR |
| Seq. 6 | ENPP2 |
| Seq. 7 | EZR |
| Seq. 8 | FASLG |
| Seq. 9 | FIGF |
| Seq. 10 | GLRX |
| Seq. 11 | IL2 |
| Seq. 12 | IVL |
| Seq. 13 | LOR |
| Seq. 14 | MMP1 |
| Seq. 15 | MMP3 |
| Seq. 16 | MMP9 |
| Seq. 17 | SERPINE1 |
| Seq. 18 | PLAU |
| Seq. 19 | PLAUR |
| Seq. 20 | PTGS2 |
| Seq. 21 | SNCG |
| Seq. 22 | TIMP1 |
| Seq. 23 | TP53 |
| Seq. 24 | VIM |

The invention claimed is:

1. A method for correcting a calculated activity level of a MAPK-AP-1 cellular signaling pathway in a subject diagnosed with cancer, comprising:

a) calculating an activity level of an AP-1 transcription factor element in a sample isolated from the subject, wherein the activity level of the AP-1 transcription factor element in the sample is associated with MAPK-AP-1 cellular signaling, wherein the activity level of the MAPK-AP-1 cellular signaling pathway is active, and wherein the activity level of the AP-1 transcription factor element in the sample is calculated by:

i) receiving data on expression levels of at least three target genes derived from the sample, wherein the AP-1 transcription factor element controls transcription of the at least three target genes, and wherein the at least three target genes are selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM;

ii) calculating the activity level of the AP-1 transcription factor element in the sample using a calibrated pathway model, wherein the calibrated pathway model compares the expression levels of the at least three target genes in the sample with expression levels of the at least three target genes in the calibrated pathway model which define an activity level of the AP-1 transcription factor element; and, b) calculating the activity level of the MAPK-AP-1 cellular signaling pathway in the sample based on the calculated activity level of the AP-1 transcription factor element in the sample, wherein the calculated activity level of the MAPK-AP-1 cellular signaling pathway in the sample is active;

c) selecting, based on the calculated activity level of the MAPK-AP-1 cellular signaling pathway in the sample, a specific treatment configured to correct the calculated activity level, wherein the specific treatment is a MAPK-AP-1 cellular signaling pathway inhibitor; and d) administering, in response to the calculated activity level of the MAPK-AP-1 cellular signaling pathway in the sample and the selection of the specific treatment configured to correct the calculated activity level, the MAPK-AP-1 cellular signaling pathway inhibitor.

2. The method of claim 1, wherein the at least three target genes are selected from CCND1, EGFR, EZR, GLRX, MMP1, MMP3, PLAU, PLAUR, SERPINE1, SNCG, and TIMP1.

3. The method of claim 1, further comprising assigning a MAPK-AP-1 cellular signaling pathway activity status to the calculated activity level of the MAPK-AP-1 cellular signaling pathway in the sample.

4. The method of claim 3, further comprising displaying the MAPK-AP-1 cellular signaling pathway activity status.

5. The method of claim 1, wherein the calibrated pathway model is a probabilistic model incorporating conditional probabilistic relationships that compare the expression levels of the at least three target genes in the sample with expression levels of the at least three target genes in the calibrated pathway model which define a level of the AP-1 transcription factor element to determine the activity level of AP-1 transcription factor element in the sample.

6. The method of claim 1, wherein the calibrated pathway model is a linear model incorporating relationships that compare the expression levels of the at least three target genes in the sample with expression levels of the at least three target genes in the calibrated pathway model which define a level of the AP-1 transcription factor element to determine the activity level of the AP-1 transcription factor element in the sample.

7. A method of treating a subject suffering from a disease associated with an activated MAPK-AP-1 cellular signaling pathway comprising:

a) receiving information regarding an activity level of a MAPK-AP-1 cellular signaling pathway derived from a sample isolated from the subject, wherein the activity level of the MAPK-AP-1 cellular signaling pathway is active, and wherein the activity level of the MAPK-AP-1 cellular signaling pathway is determined by:

i) calculating an activity level of an AP-1 transcription factor element in a sample isolated from the subject, wherein the activity level of the AP-1 transcription factor element in the sample is associated with MAPK-AP-1 cellular signaling, and wherein the activity level of the AP-1 transcription factor element in the sample is calculated by:

1) Receiving data on expression levels of at least three target genes derived from the sample, wherein the AP-1 transcription factor element controls transcription of the at least three target genes, and wherein the at least three target genes are selected from BCL2L11, CCND1, DDIT3, DNMT1, EGFR, ENPP2, EZR, FASLG, FIGF, GLRX, IL2, IVL, LOR, MMP1, MMP3, MMP9, SERPINE1, PLAU, PLAUR, PTGS2, SNCG, TIMP1, TP53, and VIM;

2) Calculating the activity level of the AP-1 transcription factor element in the sample using a calibrated pathway model, wherein the calibrated pathway model compares the expression levels of the at least three target genes in the sample with expression levels of the at least three target genes in the calibrated pathway model which define an activity level of AP-1 transcription factor element; and, ii) calculating the activity level of the MAPK-AP-1 cellular signaling pathway in the sample based on the calculated activity level of the AP-1 transcription factor element in the sample; and, b) administering to the subject a MAPK-AP-1 inhibitor in response to the received information regarding the activity level of the MAPK-AP-1 cellular signaling pathway.

8. The method of claim 7, wherein the at least three target genes are selected from CCND1, EGFR, EZR, GLRX, MMP1, MMP3, PLAU, PLAUR, SERPINE1, SNCG, and TIMP1.

9. The method of claim 7, wherein the MAPK-AP-1 inhibitor is SP600125, PD98059, PD184352, U0126, Ro092210, or LLZ16402.

10. The method of claim 7, wherein the disease is a cancer or an immune disorder.

* * * * *